US008450505B2

(12) United States Patent
Hedrick

(10) Patent No.: US 8,450,505 B2
(45) Date of Patent: May 28, 2013

(54) POLYMERS BEARING PENDANT PENTAFLUOROPHENYL ESTER GROUPS, AND METHODS OF SYNTHESIS AND FUNCTIONALIZATION THEREOF

(75) Inventor: James Lupton Hedrick, Pleasanton, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/414,881

(22) Filed: Mar. 8, 2012

(65) Prior Publication Data

US 2012/0172603 A1    Jul. 5, 2012

Related U.S. Application Data

(60) Division of application No. 12/770,857, filed on Apr. 30, 2010, now Pat. No. 8,143,369, which is a continuation-in-part of application No. 12/476,903, filed on Jun. 2, 2009, now abandoned.

(51) Int. Cl.
*C07D 321/00* (2006.01)

(52) U.S. Cl.
USPC .......................................... 549/228

(58) Field of Classification Search
USPC .......................................... 549/228
See application file for complete search history.

(56) References Cited

U.S. PATENT DOCUMENTS

| | | | |
|---|---|---|---|
| 4,102,912 A | 7/1978 | Carr | |
| 4,613,442 A | 9/1986 | Yuki et al. | |
| 4,782,131 A | 11/1988 | Sweeny | |
| 4,831,100 A | 5/1989 | Komatsu et al. | |
| 4,888,410 A | 12/1989 | Komatsu et al. | |
| 5,091,543 A | 2/1992 | Grey | |
| 5,357,027 A | 10/1994 | Komatsu | |
| 5,424,473 A | 6/1995 | Galvan et al. | |
| 5,523,399 A | 6/1996 | Asaka et al. | |
| 6,300,458 B1 | 10/2001 | Vandenberg | |
| 6,664,372 B1 | 12/2003 | Janda et al. | |
| 8,013,065 B2 | 9/2011 | Hedrick et al. | |
| 8,044,194 B2 | 10/2011 | Dubois et al. | |
| 2007/0015932 A1 | 1/2007 | Fujita et al. | |
| 2007/0232751 A1 | 10/2007 | Ludewig et al. | |
| 2007/0298066 A1 | 12/2007 | Alferiev et al. | |
| 2009/0208553 A1 | 8/2009 | Kemp et al. | |
| 2010/0280242 A1 | 11/2010 | Hedrick et al. | |
| 2010/0305300 A1 | 12/2010 | Coulembier et al. | |
| 2011/0150977 A1 | 6/2011 | Hedrick et al. | |
| 2011/0151566 A1 | 6/2011 | Hedrick et al. | |
| 2011/0152167 A1 | 6/2011 | Hedrick et al. | |
| 2011/0182996 A1 | 7/2011 | Fukushima et al. | |
| 2011/0243848 A1 | 10/2011 | Appel et al. | |
| 2011/0269917 A1 | 11/2011 | Fujiwara et al. | |

FOREIGN PATENT DOCUMENTS

WO    2007003054 A1    1/2007

OTHER PUBLICATIONS

Mullen, Brian D., et al., J. Polym Sci, Part A: Polym Chem 2003, 41(13), 1978-1991.*
Al-Azemi, et al., Enzyme-Catalyzed Ring0Opening Copolymerizaton of 5- Methyl-5-benzyloxycarbonyl-1,3-dioxan-2-one (MBC) with Trimethylene Carbonate (TMC): Synthesis and Characterization, Biomacromolecules 2000, 1, 493-500.
Cooley, et al., Oligocarbonate Molecular Transporters: Oligomerization Based Syntheses and Cell Penetrating Studies, Jamer. Chem. Soc., 131(45), 16401-16403, published Nov. 18, 2009.
Coulembier, et al., "Hydrogen-Bonding Catalysts Based on Fluorinated Alcohol Derivatives for Living Polymerization", Angew. Chem. Int. Ed., 48, (2009), 5170-5173, Wiley Interscience, US.
Efimov, et al., "Dipentafluorophenyl carbonate—a reagent forthe synthesis of oligonucleotides and their conjugates," Nucleic Acids Res. 1993, 21, 5337.
Fujita, et al., "Phosgene-Free Synthesis of N-Carboxyanhydrides of alpha-Amino Acids Based on Bisarylcarbonates as Starting Compounds," J. Polym. Sci. A. Polym. Chem. 2007, 45, 5365-5369.
Fujiwara, et al., PCTUS1127354, filed Mar. 7, 2011, International Search Report, mailing date Apr. 29, 2011.
Fujiwara, et al., PCTUS1127354, filed Mar. 7, 2011, Written Opinion, mailing date Apr. 29, 2011.
Han, et al., "Azatides: Solution and Liquid Phase Syntheses of a New Peptidomimetic," JACS, 1996, 2539-2544.
Han, et al., "Grafting BSA onto Poly[(L-lactide)-co-carbonate]Microspheres by Click Chemistry", Macromol. Biosci (2008), 8, 638-644, Wiley Interscience, US.
Han, et al., "Investigations of Azapeptides as Mimetics of Leu-Enkephalin," Bioorg. Med. Chem. 1998, 8, 117-120.
Hu, et al., "Novel Aliphatic Poly(ester-carbonate) with Pendant Allyl Ester Groups and its Folic Acid Functionalization", Journal of Polymer Science: Part A: Polymer Chemistry, vol. 46, (2008), 1852-1861, US.
Lu, et al., "Click Chemistry Functionalized Polymeric Nanoparticles Target Corneal Epithelial Cells through RGD-Cell Surface Receptors", Bioconjugate Chem., vol. 20, No. 1, (2009), 87-94, published on web Dec. 18, 2008, US.
Lu, et al., "Sugars-Grafted Aliphatic Biodegradable Poly(L-lactide-co-carbonate)s by Click Reaction and their Specific Interaction with Lectin Molecules", Journal of Polymer Science: Part A: Polymer Chemistry, vol. 45, (2007), 3204-3217, Wiley, US.
Pratt, et al., "Tagging alcohols with cyclic carbonate: a versatile equivalent of (meth)acrylate for ring-opening polymerization", Chem. Commun, (2008), 114-116, Royal Society of Chemistry, UK, first published Oct. 25, 2007 on web.
Shi, et al., "Furan-functionalized co-polymers for targeted drug delivery: characterization, self-assembly and drug encapsulation", J. Biomater. Sci. Polymer Edn, vol. 19, No. 9, (2008), 1143-1157, Koninklijke Brill, US.

(Continued)

*Primary Examiner* — Johann R Richter
*Assistant Examiner* — Kofi Adzamli
(74) *Attorney, Agent, or Firm* — Michael R. Roberts

(57) ABSTRACT

A one pot method of preparing cyclic carbonyl compounds comprising an active pendant pentafluorophenyl ester group is disclosed. The cyclic carbonyl compounds can be polymerized by ring opening methods to form ROP polymers comprising repeat units comprising a side chain pentafluorophenyl ester group. Using a suitable nucleophile, the pendant pentafluorophenyl ester group can be selectively transformed into a variety of other functional groups before or after the ring opening polymerization.

7 Claims, 14 Drawing Sheets

OTHER PUBLICATIONS

Shi, et al., "Immuno-Polymeric Nanoparticles by Diels-Alder Chemistry", Angew. Chem. Int. Ed, 46, (2007), 6126-6131, Wiley Interscience, US.

Shi, et al., "The immobilization of proteins on biodegradable polymer fibers via click chemistry", Biomaterials 29 (2008), 1118-1126, Elsevier, US, first published online Nov. 26, 2007.

Simon, et al., online abstract for the Aug. 13, 2009 poster at http://cpima.stanford.edu/forum2009/a-new-chemical-pathway-for-multifunctional-cyclic-carbonate-compounds/.

Simon, et al., poster displayed during an open-house held on Aug. 13, 2009 at the Almaden Research Center in San Jose.

Xie, et al., "A Biodegradable Diblcok Copolymer Poly(ethylene glycol)-block-poly(L-lactide-co-2-methyl-2-carboxylpropylene carbonate): Docetaxel and RGD Conjugation", Journal of Applied Polymer Science, vol. 110, (2008), 2961-2970, Wiley Periodicals, first published online Sep. 3, 2008.

Zhou, et al., "Synthesis and Characterization of Novel Aliphatic Poly(carbonate-ester)s with Functional Pendent Groups", Macromol. Rapid Commun., 26, (2005), 1309-1314, Wiley, US.

USPTO, Non-Final Office Action, U.S. Appl. No. 13/414,895, mailing date Jan. 18, 2013.

* cited by examiner

POLYMERS BEARING PENDANT PENTAFLUOROPHENYL ESTER GROUPS, AND METHODS OF SYNTHESIS AND FUNCTIONALIZATION THEREOF

CROSS REFERENCE TO RELATED APPLICATIONS

This application is a division of, and claims the benefit of, pending nonprovisional U.S. application Ser. No. 12/770,857 entitled "POLYMERS BEARING PENDANT PENTAFLUOROPHENYL ESTER GROUPS, AND METHODS OF SYNTHESIS AND FUNCTIONALIZATION THEREOF" filed on Apr. 30, 2010, which is a continuation-in-part of, and claims the benefit of, abandoned nonprovisional U.S. application Ser. No. 12/476,903 entitled "CYCLIC MONOMERS FOR RING OPENING POLYMERIZATIONS AND METHODS OF PREPARATION THEREOF" filed on Jun. 2, 2009, each herein incorporated by reference in its entirety.

BACKGROUND

The incorporated parent disclosure (Part I) is generally related to cyclic monomers bearing pendant pentafluorophenyl ester groups for ring-opening polymerizations, and methods of preparation thereof. The continuation-in-part disclosure (Part II) is generally related to polymers bearing pendant pentafluorophenyl ester groups, methods of their synthesis, and methods of their functionalization; and more specifically to polycarbonates bearing pendant pentafluorophenyl ester groups and their functionalization.

tional simplicity of organocatalysts improves, a wider variety of ROP monomers is sought to generate polymer microstructures unique to ROP methods.

Initial efforts to employ substituted lactones as ROP monomers were hampered by the sensitivity of the organocatalysts to steric bulk of the monomer, particularly at the alpha-position. The alpha-position of cyclic esters is the only site capable of a general substitution reaction. Consequently, this approach provided limited numbers of monomers. More encouraging was the finding that trimethylene carbonate (TMC) was efficiently polymerized by organocatalysts such as thiourea/1,8-diazabicyclo[5.4.0]undec-7-ene (TU-DBU) or 1,5,7-triaza-bicyclo[4.4.0]dec-5-ene (TBD), for two reasons: first, TMC-like monomers can be derived from readily available 1,3-diols, and second, those 1,3-diols can be chosen so as to only bear substituents at the 2-position (the 5-position in the cyclic carbonate), where the substituent does not interfere sterically with the ring opening polymerization.

A number of cyclic carbonate monomers have been generated and polymerized in the past by more conventional anionic or organometallic ROP methods. Excessively bulky substituents (e.g., 2,2-diphenyl) in the 1,3-diol can make ring-opening of the corresponding cyclic carbonate thermodynamically unfavorable. Thus, efforts were focused on monomers derived from 2,2-bis(methylol)propionic acid (bis-MPA), a common building block for biocompatible dendrimers. Cyclic carbonate monomers have been generated from bis-MPA with a number of different functional groups attached to the carboxylate, usually involving methods similar to those used in dendrimer synthesis (i.e., acetonide protection and deprotection followed by carbonate formation). Scheme 1 illustrates known synthetic routes to functionalized cyclic carbonyl compounds from bis-MPA (Pratt et al. *Chem. Comm.* 2008, 114-116).

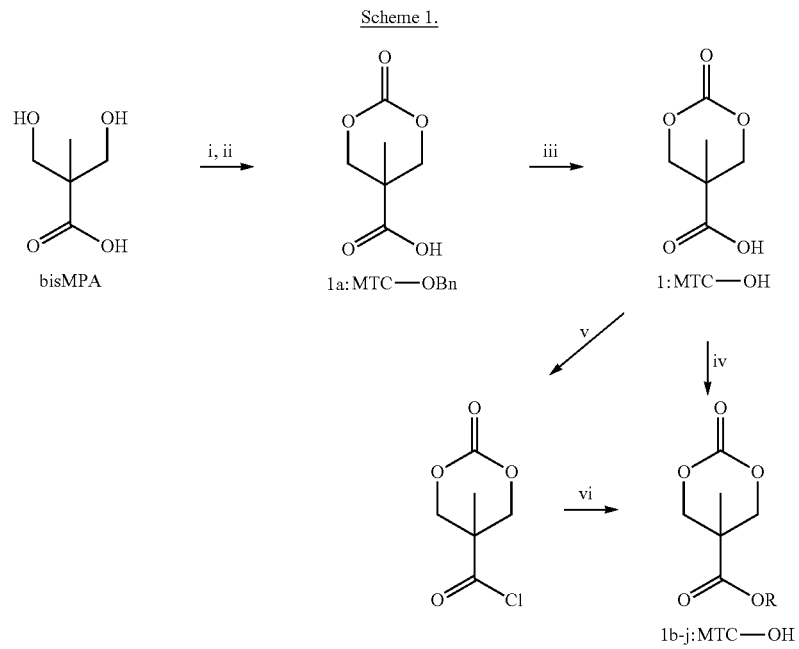

Scheme 1.

Part I. Background

In general, the structural variety of monomers for ring opening polymerization (ROP) is significantly less than the number of monomers available for controlled radical polymerization (CRP). However, as the effectiveness and opera- The following conditions apply to the reactions in Scheme 1: (i) benzyl bromide (BnBr), KOH, DMF, 100° C., 15 hours, 62% yield. (ii) triphosgene, pyridine, $CH_2Cl_2$, −78° C. to 0° C., 95% yield. (iii) Pd/C (10%), $H_2$ (3 atm), EtOAc, RT, 24 hours, 99% yield. (iv) ROH, dicyclohexylcarbodiimide (DCC), THF, room temperature (RT), 1-24 hours. (v) (COCl)$_2$, THF, RT, 1 hour, 99% yield. (vi) ROH, NEt$_3$, RT, 3 hours.

The cyclic carbonate acid monomer, MTC-OH, (1),

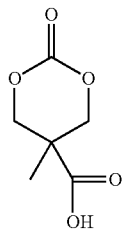

(1)

provides great versatility in preparing functionalized carbonate monomers for ROP, similar to meth(acrylic) acid for CRP (see Pratt et al.). For example, the reaction of an alcohol or amine with an active ester of a (meth)acrylic acid provides a (meth)acrylate or (meth)acrylamide monomer for CRP. Likewise, the reaction of an arbitrary alcohol or amine with an active ester of MTC-OH can generate a cyclic carbonate ester or cyclic carbonate amide monomer for ROP.

Two procedures for esterifying MTC-OH are typically employed: a) direct coupling of MTC-OH with an alcohol using dicyclohexylcarbodiimide (DCC); or b) conversion of MTC-OH to the acyl chloride with oxalyl chloride followed by reaction with an alcohol (ROH, wherein R is a substituent comprising 1 to 20 carbons) or amine in the presence of base, as shown in Scheme 1. The latter method has the advantage that the salt byproducts are easily removed; however, the acyl chloride intermediate is extremely water sensitive which presents storage and handling concerns. In addition, both procedures are labor and resource intensive, use significant amounts of solvent and reagents, and are not environmentally "green."

"Green" chemistry is a concept that is being embraced around the world to ensure continued economic and environmental prosperity. Modern synthetic methodologies are encouraged to preserve performance while minimizing toxicity, use renewable feedstocks, and use catalytic and/or recyclable reagents to minimize waste. Green chemistry is the design and development of chemical products and processes that reduce or eliminate the use of substances harmful to health or environment.

Part II. Background

Biodegradable polymers are of intense for use in a variety of nanomedicine applications including drug delivery/target therapeutics, imaging agents, and tissue engineering. The two most common approaches to the synthesis of biodegradable polymers are the ring-opening polymerization (ROP) of cyclic esters (e.g., lactones) and cyclic carbonates to produce polyesters and polycarbonates, respectively, illustrated in Scheme A.

Scheme A.

Cyclic Esters

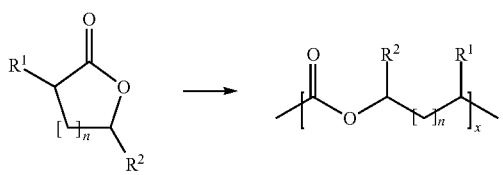

Cyclic Carbonates

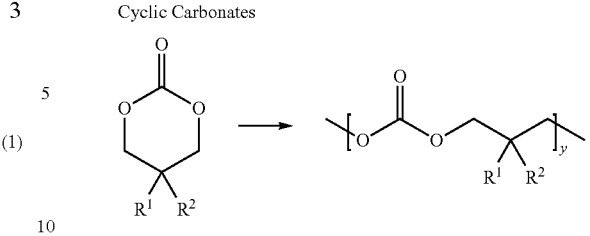

wherein $R^1$ and $R^2$ generally represent hydrogen or a short chain monovalent hydrocarbon substituent, and n is 1 to 5. As a class of biodegradable polymers, polycarbonates have generally been found to exhibit significantly increased rates of biodegradation in the human body relative to polyesters.

Cyclic carbonate monomers based on MTC-OH require that the carboxylic acid group be protected (most commonly as a benzyl ester) or functionalized prior to ring opening polymerization, as shown in Scheme B.

Scheme B.

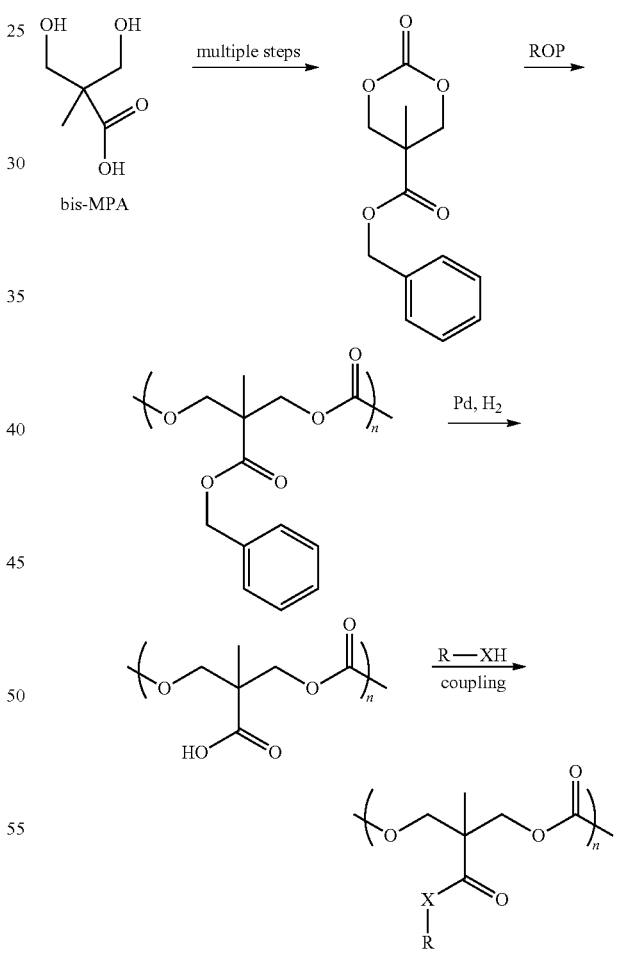

The protected/functionalized monomer is then homopolymerized or copolymerized with other cyclic carbonate or cyclic ester monomers (e.g., lactide and/or epsilon-caprolactone). After polymerization the benzyl protecting groups can be removed by hydrogenolysis, to form side chain carboxylic acid groups. The carboxylic acid groups can then be converted to esters or amides with a suitable nucleophile, R—XH, using known coupling chemistry (e.g., see Jing et al., *J. Appl. Polym. Sci.* 2008, 110, 2961-2970), wherein R—XH represents an alcohol, an amine, or a thiol. Alternatively, molecules can be coupled to the polycarbonate using various other coupling reactions such as Diels-Alder reactions, 1,3-dipolar cycloadditions, and thiol-ene reactions. In these cases, a reactive functional group (e.g., a group containing a diene, azide, alkyne, or alkene functionality) is attached to the polymer backbone through a pendant ester/amide linkage. The reactive functional group can be attached to the monomer prior to polymerization (i.e., during monomer synthesis) or to the polymer after polymerization. An appropriately functionalized cargo molecule (e.g., comprising a dienophile, an alkyne, an azide, or a thiol functionality) can then be coupled to the polymer by reaction with the pendant reactive functional group. Examples using propargyl or allyl functionalized cyclic carbonate monomers are described by Jing et al., in *Biomaterials* 2008, 29, pgs. 1118-26; *Macromol. Biosci.* 2008, 8, pgs. 638-644; *J. Poly. Sci. A: Polym. Chem.* 2007, 45, pgs. 3204-3217; and *J. Poly. Sci. A: Polym. Chem.* 2008, 46, pgs. 1852-1861. Examples in which furan- or azide-functionalized groups are attached to the pendant carboxylic acid groups of the polycarbonate are described by Shoichet et al., in *Bioconj. Chem.* 2009, 20, pgs. 87-94; *J. Biomat. Sci. Polym. Ed.* 2008, 19, pgs. 1143-57; *Angewandte Chem. Int. Ed.* 2007, 46, pgs. 6126-6131; and WO 2007/003054A1. These approaches require significant numbers of synthetic steps to incorporate the required reactive functional groups into the cyclic carbonate monomer/polycarbonate, as well as the cargo molecule.

Alternatively, Zhuo et al., *Macromol. Rapid Commun.* 2005, 26, pgs. 1309, demonstrated the copolymerization of, and subsequent functionalization of, a cyclic carbonate monomer bearing a reactive pendant succinimidyl ester. The synthesis of this monomer required 4 steps and afforded only a low yield (~20%). In addition, copolymers made with the succinimidyl ester-functionalized cyclic carbonate had broad polydispersities (PDI 1.8-2.9) indicating that this chemistry may be unsuitable for the synthesis of materials having tailored molecular architectures. Most problematically, attempts to polymerize this monomer using organic catalysts were unsuccessful. One reason for this is the insolubility of the monomer at room temperature in solvents commonly used for ring opening polymerizations (e.g., toluene), which required the use of DMSO.

As a result of the aforementioned limitations of the known art, a more versatile and straightforward approach to the preparation of ROP polymers bearing reactive side chain groups is needed, in particular polycarbonates bearing reactive side chain groups. The reactive side chain groups should enable direct functionalization of the ROP polymer.

BRIEF SUMMARY

The parent disclosure of Part I addresses the need to expand the gamut of ROP monomers while still applying "green" principles to the processes and chemical intermediates involved, such as the use of recyclable and less toxic materials. The continuation-in-part disclosure of Part II addresses the need to efficiently form biodegradable polymers that can easily be functionalized in a post-polymerization reaction.

Part I. Brief Summary

In one embodiment a cyclic carbonyl compound comprises a pentafluorophenyl ester and a functional group selected from the group consisting of cyclic carbonate, cyclic carbamate, cyclic urea, cyclic thiocarbonate, cyclic thiocarbamate, cyclic dithiocarbonate, and combinations thereof.

Further disclosed is a cyclic carbonyl compound selected from the group consisting of MTC-NiP, MTC-NMe$_2$, MTC-BnAmine, MTC-OCH$_2$CH$_2$CH$_2$Br, MTC-OCH$_2$CHCH$_2$, MTC-dinitroPHS, MTC-TFE.

Also disclosed is a method of preparing a cyclic carbonyl monomer comprising forming a first mixture comprising a precursor compound, bis(pentafluorophenyl) carbonate, an optional solvent, and a catalyst; wherein the precursor compound has a structure comprising two or more carbons, a carboxy group, and two X groups, each X group independently selected from the group consisting of hydroxyl group, primary amine, secondary amine, thiol group, and combinations thereof; and agitating the first mixture at a temperature effective to form a second mixture comprising the cyclic carbonyl monomer; wherein the cyclic carbonyl monomer comprises a pentafluorophenyl ester derived from the carboxy group, and a cyclic carbonyl group derived from the two X groups, the cyclic carbonyl group selected from the group consisting of cyclic carbonate, cyclic urea, cyclic carbamate, cyclic thiocarbonate, cyclic thiocarbamate, and cyclic dithiocarbonate.

A method of forming a second cyclic carbonyl monomer, comprises forming a first mixture comprising a first cyclic carbonyl monomer comprising a pentafluorophenyl ester and a cyclic carbonyl group, the cyclic carbonyl group selected from the group consisting of cyclic carbonate, cyclic urea, cyclic carbamate, cyclic thiocarbonate, cyclic thiocarbamate, and cyclic dithiocarbonate; a nucleophile selected from the group consisting of an alcohol, amine, and thiol; an optional second catalyst; and an optional second solvent; and agitating the first mixture at a temperature effective to form a second mixture comprising a second cyclic carbonyl monomer comprising an amide, an ester or thioester derived from the pentafluorophenyl ester group, without altering the cyclic carbonyl group of the first cyclic carbonyl monomer.

Further disclosed is a biodegradable polymer derived from a cyclic monomer by ring-opening polymerization, the cyclic monomer selected from the group consisting of MTC-NiP, MTC-NMe$_2$, MTC-BnAmine, MTC-OCH$_2$CH$_2$CH$_2$Br, MTC-OCH$_2$CHCH$_2$, MTC-dinitroPHS, MTC-TFE, and combinations thereof.

In yet another embodiment, a method of ring-opening polymerization comprises forming a reaction mixture comprising a cyclic carbonyl monomer, a catalyst, an initiator, and an optional solvent; and heating the reaction mixture to form a biodegradable polymer derived from the cyclic carbonyl monomer; wherein the cyclic carbonyl monomer is selected from the group consisting of MTC-NiP, MTC-NMe$_2$, MTC-BnAmine, MTC-OCH$_2$CH$_2$CH$_2$Br, MTC-OCH$_2$CHCH$_2$, MTC-dinitroPHS, MTC-TFE, and combinations thereof.

Part II. Brief Summary

A biodegradable polymer is disclosed, comprising:

a chain fragment; and a first polymer chain; wherein i) the chain fragment comprises a first backbone heteroatom, the first backbone heteroatom linked to a first end unit of the first polymer chain, the first backbone heteroatom selected from the group consisting of oxygen, nitrogen, and sulfur, ii) the first polymer chain comprises a second end unit comprising a nucleophilic group selected from the group consisting of hydroxy group, primary amine groups, secondary amine groups, and thiol group, and iii) the first polymer chain comprises a first repeat unit comprising a) a backbone functional group selected from the group consisting of carbonate, ureas, carbamates, thiocarbamates, thiocarbonate, and dithiocarbonate, and b) a tetrahedral backbone carbon, the tetrahedral backbone carbon being linked to a first side chain comprising a pentafluorophenyl ester group.

A method is disclosed, comprising:

agitating a first mixture comprising i) a precursor compound comprising two or more carbons, two or more hydroxy groups, and one or more carboxylic acid groups, ii) bis(pentafluorophenyl) carbonate, and iii) a catalyst, thereby forming a first cyclic carbonate compound comprising a pendant pentafluorophenyl ester group.

Another method is disclosed, comprising:

forming a first mixture comprising a catalyst, an initiator comprising a nucleophilic group selected from the group consisting of alcohols, amines, and thiols, an optional accelerator, an optional solvent, and a first cyclic carbonyl compound comprising a pentafluorophenyl ester group; and agitating the first mixture, thereby forming a first ROP polymer by ring opening polymerization of the first cyclic carbonyl compound, the first ROP polymer comprising a first polymer chain linked to a chain fragment derived from the initiator; wherein i) the chain fragment comprises a first backbone heteroatom derived from the nucleophilic group, the first backbone heteroatom linked to a first end unit of the first polymer chain, the first backbone heteroatom selected from the group consisting of oxygen, nitrogen, and sulfur, ii) the first polymer chain comprises a second end unit comprising a nucleophilic group selected from the group consisting of hydroxy group, primary amine groups, secondary amine groups, and thiol group, and iii) the first polymer chain comprises a first repeat unit, the first repeat unit comprising a) a backbone functional group selected from the group consisting of carbonate, ureas, carbamates, thiocarbamates, thiocarbonate, and dithiocarbonate, and b) a tetrahedral backbone carbon, the tetrahedral backbone carbon being linked to a first side chain comprising a pentafluorophenyl ester group.

Additional features and advantages are realized through the techniques of the present invention. Other embodiments and aspects of the invention are described in detail herein and are considered a part of the claimed invention. For a better understanding of the invention with the advantages and the features, refer to the description.

BRIEF DESCRIPTION OF THE SEVERAL VIEWS OF THE DRAWINGS

Part I.

FIG. 1 is a picture containing two magnetic resonance spectrographs, $^1$H NMR and $^{19}$F NMR, of MTC-PhF$_5$, (5).

FIG. 2 is a $^1$H NMR spectrograph of MTC-Et, (6).

FIG. 3 is a $^1$H NMR spectrograph of MTC-BnAmine, (7).

FIG. 4 is a $^1$H NMR spectrograph of MTC-OCH$_2$CCH, (8).

FIG. 5 is a $^1$H NMR spectrograph of MTC-OCH$_2$CH$_2$Br, (9).

FIG. 6 is a $^1$H NMR spectrograph of MTC-OCH$_2$CHCH$_2$, (10).

FIG. 7 is a $^1$H NMR spectrograph of MTC-OCH$_2$CH$_2$SS(2-Py), (11).

FIG. 8 is a $^1$H NMR spectrograph of MTC-OCH$_2$CH$_2$OTHP, (12).

FIG. 9 is a $^1$H NMR spectrograph of MTC-OCH$_2$CH$_2$NHBoc, (13).

FIG. 10 is a $^1$H NMR spectrograph of MTC-Benz, (14).

FIG. 11 is a $^1$H NMR spectrograph of MTC-OCH$_2$CH$_2$OCH$_2$OMe, (15).

FIG. 12 is a $^1$H NMR spectrograph of MTC— MTC-dinitroPHS, (16).

Part II.

FIG. 13 is a graph of the polymer weight average molecular weight $M_w$ as a function of conversion of monomer MTC-PhF$_5$ in the ring opening polymerization of Example 16.

FIG. 14 is a graph of each monomer conversion versus reaction time in the copolymerization of pentafluorophenyl 5-methyl-2-oxo-1,3-dioxane-5-carboxylate (diamonds) and ethyl 5-methyl-2-oxo-1,3-dioxane-5-carboxylate (triangles) of Example 18.

FIG. 15 is a graph of monomer conversion versus reaction time in the copolymerization of pentafluorophenyl 5-methyl-2-oxo-1,3-dioxane-5-carboxylate (diamonds) and L-lactide (squares).

DETAILED DESCRIPTION

Figure 1:
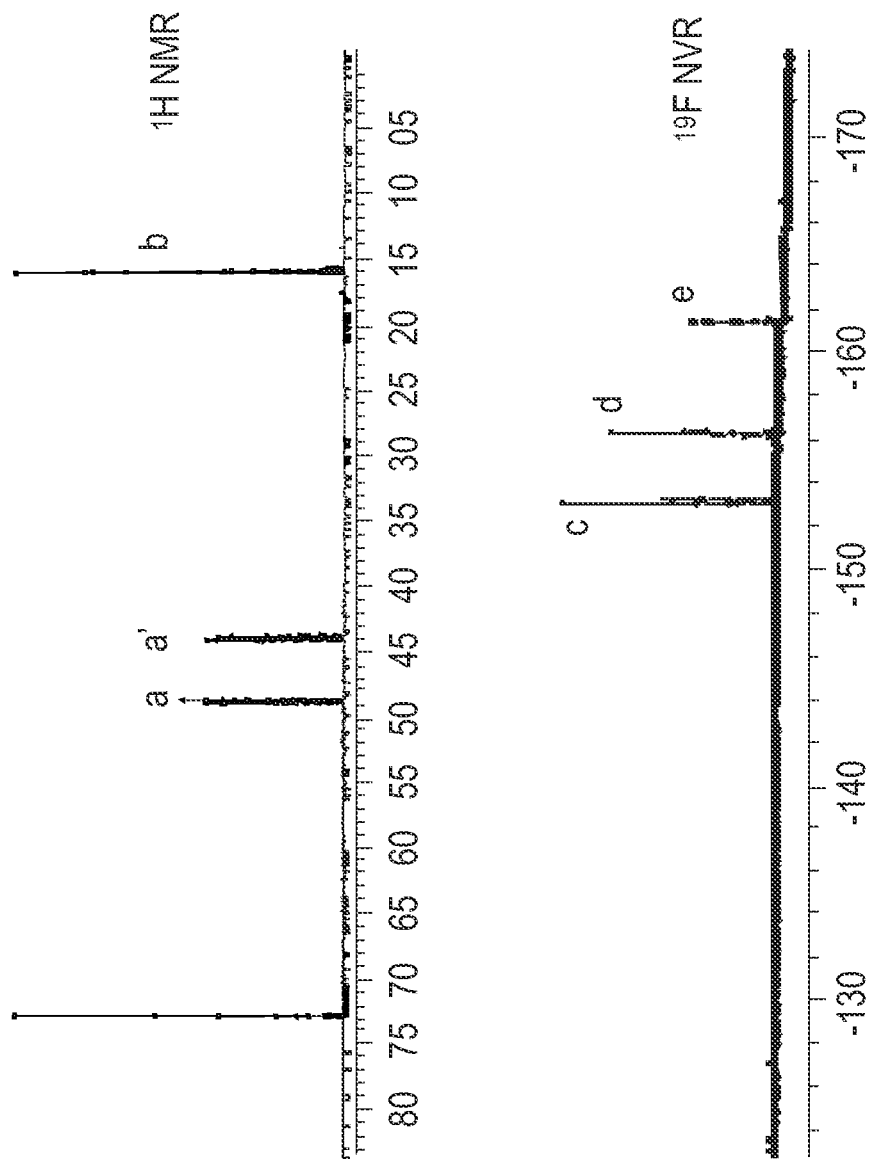
FIGS. 1-12

The following detailed description has two parts. Part I contains the parent Detailed Description and Examples. Methods 1-3 are labeled and given section headings for clarity. Part II, containing the continuation-in-part disclosure and examples can be found following the Examples section of Part I.

Part I. Detailed Description

New cyclic carbonyl compounds are disclosed comprising a pentafluorophenyl ester and a functional group selected from cyclic carbonate, cyclic carbamate, cyclic urea, cyclic thiocarbonate, cyclic thiocarbamate, cyclic dithiocarbonate, and combinations thereof. Also described is a simple one step method (Method 1) for preparing the cyclic carbonyl compound, referred to as the first cyclic monomer. Further disclosed is a method (Method 2) of preparing a second cyclic monomer, by reacting the active pentafluorophenyl ester of the first cyclic monomer with an alcohol, amine or thiol to form a different ester, an amide or a thioester respectively, without altering the cyclic carbonyl moiety of the first cyclic monomer. Each of the described methods is mild, high yielding, and environmentally safer than methods involving reagents such as phosgene. The first and second cyclic monomers are potentially capable of forming ROP polycarbonates and other polymers by ROP methods having unique pendant functionalities and properties.

The first cyclic monomer is prepared by the reaction of a cyclic carbonyl precursor compound (referred to simply as precursor compound) with bis(pentafluorophenyl) carbonate (PFC), having the formula (2):

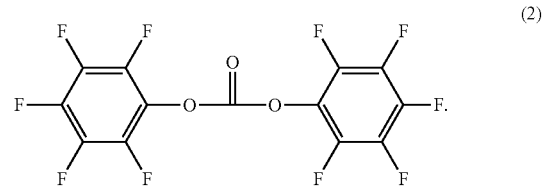 [SMILES: O=C(Oc1c(F)c(F)c(F)c(F)c1F)Oc1c(F)c(F)c(F)c(F)c1F]

(2)

The cyclic carbonyl moiety and the pentafluorophenyl ester moiety are formed in one step in the reaction with PFC. PFC is less toxic than other reagents used for preparing cyclic carbonyl compounds (e.g., phosgene). PFC is a crystalline solid at room temperature which, being less sensitive to water than phosgene, can be easily stored, shipped, and handled. PFC does not require elaborate reaction and workup conditions. Moreover, the pentafluorophenol byproduct produced during the disclosed cyclization reactions is less volatile, less acidic, and less corrosive than hydrochloric acid. These advantages reduce the cost and complexity of the reactions, and potentially widen the scope of the starting materials to include compounds containing acid-sensitive groups. In addition, the pentafluorophenol byproduct can be readily recycled back into PFC. In an embodiment, the first cyclic monomer formed in the reaction has a single pentafluorophenyl ester group.

PFC has been employed previously in the bioorganic community as a coupling agent for oligonucleotides (see: Efimov et al., Nucleic Acids Res., 1993, 21. 5337), for producing peptide mimics such as diazatides by Janda at Scripps (see: Bioorg. Med. Chem., 1998, 8, 117-120; JACS, 1996, 118, 2539-2544; and U.S. Pat. No. 6,664,372), and in the synthesis of N-carboxyanhydrides of amino acids (see: Fujita et al., J. Polym. Sci. A. Polym. Chem., 2007, 45, 5365-5369; and US Patent Publication 2007/0015932). However, PFC has not been used for the preparation of cyclic carbonates, cyclic carbamates, cyclic ureas, cyclic thiocarbonates, cyclic thiocarbamates, and cyclic dithiocarbonates.

Method 1. Preparation of the First Cyclic Monomer.

The method of preparing a first cyclic monomer comprises forming a first mixture comprising bis(pentafluorophenyl) carbonate, a catalyst, an optional solvent, and a precursor compound. The precursor compound comprises three or more carbons, two X groups, and one or more carboxy groups (i.e., —COOH). The two X groups independently represent an alcohol, a primary amine, a secondary amine, or a thiol group. Advantageously, it has been discovered that when the precursor compound also comprises a carboxy group the reaction yields a cyclic carbonyl compound in which the carboxy group is simultaneously converted to a pentafluorophenyl ester. The formation of the cyclic carbonyl moiety and the transformation of the carboxy group into an activated ester occurs in a single process step under mild conditions. This inventive process eliminates the multi-step process using protection/deprotection reactions, eliminates the use of expensive and/or hazardous reagents, and eliminates the multiple wasteful work-ups in the prior art synthetic pathway to cyclic carbonyl monomers. By reducing waste, eliminating hazardous reagents, and using recyclable materials, the process improves the overall greenness of preparing functionalized cyclic carbonyl monomers.

The precursor compound has the general formula (3):

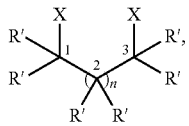

(3)

wherein each X independently represents OH, NHR", $NH_2$, or SH; n is an integer from 0 to 6, wherein when n is 0 carbons labeled 1 and 3 attached to each X group are linked together by a single bond; each R' group independently represents a hydrogen, a halide, a carboxy group, an alkyl group comprising 1 to 20 carbons, an ester group comprising 1 to 20 carbons, an amide group, an aryl group comprising 1 to 20 carbons, an alkoxy group comprising 1 to 20 carbons, or a foregoing R' group substituted with a carboxy group; each R" group independently represents an alkyl group comprising 1 to 20 carbons, an aryl group comprising 1 to 20 carbons, or a foregoing R" group substituted with a carboxy group. The R' and R" groups can further independently comprise a cycloaliphatic ring, an aromatic ring, or a heteroatom such as oxygen, sulfur or nitrogen. At least one of the R' or R" groups independently comprises a carboxy group.

More particularly, the precursor compound has a functional group selected from a 1,2-ethanediol group, 1,3-propanediol group, 1,4-butanediol group, 1,2-ethanediamine group, 1,3-propanediamine group, 1,4-butanediamine group, 2-aminoethanol group, 3-amino-1-propanol group, 4-amino-1-butanol group, 2-mercaptoethanol group, 3-mercapto-1-propanol group, 1-mercapto-2-propanol group, 4-mercapto-1-butanol group, cysteamine group, 1,2-ethanedithiol group, 1,3-propanedithiol group, or combinations thereof. A cyclic urea is derived from any of the above diamines, a cyclic carbamate from any of the above amino-alcohols, a cyclic thiocarbonate from any of the above mercapto-alcohols, a cyclic thiocarbamate from any of the above amino-thiol, and a dithiocarbonate from any of the above dithiols.

The precursor compound can also include isomerically pure forms of the compound or racemic mixtures. The isomerically pure compounds can have an enantiomeric excess of at least 90%, more specifically at least 95%, and even more specifically at least 98%.

The first mixture is agitated at a temperature effective to form a second mixture comprising the first cyclic monomer. The first cyclic monomer comprises a cyclic carbonate, cyclic carbamate, cyclic urea, cyclic thiocarbonate, cyclic thiocarbamate, cyclic dithiocarbonate, or combinations thereof, derived from the two X groups. The first cyclic monomer also comprises an active pentafluorophenyl ester derived from a carboxy group of the precursor compound. The first cyclic monomer is represented by the general formula (4):

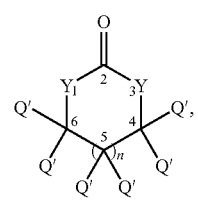

(4)

wherein each Y independently represents O, S, NH or NQ"; and n is an integer from 0 to 6, wherein when n is 0 carbons labeled 4 and 6 are linked together by a single bond; each Q' group independently represents a hydrogen, a halide, a pentafluorophenyl ester group (i.e., the moiety —$CO_2C_6F_5$), an alkyl group comprising 1 to 20 carbons, an ester group other than a pentafluorophenyl ester group comprising 1 to 20 carbons, an amide group comprising 1 to 20 carbons, an aryl group comprising 1 to 20 carbons, an alkoxy group comprising 1 to 20 carbons, or a foregoing Q' group substituted with a pentafluorophenyl ester group. Each Q" group independently represents an alkyl group comprising 1 to 20 carbons or an aryl group comprising 1 to 20 carbons, or a foregoing Q" group substituted with a pentafluorophenyl ester group. At least one of the Q' or Q" groups comprises a pentafluorophenyl ester group. In an embodiment, the compound comprises a single pentafluorophenyl ester group.

Isomerically pure precursor compounds having a hydrogen attached to an asymmetric carbon adjacent to a carboxy group also can be converted to a pentafluorophenyl ester without undergoing significant racemization of the adjacent asymmetric carbon. The esterification conditions are effective in achieving an enantiomeric excess of 80% or more, more specifically of 90%. In an embodiment, the cyclic carbonyl monomer comprises an asymmetric carbon as an (R) isomer, in an enantiomeric excess of greater than 80%, more specifically greater than 90%. In another embodiment, the cyclic carbonyl monomer comprises an asymmetric carbon as an (S) isomer, in an enantiomeric excess greater than 80%, more specifically greater than 90%.

More specific precursor compounds are represented by the general formula (5):

(5)

wherein each X' independently represents OH, NHT", NH$_2$, or SH; each T' can independently represent a hydrogen, a halide, a carboxy group (i.e., the moiety —COOH), an alkyl group comprising 1 to 20 carbons, an ester group comprising 1 to 20 carbons, an amide group, an aryl group comprising 1 to 20 carbons, an alkoxy group comprising 1 to 20 carbons, or a foregoing T' group substituted with a carboxy group; each T" independently represents an alkyl group comprising 1 to 20 carbons, an aryl group comprising 1 to 20 carbons, or a foregoing T" group substituted with a carboxy group. The T' and T" groups can further independently comprise a cycloaliphatic ring, an aromatic ring, or a heteroatom such as oxygen, sulfur or nitrogen. In an embodiment, none of the T' or T" groups comprises a carboxy group. In an embodiment, the T' group attached to carbon labeled 2 in formula (5) is ethyl or methyl, and all other T' groups are hydrogen. In an embodiment, the T' group attached to carbon labeled 2 in formula (5) is ethyl or methyl, carbon labeled 2 in formula (5) is an asymmetric center, and the precursor compound comprises the (R) or (S) isomer in greater than 80% enantiomeric excess.

The corresponding cyclic monomer formed by the precursor compounds of formula (5) have the general formula (6):

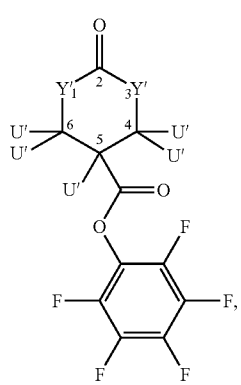
(6)

wherein each Y' independently represents O, S, NH or NU"; each U' group independently represents a hydrogen, a halide, a pentafluorophenyl ester group (—CO$_2$C$_6$F$_5$), an alkyl group comprising 1 to 20 carbons, an ester group comprising 1 to 20 carbons, an amide group comprising 1 to 20 carbons, an aryl group comprising 1 to 20 carbons, an alkoxy group comprising 1 to 20 carbons, or a foregoing U' group substituted with a pentafluorophenyl ester group. Each U" group independently represents an alkyl group comprising 1 to 20 carbons or an aryl group comprising 1 to 20 carbons, or a foregoing U" group substituted with a pentafluorophenyl ester group. In an embodiment, none of the U' or U" groups comprise a pentafluorophenyl ester group. In another embodiment, the U' group attached to the carbon labeled 5 in formula (6) is ethyl or methyl, and all other U' groups are hydrogen. In an embodiment, the U' group attached to carbon labeled 5 in formula (6) is ethyl or methyl, carbon labeled 5 in formula (6) is an asymmetric center, and the cyclic carbonyl compound comprises the (R) or (S) isomer in greater than 80% enantiomeric excess.

As one example, the preparation of first cyclic monomer MTC-PhF$_5$, (7), from the biocompatible precursor compound, bis(2,2-methylol) propionic acid (bis-MPA), (8), is illustrated in Scheme 2.

Scheme 2.

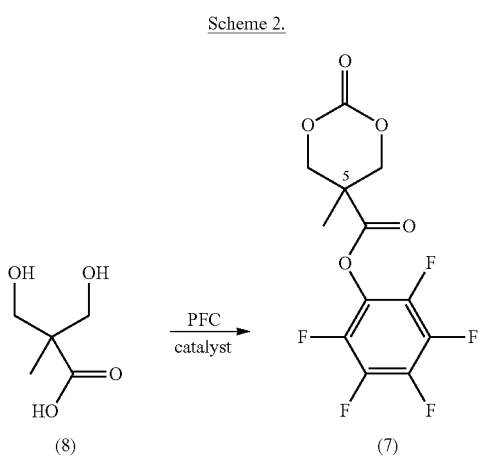

Bis-MPA is converted to MTC-PhF$_5$ in one step under mild conditions. MTC-PhF$_5$ has an active pentafluorophenyl ester (PFP ester) and a methyl group attached to the 5-position of the trimethylene carbonate ring. The reaction can be conducted with about 2 to about 2.5 molar equivalents of PFC, more specifically 2.01 to 2.1 molar equivalents, based on moles of bis-MPA. Generally, 1 mole of pentafluorophenol is consumed to form the PFP ester and 3 moles of pentafluorophenol are produced as a byproduct (not shown) per 2 moles of PFC used. Each theoretical mole of pentafluorophenol byproduct can be recovered in 90% to 100% yield for recycling back to PFC. In an embodiment, the theoretical amount of pentafluorophenol byproduct is quantitatively recovered for recycling back to PFC. MTC-PhF$_5$ is a white, crystalline powder which can be easily handled, manipulated, stored, and shipped, unlike an acyl chloride-functionalized cyclic carbonate.

Also contemplated is the reaction of a carboxy-substituted diamine with PFC to form a cyclic urea comprising an active pentafluorophenyl ester group, the reaction of a carboxy-substituted amino-alcohol with PFC to produce a cyclic carbamate comprising a pentafluorophenyl ester group, the reaction of a carboxy-substituted mercapto-alcohol with PFC to produce a cyclic thiocarbonate comprising a pentafluorophenyl ester group, the reaction of a carboxy-substituted amine-thiol with PFC to produce a cyclic thiocarbamate comprising a pentafluorophenyl ester group, and the reaction of a carboxy-substituted dithiol with PFC to produce a cyclic dithiocarbonate comprising a pentafluorophenyl ester group.

Another challenge in preparing cyclic monomers, for example cyclic carbonates from 1,3-diols, is achieving selective ring closure without polymerization, which depends on the nucleophilicity of the leaving group and the catalyst used. Advantageously, the pentafluorophenol byproduct is a weak nucleophile and does not initiate polymerization. In an embodiment, the disclosed method produces more than 0 to less than 0.5 wt. % of a polymer byproduct derived from the precursor compound, based on the weight of the precursor compound. In another embodiment, the disclosed method produces no detectable polymer byproduct derived from the precursor compound.

The first mixture comprises a catalyst suitably chosen to activate the nucleophilic diol, diamine, amino-alcohol, mercapto-alcohol, amino-thiol, or dithiol functional groups and not the electrophilic PFC carbonyl group. Exemplary catalysts include tertiary amines, for example 1,8-bis(dimethylamino)naphthalene, referred to also as PROTON SPONGE, a trademark of Sigma-Aldrich. Still other catalysts include halide salts of Group I elements, particularly lithium (Li), sodium (Na), potassium (K), rubidium (Rb), cesium (Cs), or francium (Fr). In one embodiment the catalyst is CsF.

The catalyst can be present in an amount of 0.02 to 1.00 moles per mole of the precursor compound, more particularly 0.05 to 0.50 moles per mole of the precursor compound, and even more particularly 0.15 to 0.25 moles per mole of the precursor compound.

The first mixture optionally includes a solvent such as tetrahydrofuran, methylene chloride, chloroform, acetone, methyl ethyl ketone, acetonitrile, ethyl acetate, butyl acetate, benzene, toluene, xylene, hexane, petroleum ethers, 1,4-dioxane, diethyl ether, ethylene glycol dimethyl ether, or combinations thereof. When a solvent is present, the concentration of precursor compound in the solvent can be from about 0.01 to about 10 moles per liter, more typically about 0.02 to 0.8 moles per liter, more specifically 0.1 to 0.6 moles per liter, or most specifically 0.15 to 0.25 moles per liter. In one embodiment, the reaction mixture consists of the precursor compound, PFC, a catalyst and a solvent. In one embodiment the solvent is anhydrous.

The method (Method 1) includes agitating the first mixture at a temperature suitable for converting the precursor compound to the first cyclic monomer. The temperature can be from −20° C. to 100° C., 0° C. to 80° C., 10° C. to 50° C., or more specifically ambient or room temperature, typically 17° C. to 30° C. Optionally, the reaction mixture is agitated under an inert atmosphere. In one embodiment, the temperature is ambient temperature.

Agitation of the first mixture can be conducted for 1 hour to 120 hours, 5 hours to 48 hours, and more specifically 12 hours to 36 hours. In one embodiment, agitation is conducted for 15 to 24 hours at ambient temperature.

The second mixture comprises the first cyclic carbonyl monomer comprising the pentafluorophenyl ester and pentafluorophenol byproduct. The cyclic monomer can be isolated using any known method of purification, including distillation, chromatography, extraction, and precipitation. In one embodiment, the cyclic monomer is purified by selective precipitation of the pentafluorophenol byproduct or the cyclic monomer from the second mixture. In one variation on selective precipitation, the reaction mixture comprises a first solvent in which the precursor compound, PFC, cyclic monomer and pentafluorophenol byproduct are highly soluble. Upon completion of the reaction to form the cyclic monomer, the first solvent is removed by, for example, vacuum distillation, followed by addition of a second solvent suitably chosen to selectively precipitate the pentafluorophenol byproduct or the cyclic monomer. In another variation, the first solvent can be selected to facilitate precipitation of the cyclic monomer or the pentafluorophenol byproduct from the second mixture as the reaction proceeds.

The method can further comprise the step of recovering the pentafluorophenol byproduct for recycling. For reactions in which one mole of pentafluorophenol is consumed in making the pentafluorophenyl ester, the yield of recovered pentafluorophenol byproduct from the second mixture is about 80% to 100%, more specifically 90% to 100%, based on the theoretical amount of pentafluorophenol byproduct formed. In an embodiment, the theoretical amount of pentafluorophenol byproduct is quantitatively recovered for recycling back to PFC.

Method 2. Functionalization of the First Cyclic Monomer.

Also disclosed is a mild method (Method 2) of deriving a second cyclic carbonyl monomer from the first cyclic carbonyl monomer, by converting the pentafluorophenyl ester (PFP ester) into a different ester, an amide, or a thioester, without altering the cyclic carbonyl moiety of the first cyclic carbonyl monomer. Typically, a catalyst is also used in Method 2, although it is not required, such as in the reaction of a PFP ester with a primary amine (Example 3).

More specifically, a method of deriving a second cyclic carbonyl monomer from the first cyclic carbonyl monomer comprises forming a first mixture comprising a first cyclic carbonyl monomer (e.g., MTC-PhF$_5$) comprising a pentafluorophenyl ester group and a cyclic carbonyl group selected from cyclic carbonate, cyclic carbamate, cyclic urea, cyclic thiocarbonate, cyclic thiocarbamate, cyclic dithiocarbonate, and combinations thereof; an optional solvent; an optional catalyst; and a nucleophile comprising 1 to 30 carbons comprising an alcohol other than pentafluorophenol, an amine, a thiol, or combinations thereof; and agitating the first mixture to form a second mixture comprising the second cyclic carbonyl monomer and a pentafluorophenol byproduct. The second cyclic carbonyl monomer comprises an ester, an amide, or a thioester group derived from the pentafluorophenyl ester. In an embodiment, the first cyclic carbonyl monomer has the general formula (4) as described above. In another embodiment, the first cyclic monomer has the general formula (6), as described above. In another embodiment, the first cyclic monomer comprises a single pentafluorophenyl ester group.

In an even more specific embodiment, the first cyclic monomer is MTC-PhF$_5$. As an example, MTC-PhF$_5$ can be converted to the corresponding 2,2,2-trifluoroethyl ester, MTC-TFE, (22), according to Scheme 3.

Scheme 3.

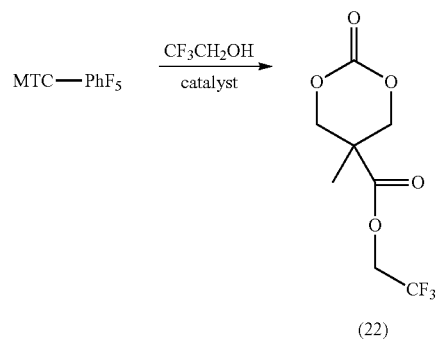

(22)

Non-limiting examples of other alcohols capable of transesterifying the PFP ester of MTC-PhF$_5$ without altering the cyclic carbonate group include:

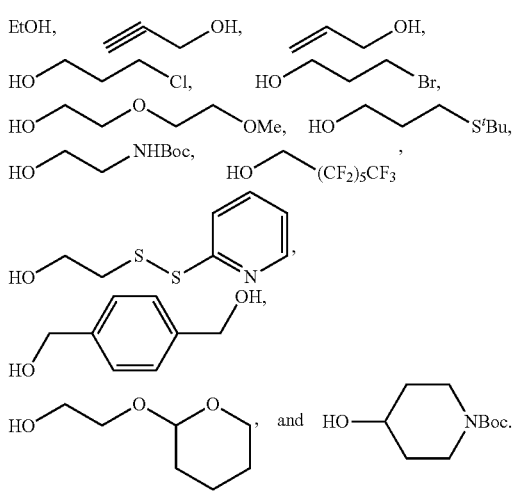

Non-limiting examples of amines capable of reacting with the PFP ester of MTC-PhF$_5$ to form an amide without altering the cyclic carbonate group include:

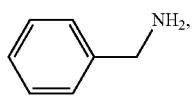

dimethylamine, and
isopropylamine.

Non-limiting examples of thiols capable of reacting with the PFP ester to form a thioester without altering the cyclic carbonyl group include: (see Part II)

The alcohol, amine, thiol or combinations thereof may be attached to larger structures including oligomers, polymers, biomacromolecules, particles, and functionalized surfaces, Non-limiting polymeric scaffolds include linear, branched, hyperbranched, cyclic, dendrimeric, block, graft, star, and other known polymer structures. Non-limiting biomacromolecules include proteins, DNA, RNA, lipids, phospholipids. Non-limiting particles may have dimensions ranging from less than 1 nanometer to hundreds of micrometers. Non-limiting large particles include silica, alumina, and polymeric resins such as those commonly used for chromatography and functionalized polymeric beads such as those commonly used for solid-phase synthesis. Non-limiting nanoparticles include both organic and inorganic nanoparticles including those functionalized with ligands or stabilizing polymers. Non-limiting organic nanoparticles may include crosslinked polymeric nanoparticles, dendrimers, and star polymers. Non-limiting inorganic nanoparticles include metallic nanoparticles (e.g., gold, silver, other transition metals, and Group 13 to Group 16 metals of the periodic table), oxide nanoparticles (e.g., alumina, silica, hafnia, zirconia, zinc oxide), nitride nanoparticles (e.g., titanium nitride, gallium nitride), sulfide nanoparticles (e.g., zinc sulfide) semiconducting nanoparticles (e.g., cadmium selenide). Non-limiting functionalized surfaces include surfaces functionalized with self-assembled monolayers.

Generally, the first mixture of Method 2 is agitated at a temperature of −78° C. to 100° C., more specifically −20° C. to 50° C., and even more specifically −10° C. to 30° C. to form the second cyclic monomer. In an embodiment, agitation to convert the PFP ester to a different ester, amide or thiol is conducted at ambient temperature, or 17° C. to 30° C. The first mixture is agitated for a period of about 1 hour to about 48 hours, more particularly about 20 to 30 hours at the reaction temperature.

Typically, a solvent is used in Method 2, though not required. Depending on the solvent, the pentafluorophenol byproduct can in some instances precipitate directly from the reaction mixture as it is formed. Generally, however, the second mixture is concentrated under vacuum and the resulting residue is then treated with a second solvent in which the pentafluorophenol byproduct is not soluble, such as methylene chloride. The pentafluorophenol byproduct can then be filtered and recovered for recycling back to PFC. In an embodiment, 90% to 100% of the theoretical pentafluorophenol byproduct is recovered for recycling back to PFC. The derived second cyclic monomer can be isolated by washing the organic filtrate with a base such as sodium bicarbonate solution, drying the filtrate with a drying agent such as magnesium sulfate, and evaporation of the second solvent under vacuum. In this manner the second cyclic monomer can be obtained in a yield of about 50% to about 100%, more particularly about 70% to 100%, even more particularly about 80% to 100%.

The optional catalyst of Method 2 can be selected from typical catalysts for transesterifications, conversions of esters to amides, or conversion of esters to thioesters. These include organic catalysts and inorganic catalysts, in particular the above described catalysts, and most specifically cesium fluoride. When used in Method 2, the catalyst can be present in an amount of 0.02 to 1.00 moles per mole of the first cyclic monomer, more particularly 0.05 to 0.50 moles per mole of the first cyclic monomer, and even more particularly 0.15 to 0.25 moles per mole of the first cyclic monomer.

In an additional embodiment, the Methods 1 and 2 are performed step-wise in a single reaction vessel, without an intermediate step to isolate the first cyclic carbonyl monomer.

The above-described methods provide a controlled process for introducing a wide range of functionality and connectivity into cyclic monomers for ring-opening polymerizations. As stated above, the cyclic monomers (first and/or second cyclic monomers) can be formed in isomerically pure form, or as racemic mixtures.

Method 3. Ring Opening Polymerization of the First Cyclic Monomer.

Further disclosed are polymers obtained by ring opening polymerization of the above described cyclic monomers, including the first and second cyclic monomers. The following description of ROP methods applies to all cyclic monomers described herein.

The above-described cyclic monomers can undergo ring-opening polymerization (ROP) to form biodegradable polymers of different tacticities. Atactic, syndiotactic and isotactic forms of the polymers can be produced that depend on the cyclic monomer(s), its isomeric purity, and the polymerization conditions.

A method (Method 3) of ring-opening polymerization comprises forming a first mixture comprising the cyclic monomer, a catalyst, an initiator, and an optional solvent. The first mixture is then heated and agitated to effect polymerization of the cyclic monomer, forming a second mixture containing the biodegradable polymer product.

The ring opening polymerization is generally conducted in a reactor under inert atmosphere such as nitrogen or argon. The polymerization can be performed by solution polymerization in an inactive solvent such as benzene, toluene, xylene, cyclohexane, n-hexane, dioxane, chloroform and dichloroethane, or by bulk polymerization. The ROP reaction temperature can be from 20° to 250° C. Generally, the reaction mixture is heated at atmospheric pressure for 0.5 to 72 hours to effect polymerization. Subsequently, additional cyclic monomer and catalyst can be added to the second mixture to effect block polymerization if desired.

Exemplary ROP catalysts include tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; tertiary amines such as triallylamine, triethylamine, tri-n-octylamine and benzyldimethylamine; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate. More particularly, the catalyst is zirconium octanoate, tetraalkoxy zirconium or a trialkoxy aluminum compound.

Other ROP catalysts include metal-free organocatalysts that can provide a platform to polymers having controlled, predictable molecular weights and narrow polydispersities. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, and guanidines.

The ROP reaction mixture comprises at least one catalyst and, when appropriate, several catalysts together. The ROP catalyst is added in a proportion of 1/20 to 1/40,000 moles relative to the cyclic monomers, and preferably of 1/1,000 to 1/20,000 moles.

The ROP reaction mixture also comprises an initiator. Initiators generally include nucleophiles such as alcohols, amines and thiols. The initiator can be monofunctional, difunctional or multifunctional such as dendritic, polymeric or related architectures. Monofunctional initiators can include nucleophiles with protected functional groups that include thiols, amines, acids and alcohols. A typical initiator is phenol or benzyl alcohol.

Well-known apparatuses can be used for performing the ROP polymerization. Examples of tower type reaction apparatus include a reaction vessel comprising helical ribbon wings and transformational spiral baffles. Examples of sideways type reaction apparatus include a sideways type one- or twin-shaft kneader comprising agitation shafts which have a row of transformational wings and arranged in parallel to each other. In addition, the reaction apparatus may be either a batch type or a continuous one. Examples of the batch type apparatus include Max Blend Type Reactor (made by Sumitomo Heavy Machine Co., Ltd.), Super Blend Type Reactor (made by Sumitomo Heavy Machine Co., Ltd.), ReverseCone Ribbon Wing Type Reactor (made by Mitsubishi Heavy Industries Co., Ltd.), Spiral Lattice-Shaped Wing Type Reactor (Hitachi Seisakusho Co., Ltd.). Examples of the continuous type apparatus include BIVOLAK (made by Sumitomo Heavy Machine Co., Ltd.), Hitachi Spectacles-Shaped Polymerization Machine (made by Hitachi Seisakusho Co., Ltd.), Hitachi Lattice-Shaped Polymerization Machine (made by Hitachi Seisakusho Co., Ltd.), Self-Cleaning Type Reactor (made by Mitsubishi Heavy Industries Co., Ltd.), Twin-Shaft Sideways Type Reactor (made by Mitsubishi Heavy Industries Co., Ltd.), KRC Kneader (made by Kurimoto Co., Ltd.), TEX-K (The Japan Steel Work Co., Ltd.) and single- or twin-screw extruders widely used for extrusion molding of plastics and devolatilization treatment.

The biodegradeable ROP product can be a homopolymer, copolymer, or block copolymer. The biodegradable polymer can have a number-average molecular weight of usually 1,000 to 200,000, more particularly 2,000 to 100,000, and still more particularly 5,000 to 80,000.

The biodegradable polymer product of the ROP polymerization can be applied to conventional molding methods such as compression molding, extrusion molding, injection molding, hollow molding and vacuum molding, and can be converted to molded articles such as various parts, receptacles, materials, tools, films, sheets and fibers. A molding composition can be prepared comprising the biodegradable polymer and various additives, including for example nucleating agents, pigments, dyes, heat-resisting agents, antioxidants, weather-resisting agents, lubricants, antistatic agents, stabilizers, fillers, strengthened materials, fire retardants, plasticizers, and other polymers. Generally, the molding compositions comprise 30 wt. % to 100 wt. % or more of the biodegradable polymer based on total weight of the molding composition. More particularly, the molding composition comprises 50 wt. % to 100 wt. % of the biodegradable polymer.

The biodegradable polymer product of the ROP polymerization can be formed into free-standing or supported films by known methods. Non-limiting methods to form supported films include dip coating, spin coating, spray coating, doctor blading. Generally, such coating compositions comprise 0.01 wt. % to 90 wt. % of the biodegradable polymer based on total weight of the coating composition. More particularly, the molding composition comprises 1 wt. % to 50 wt. % of the biodegradable polymer based on total weight of the coating composition. The coating compositions generally also include a suitable solvent necessary to dissolve the biodegradable polymer product.

The coating compositions can further include other additives selected so as to optimize desirable properties, such as optical, mechanical, and/or aging properties of the films. Non-limiting examples of additives include surfactants, ultraviolet light absorbing dyes, heat stabilizers, visible light absorbing dyes, quenchers, particulate fillers, and flame retardants. Combinations of additives can also be employed.

The following Example 1 illustrates the method of making a first cyclic carbonyl monomer, MTC-PhF$_5$. Examples 2-15 illustrate Method 2, displacing the PFP ester of MTC-PhF$_5$ to form a variety of second cyclic monomers comprising different ester or amide groups.

EXAMPLES

Example 1

Preparation of 5-methyl-5-pentafluorophenyloxycarboxyl-1,3-dioxane-2-one, MTC-PhF$_5$, (7)

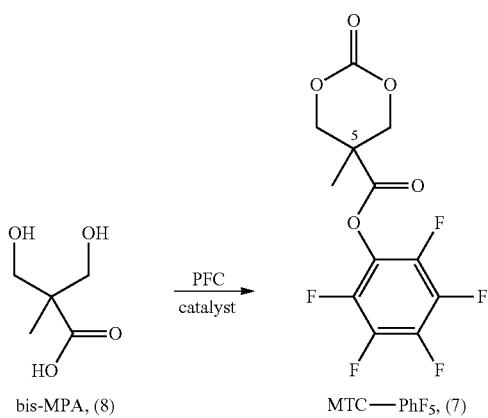

A 100 mL round bottom flask was charged with bis-MPA, (7), (5.00 g, 37 mmol), bis-(pentafluorophenol) carbonate (PFC, 31.00 g, 78 mmol), and CsF (2.5 g, 16.4 mmol rinsed in with 70 mls of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}$F NMR of pentafluorophenol and a single peak in the GCMS with a mass of 184. The filtrate was extracted with sodium bicarbonate, water and was dried with MgSO$_4$. The solvent was evaporated in vacuo and the product was recrystallized (ethylacetate/hexane mixture) to give MTC-PhF$_5$, (8), as a white crystalline powder (GCMS single peak with mass of 326 g/mol, calculated molecular weight for C$_{12}$H$_7$F$_5$O$_5$ (326 g/mol) consistent with the assigned structure. FIG. 1 shows $^1$H NMR and $^{19}$F NMR spectrographs of MTC-PhF$_5$. $^1$H-NMR (400 MHz in CDCl$_3$): δ 4.85 (d, J=10.8 Hz, 2H, CH$_a$H$_b$), 4.85 (d, J=10.8 Hz, 2H, CH$_a$H$_b$), 1.55 (s, 3H, CCH$_3$).

Example 2

Preparation of MTC-Et, (9)

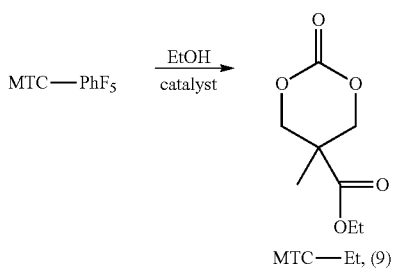

Figure 2:
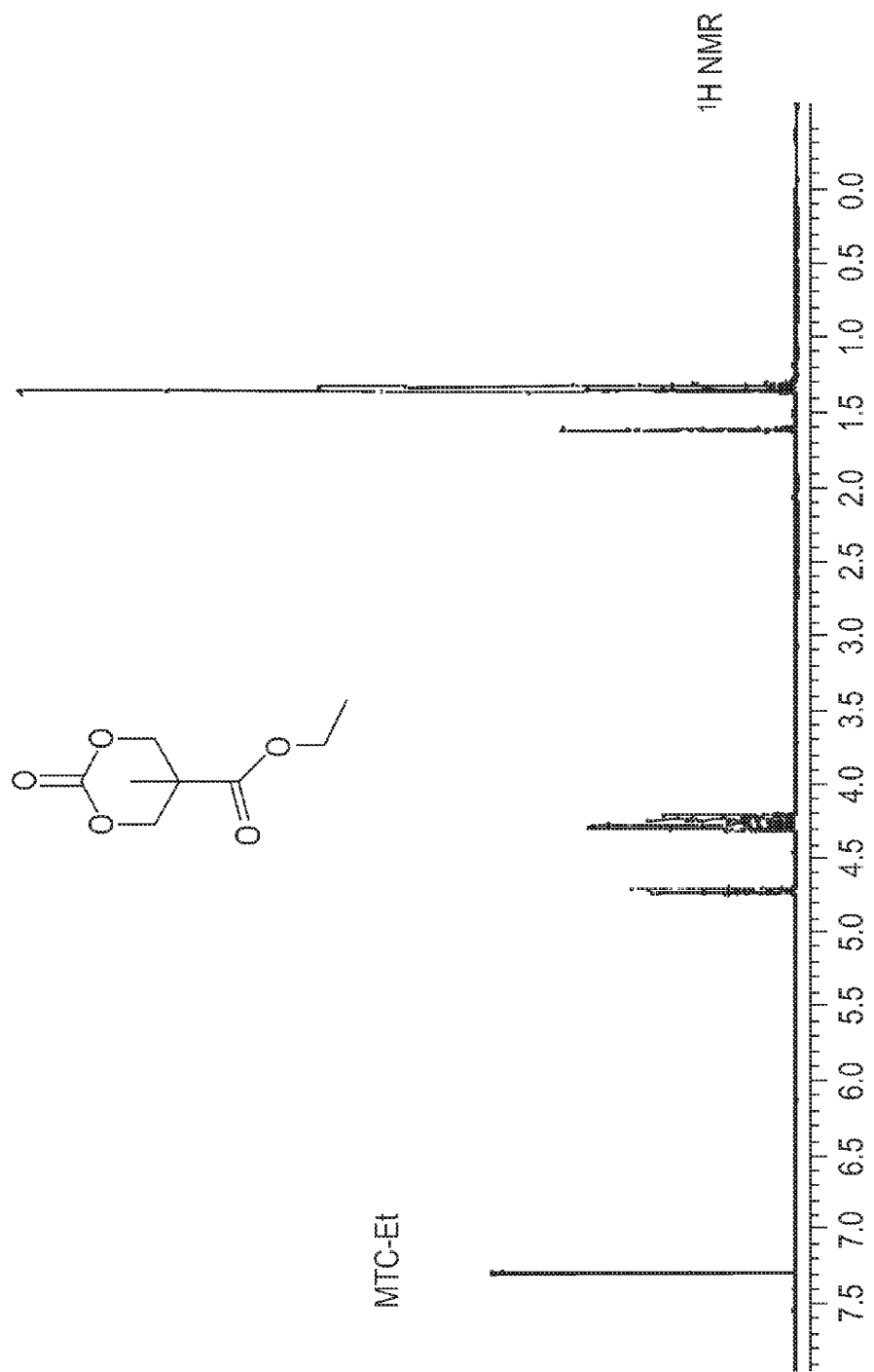

A round bottom flask was charged with a THF solution of MTC-PhF$_5$, ethanol and CsF. The reaction was allowed to stir overnight, after which NMR analysis on the crude product showed about 95% conversion to the ethyl ester carbonate. The solvent was removed and the mixture was re-dissolved in methylene chloride. The solution was allowed to stand for approximately 10 min, at which time the pentafluorophenol byproduct precipitated and could be quantitatively recovered. This byproduct showed the characteristic 3 peaks in the $^{19}$F NMR of pentafluorophenol and a single peak in the GCMS with a mass of 184 g/mol. The organic phase was treated with saturated NaHCO$_3$ (200 mL), brine (200 mL), and water (200 mL), and dried over MgSO$_4$. The solvent was evaporated in vacuo, and the residue was recrystallized from ethyl acetate to give white crystals (56% yield). GCMS showed a single peak with mass of 189 g/mol, calculated molecular weight for C$_8$H$_{12}$O$_5$ (188 g/mol) consistent with the assigned structure (FIG. 2). $^1$H NMR: δ 4.68 (d, 2H, CH$_2$OCOO), 4.25 (q, 1H, OCH$_2$CH$_3$), 4.19 (d, 2H, CH$_2$OCOO), 1.32 (s, 3H, CH$_3$), 1.29 (t, 3H, CH$_3$CH$_2$O). $^{13}$C NMR: δ 171.0, 147.5, 72.9, 62.1, 39.9, 17.3, 13.8.

Example 3

Preparation of MTC-BnAmine, (10)

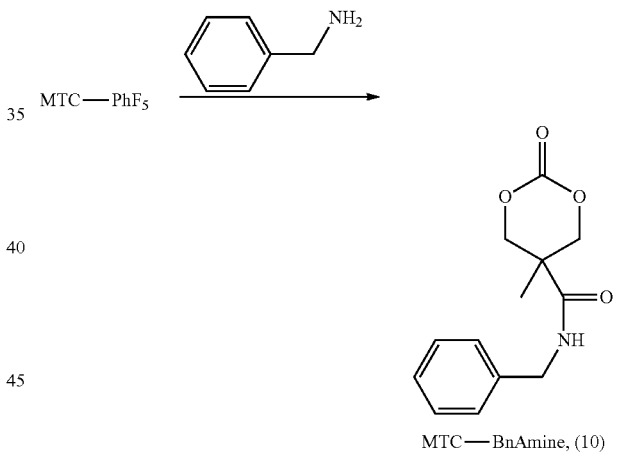

Figure 3:
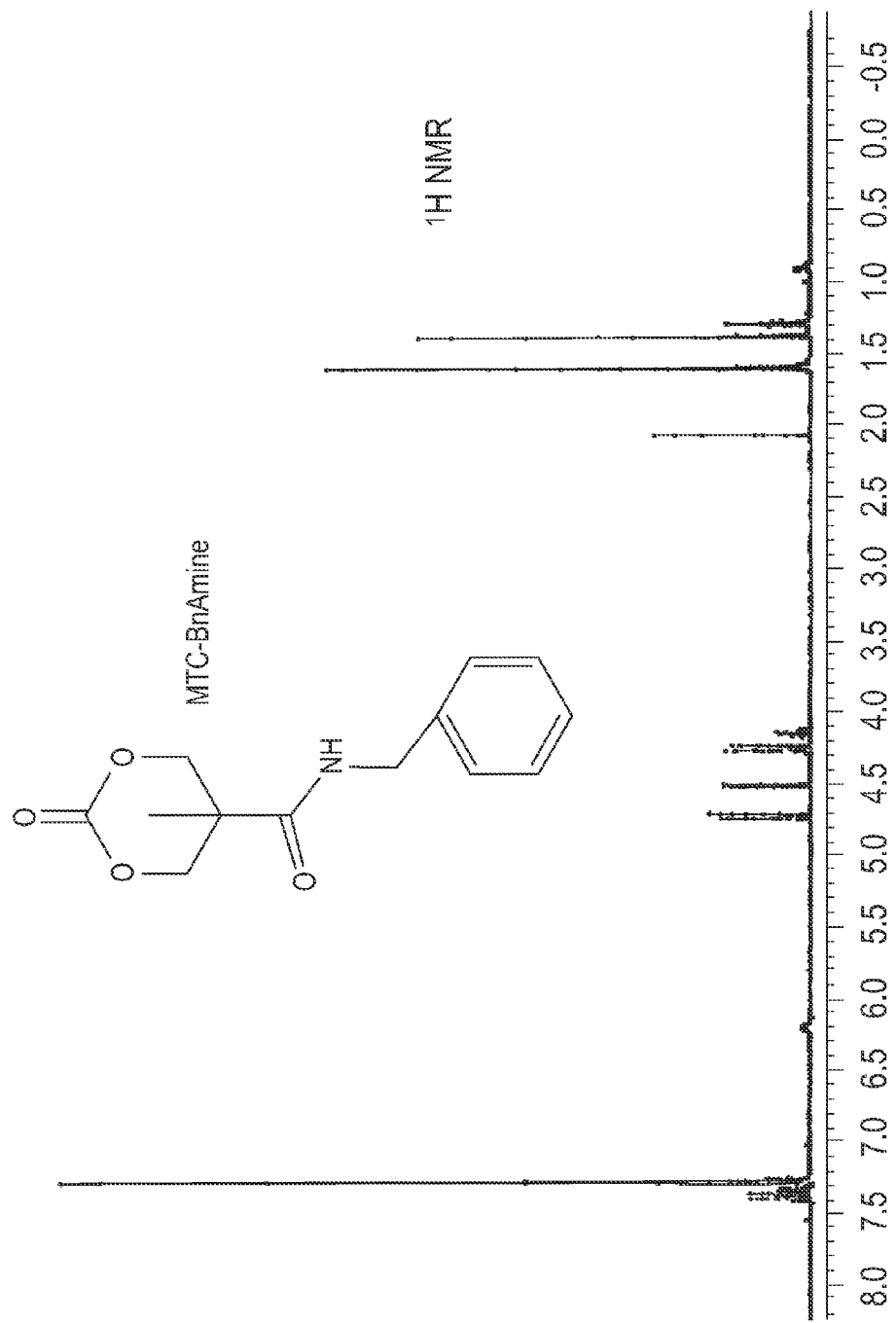

To a THF solution of bis-MPA carbonate (0.25 g, 0.76 mmol), benzyl amine (0.08 g, 0.76 mmol) dissolved in THF was added dropwise at 0° C. $^1$H NMR after 5 minutes reaction time showed 60% conversion at 0° C. The reaction was allowed to proceed overnight and slowly warm to room temperature. The $^1$H NMR of the reaction mixture showed quantitative conversion of the ester to the amide with no residual benzyl amine and no side reactions. The reaction mixture was concentrated and dissolved in methylene chloride, a non-solvent for the pentafluorophenol, which was filtered. The product was concentrated and crystallized from ethyl acetate/hexane mixtures. Yield: 70%. GCMS showed a single peak with mass of 249 g/mol, calculated molecular weight for C$_{13}$H$_{15}$NO$_5$ (249 g/mol) consistent with the assigned structure (FIG. 3). $^1$H-NMR (400 MHz in CDCl$_3$): δ 7.30-7.45 (m, 5H, ArH), 4.70 (d, J=10.8 Hz, 2H, CH$_a$H$_b$), 4.50 (d, 2H, ArCH$_2$N), 1.35 (s, 3H, CCH$_3$).

Example 4

Preparation of MTC-OCH₂CCH, (11)

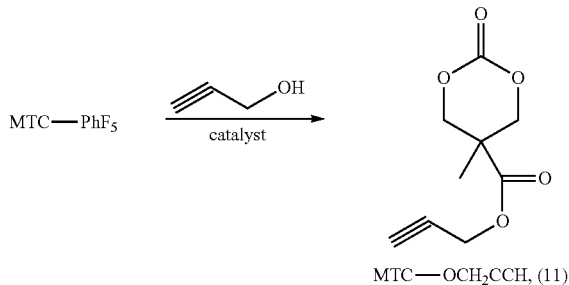

Figure 4:
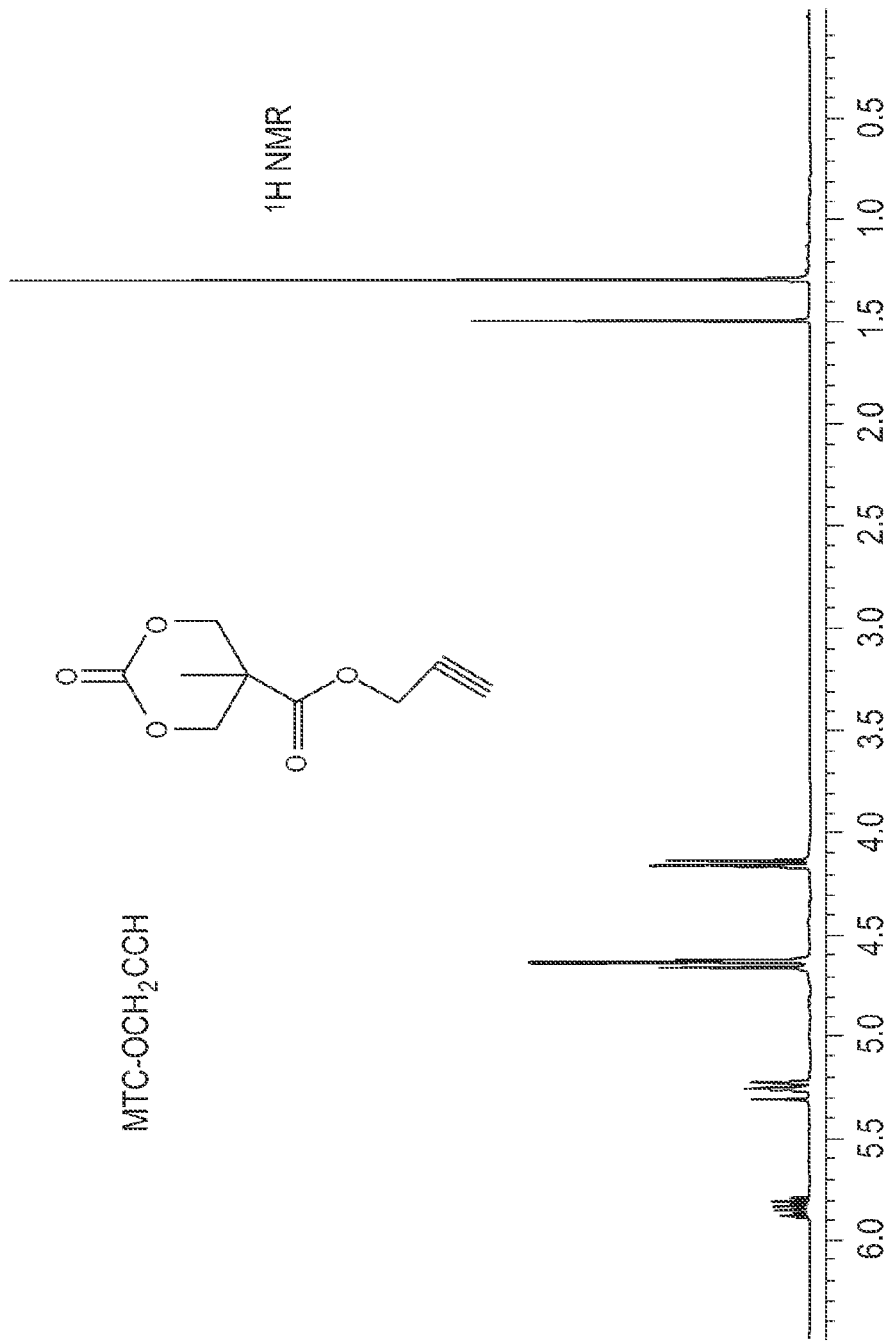

A round bottom flask was charged with MTC-PhF$_5$ (0.70 g, 0.0021 mol), CsF (0.10 g, 0.66 mmol) and propargyl alcohol (0.29 g, 0.0021 mol), rinsed in with 10 mL of THF. The mixture was stirred for 24 hours at ambient temperature, filtered to remove pentafluorophenol, and the solvent was evaporated in vacuo. The reaction mixture was dissolved in methylene chloride, allowed to stand for about 30 min, and filtered to remove additional pentafluorophenol byproduct that was quantitatively recovered. This byproduct showed the characteristic 3 peaks in the $^{19}$F NMR of pentafluorophenol and a single peak in the GCMS with a mass of 184 g/mol. The organic phase was then treated with saturated NaHCO$_3$ (200 mL), brine (200 mL), water (200 mL), dried over MgSO$_4$ and was concentrated. The crude product was purified by column chromatography (silica, 1:1 ethyl acetate/hexanes) to a clear oil that slowly solidified to a white solid, m.p. 70 to 72° C. Yield: (65%). GCMS showed a single peak with mass of 198 g/mol, calculated molecular weight for C$_9$H$_{10}$O$_5$ (198 g/mol) consistent with the assigned structure (FIG. 4). $^1$H-NMR: δ 4.80 (d, J=2.4 Hz, 2H, OCH$_2$CCH), 4.72 (d, J=10.8 Hz, 2H, CH$_a$H$_b$), 4.24 (d, J=10.8 Hz, 2H, CH$_a$H$_b$), 2.55 (t, J=2.4 Hz, 1H, OCH$_2$CCH), 1.38 (s, 3H, CCH$_3$). $^{13}$C-NMR: δ 170.8, 147.7, 76.8, 76.4, 73.2, 53.9, 40.6, 17.8.

Example 5

Preparation of MTC-OCH₂CH₂CH₂Br, (12)

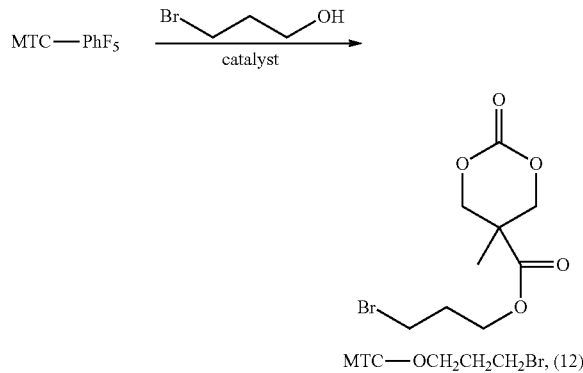

Figure 5:
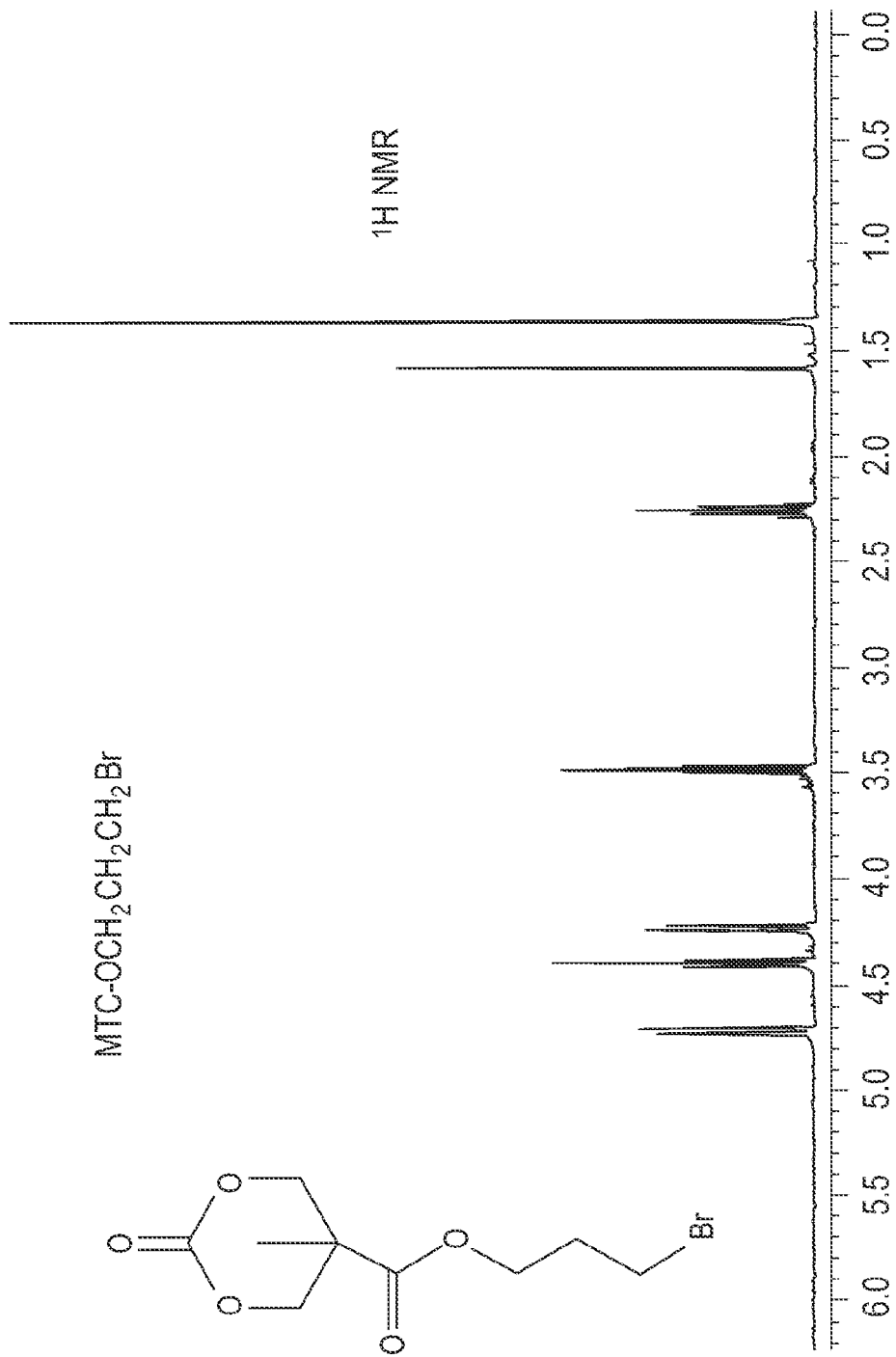

A round bottom flask was charged with MTC-PhF$_5$ (0.7 g, 0.0021 mol), CsF (0.10 g, 0.66 mmol) and 3-bromopropanol (0.298 g, 0.0021 mol), rinsed in with 10 mL of THF. The reaction mixture was stirred for 24 hours, filtered to remove pentafluorophenol byproduct, and the solvent was evaporated in vacuo. The reaction mixture was dissolved in methylene chloride, allowed to stand for about 30 min, and filtered to remove more precipitated pentafluorophenol by-product. The pentafluorophenol byproduct was quantitatively recovered. This byproduct showed the characteristic 3 peaks in the $^{19}$F NMR of pentafluorophenol and a single peak in the GCMS with a mass of 184 g/mol. The organic phase was then treated with saturated NaHCO$_3$ (200 mL), brine (200 mL), water (200 mL), dried over MgSO$_4$ and concentrated. The crude product was purified by column chromatography (silica, 1:1 ethyl acetate/hexanes) to a clear, colorless oil. Yield: 70%. GCMS showed a single peak with mass of 281 g/mol, calculated molecular weight for C$_9$H$_{13}$O$_5$ (280 g/mol) consistent with the assigned structure (FIG. 5). $^1$H-NMR: δ 4.70 (d, J=10.8 Hz, 2H, CH$_a$H$_b$), 4.40 (t, J=6.0 Hz, 2H, OCH$_2$CH$_2$), 4.22 (d, J=10.8 Hz, 2H, CH$_a$H$_b$), 3.50 (t, J=6.0 Hz, 2H, CH$_2$Cl), 2.08 (quip, J=6.0 Hz, 2H, CH$_2$CH$_2$CH$_2$), 1.27 (s, 3H, CCH$_3$).

Example 6

Preparation of MTC-OCH₂CHCH₂, (13)

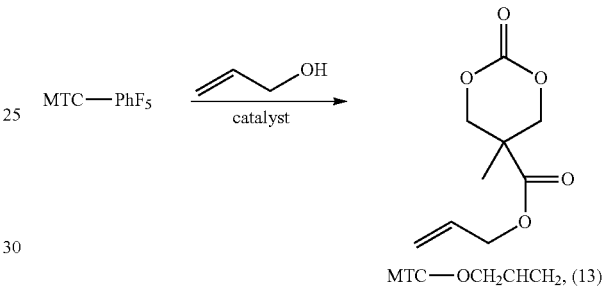

Figure 6:
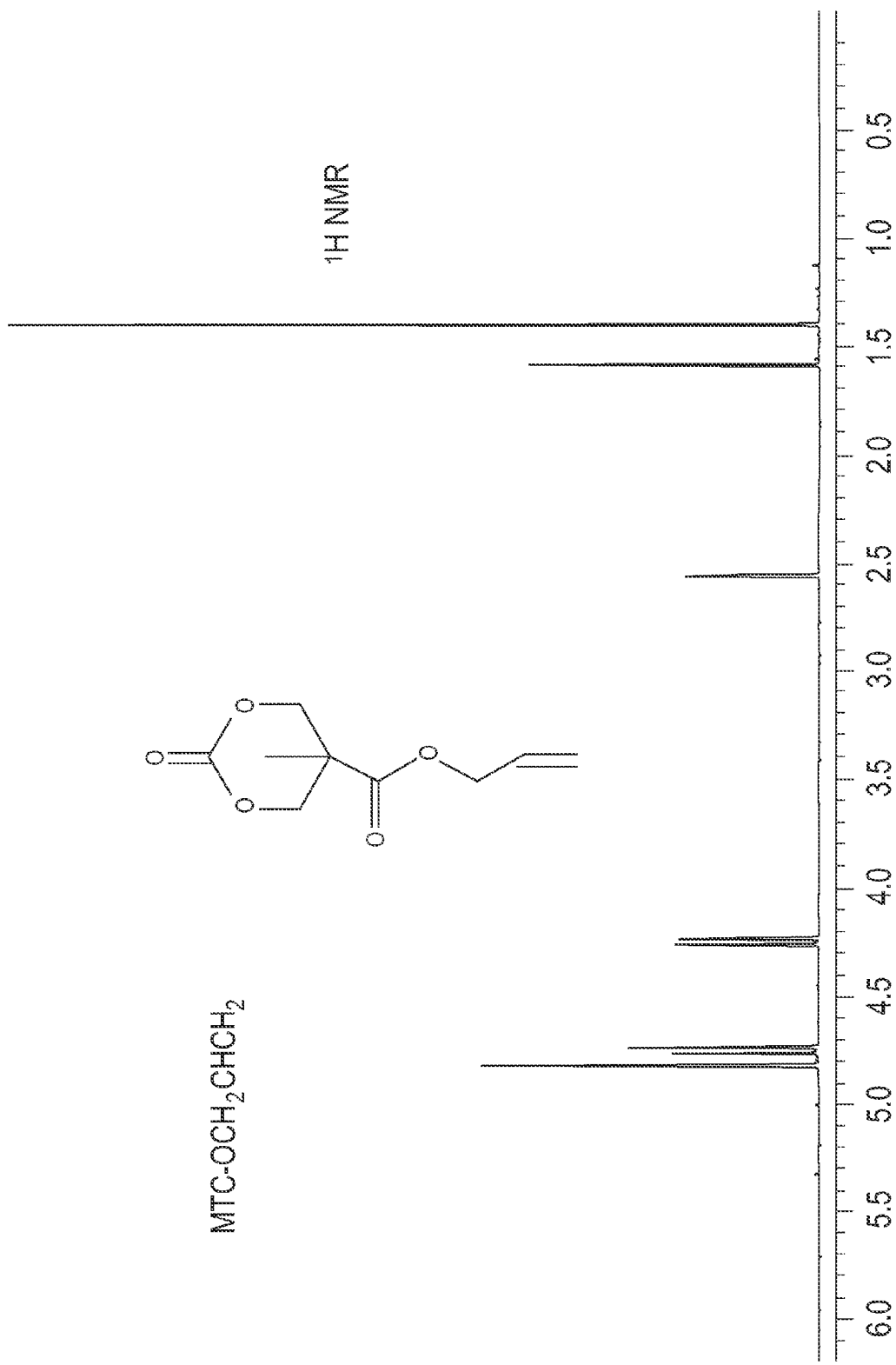

A round bottom flask was charged with MTC-PhF$_5$ (1.18 g, 0.0036 mol), CsF (0.35 g, 0.0023 mol) and allyl alcohol (0.219 g, 0.00037 mol), rinsed in with 10 mL of THF. The mixture was stirred for 24 hours, filtered to remove pentafluorophenol byproduct, and the solvent was evaporated in vacuo. The crude product was dissolved in methylene chloride, and the solution was allowed to stand for about 30 min, during which time more pentafluorophenol byproduct precipitated. The pentafluorophenol byproduct was filtered, and was quantitatively recovered. The byproduct showed the characteristic 3 peaks in the $^{19}$F NMR of pentafluorophenol and a single peak in the GCMS with a mass of 184 g/mol. The organic phase was treated sequentially with saturated NaHCO$_3$ (200 mL), brine (200 mL), and water (200 mL), then dried over MgSO$_4$ and concentrated. Purification of the product by column chromatography (silica, 1:1 ethyl acetate/hexanes) provided the desired material as an oil that slowly solidified to a white solid, m.p. 64° C. to 66° C. Yield: 65%. GCMS showed a single peak with mass of 201 g/mol, calculated molecular weight for C$_9$H$_{12}$O$_5$ (200 g/mol) consistent with the assigned structure (FIG. 6). $^1$H-NMR: δ 5.80-5.90 (m, 1H CH), 4.65 (t, 2H, COOCH$_2$), 4.60 (d, J=10.8 Hz, 2H, CH$_a$H$_b$), 4.24 (d, J=10.8 Hz, 2H, CH$_a$H$_b$), 1.38 (s, 3H, CCH$_3$).

Example 7

Preparation of MTC-OCH₂CH₂SS(2-Py), (14)

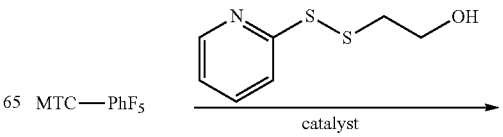

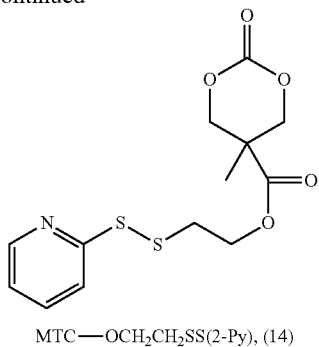

MTC—OCH$_2$CH$_2$SS(2-Py), (14)

Figure 7:
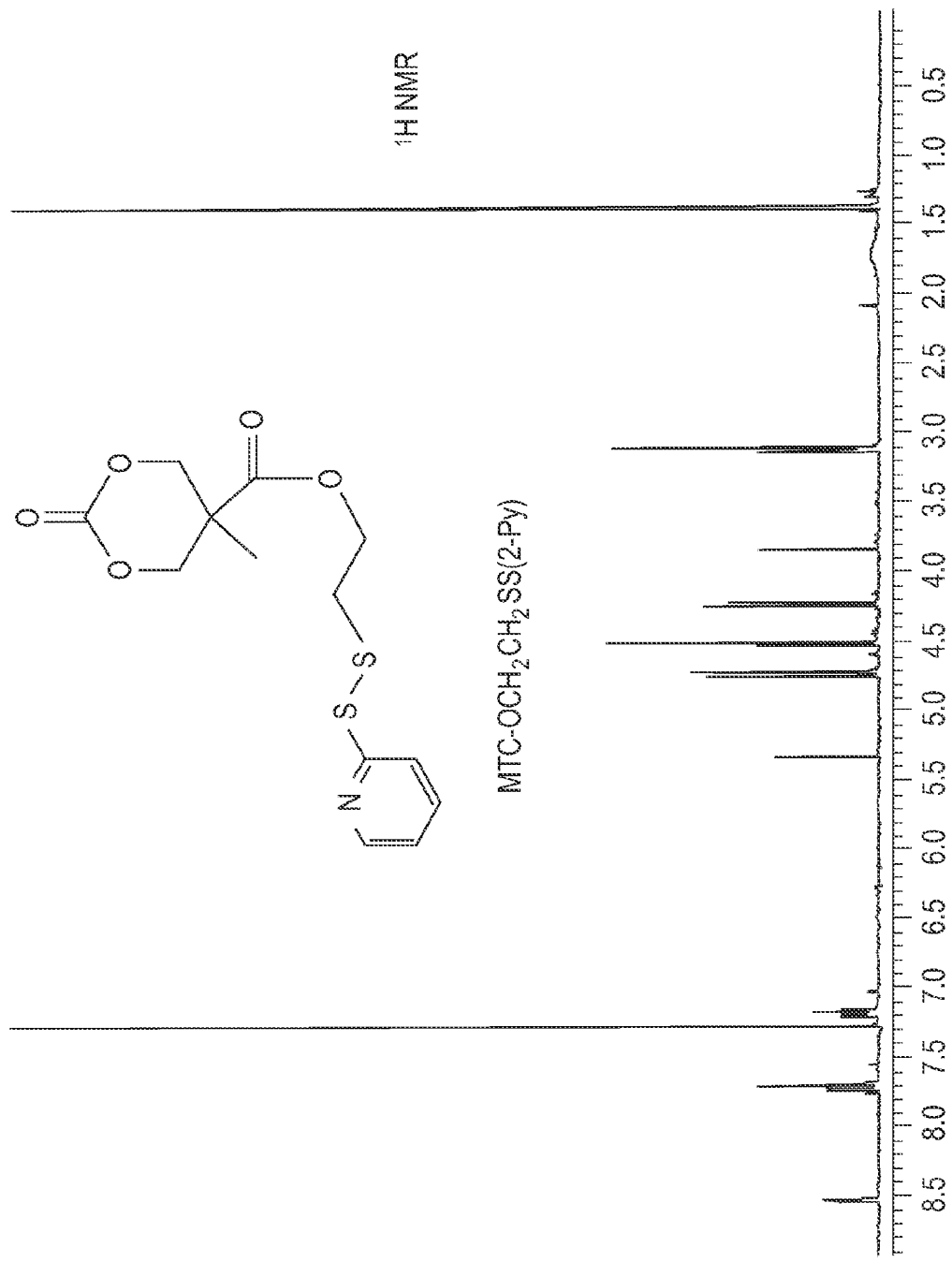

A round bottom flask was charged with MTC-PhF$_5$ (0.25 g, 0.0007 mol), CsF (0.05 g, 0.33 mmol) and S-2-pyridyl-S'-2-hydroxyethyl disulfide (0.15 g, 0.0008 mol), rinsed in with 10 mL of THF. The mixture was stirred for 24 hours and filtered to remove pentafluorophenol byproduct. The solvent was then evaporated in vacuo. The reaction mixture was dissolved in methylene chloride, allowed to stand about 30 minutes, and additional precipitated pentafluorophenol byproduct was filtered. The pentafluorophenol byproduct was quantitatively recovered. This byproduct showed the characteristic 3 peaks in the $^{19}$F NMR of pentafluorophenol and a single peak in the GCMS with a mass of 184 g/mol. The organic phase was treated with saturated NaHCO$_3$ (200 mL), brine (200 mL), water (200 mL), dried over MgSO$_4$ and concentrated. The crude product was purified by column chromatography (silica, 1:1 ethyl acetate/hexanes) to an oil that slowly solidified to a white solid, mp 64-65° C. Yield: 65%. GCMS showed a single peak with mass of 220 g/mol, consistent with the loss of pyridyl thione, calculated molecular weight for C$_{13}$H$_{15}$NO$_5$S$_2$ (329 g/mol) consistent with the assigned structure (FIG. 7). $^1$H-NMR: δ 8.49 (m, 1H, ArH), 7.67 (m, 2H, ArH), 7.14 (m, 1H, ArH), 4.70 (d, J=10.8 Hz, 2H, CH$_a$H$_b$), 4.49 (t, J=6.4 Hz, 2H, COOCH$_2$), 4.21 (d, J=10.8 Hz, 2H, CH$_a$H$_b$), 3.08 (t, J=6.4 Hz, 2H, SCH$_2$), 1.35 (s, 3H, CCH$_3$). $^{13}$C-NMR: δ 171.3, 159.5, 150.2, 147.8, 137.6, 121.5, 120.4, 73.3, 64.1, 40.7, 37.3, 18.0.

Example 8

Preparation of MTC-OCH$_2$CH$_2$OTHP, (15)

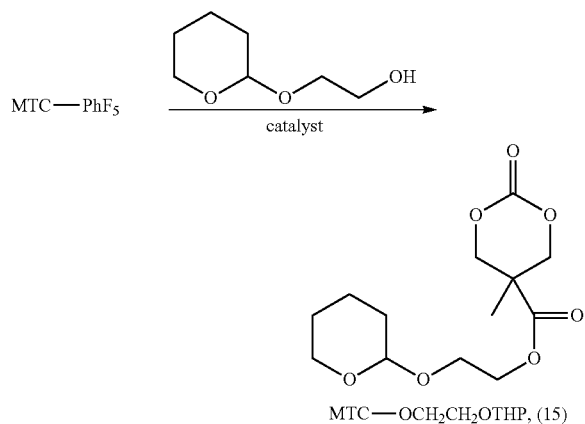

MTC—OCH$_2$CH$_2$OTHP, (15)

Figure 8:
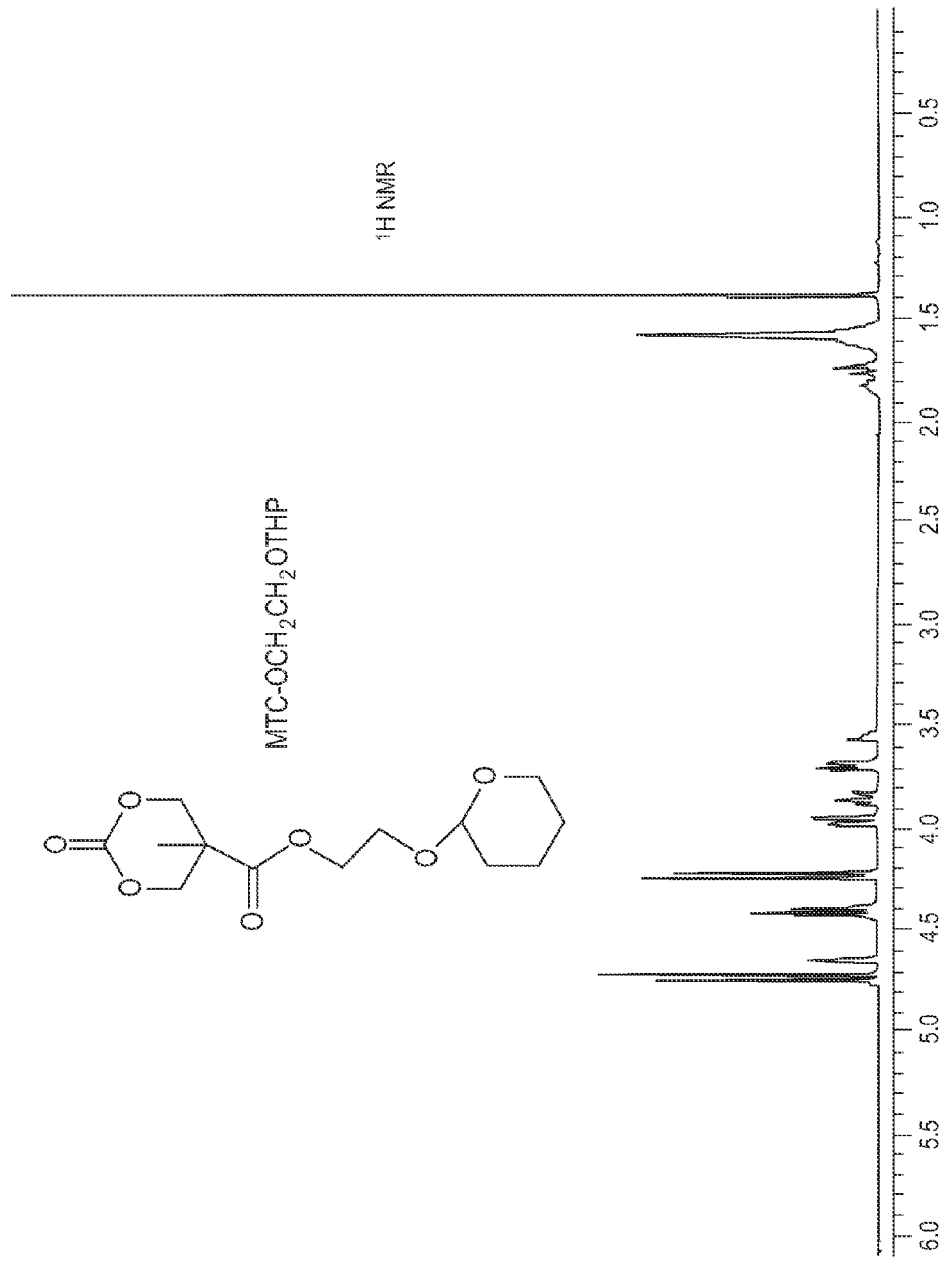

A round bottom flask was charged with MTC-PhF$_5$ (0.95, 0.0028 mol), CsF (0.14 g, 0.92 mmol) and 2-(tetrahydro-2H-pyran-2-yloxy)ethanol (0.43 g, 0.0029 mol), rinsed in with 10 mL of THF. The mixture was stirred for 24 hours, filtered to remove pentafluorophenol byproduct, and the solvent was evaporated. The reaction mixture was dissolved in methylene chloride, allowed to stand for about 30 min, and the additional precipitated pentafluorophenol byproduct was filtered. The pentafluorophenol byproduct was quantitatively recovered. This byproduct showed the characteristic 3 peaks in the $^{19}$F NMR of pentafluorophenol and a single peak in the GCMS with a mass of 184 g/mol. The organic phase was then treated with saturated NaHCO$_3$ (200 mL), brine (200 mL), water (200 mL), and dried over MgSO$_4$. The solvent was removed in vacuo. The crude product was purified by column chromatography (silica, 1:1 ethyl acetate/hexanes) to a colorless oil (Yield: 65%). GCMS showed a single peak with mass of 287 g/mol, calculated molecular weight for C$_{13}$H$_{20}$O$_5$ (288 g/mol) consistent with the assigned structure (FIG. 8). $^1$H NMR: δ 4.70 (d, 2H, CH$_2$OCOO), 4.61 (t, 1H, OCHO), 4.38 (m, 2H, OCOCH$_2$CH$_2$), 4.20 (d, 2H, CH$_2$OCOO), 3.92 (m, 1H, CH$_a$H$_b$OCH), 3.82 (m, 1H, OCH$_a$H$_b$CH$_2$CH$_2$), 3.65 (m, 1H, CH$_a$H$_b$OCH), 3.51 (m, 1H, OCH$_a$H$_b$CH$_2$CH$_2$), 1.85-1.65 (m, 2H, CHCH$_2$), 1.61-1.47 (m, 4H, CH$_2$CH$_2$CH$_2$CH$_2$), 1.35 (s, 3H, CH$_3$). $^{13}$C NMR: d 170.9, 147.4, 98.7, 72.9, 65.0, 64.7, 62.1, 40.1, 30.3, 25.2, 19.2, 17.5.

Example 9

Preparation of MTC-OCH$_2$CH$_2$NHBoc, (16)

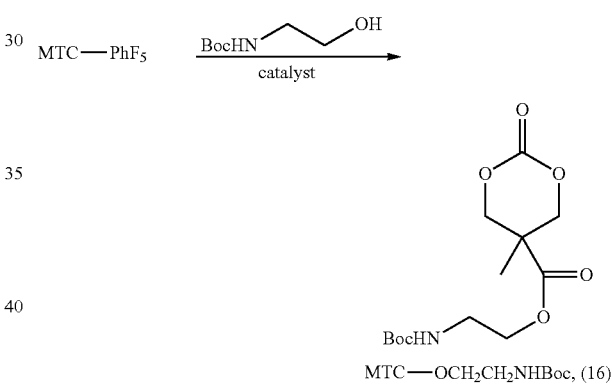

MTC—OCH$_2$CH$_2$NHBoc, (16)

Figure 9:
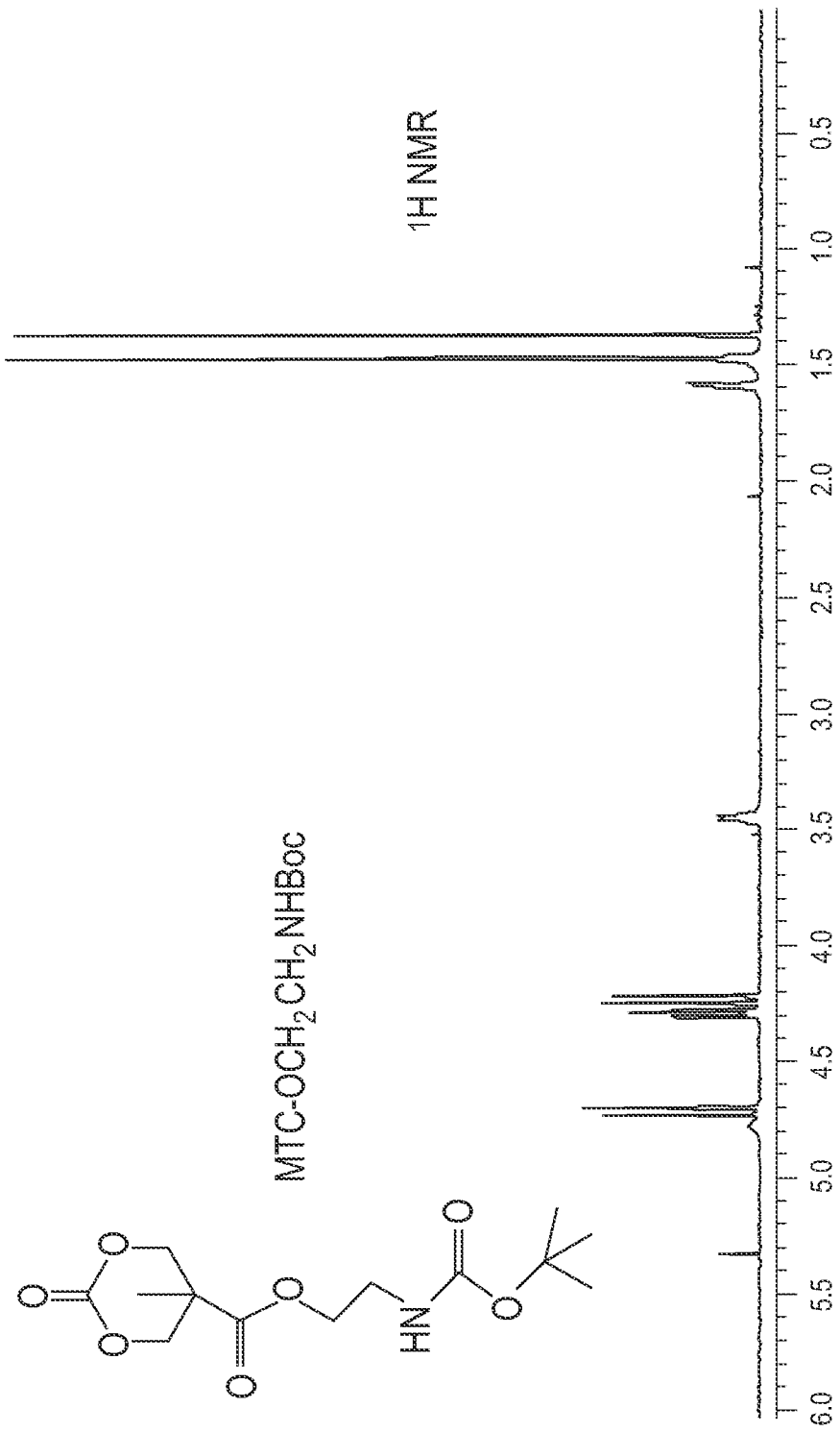

A round bottom flask was charged with MTC-PhF$_5$ (0.86, 0.00265 mol), CsF (0.14 g, 0.92 mmol) and N-Boc-ethanolamine (0.43 g, 0.0027 mol), rinsed in with 10 mL of THF. The reaction mixture was stirred for 24 hours, filtered to remove pentafluorophenol byproduct, and the solvent was evaporated in vacuo. The reaction mixture was redissolved in methylene chloride. After about 30 minutes, more of the pentafluorophenol byproduct precipitated and was filtered. The pentafluorophenol byproduct was quantitatively recovered. This byproduct showed the characteristic 3 peaks in the $^{19}$F NMR of pentafluorophenol and a single peak in the GCMS with a mass of 184 g/mol. The organic phase was then treated with saturated NaHCO$_3$ (200 mL), brine (200 mL), water (200 mL), dried over MgSO$_4$ and concentrated. Purification of the crude product by column chromatography (silica, 1:1 ethyl acetate/hexanes) provided the product as a solid, m.p. 52° C. to 55° C. Yield: 65%. GCMS showed a single peak with mass of 204 g/mol, with the loss of the boc-protecting group, calculated molecular weight for C$_{13}$H$_{15}$NO$_7$ (303 g/mol) consistent with the assigned structure (FIG. 9). $^1$H-NMR: δ 4.88 (br, 1H, NH), 4.69 (d, J=10.8 Hz, 2H, Cl/Ji$_b$), 4.26 (t, J=5.2 Hz, 2H, OCH$_2$CH$_2$), 4.21 (d, J=10.8 Hz, 2H, CH$_a$H$_b$), 3.42 (m, 2H, CH$_2$CH$_2$NH), 1.44 (s, 9H, C(CH$_3$)$_3$), 1.34 (s, 3H, CCH$_3$). $^{13}$C-NMR: δ 171.5, 156.3, 148.0, 80.1, 73.4, 65.8, 40.6, 39.8, 28.7, 17.8.

Example 10

Preparation of MTC-OBn, (17)

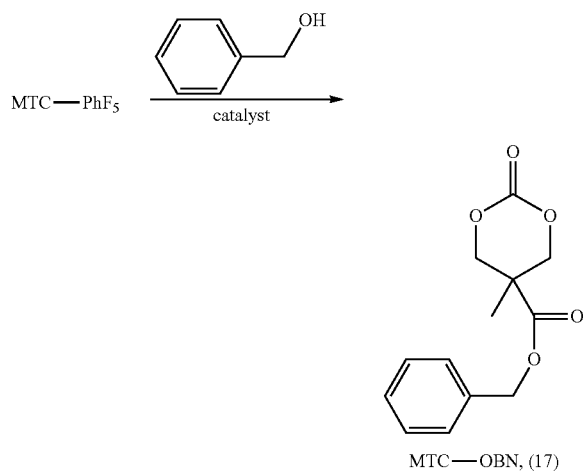

MTC—OBN, (17)

Figure 10:
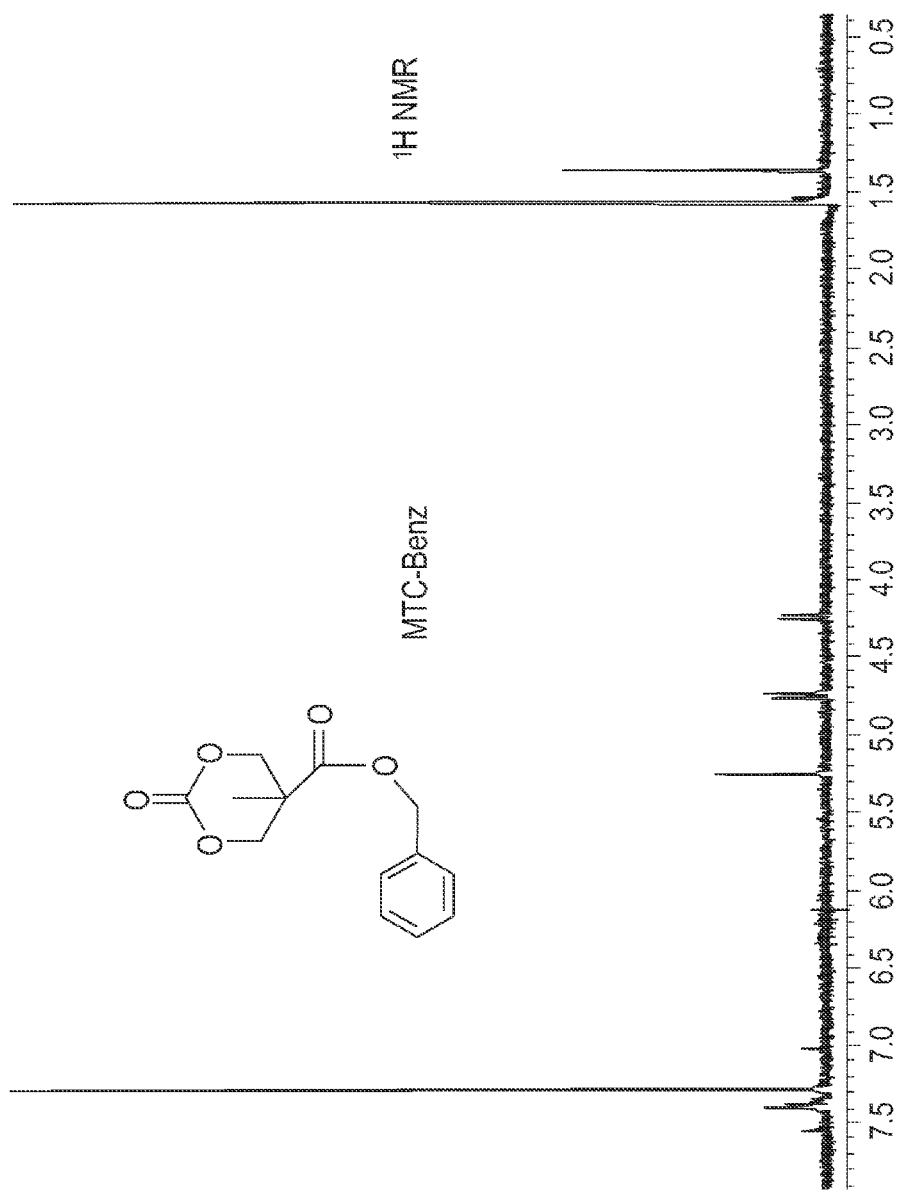

A round bottom flask was charged with MTC-PhF$_5$ (0.50, 0.0015 mol), CsF (0.30 g, 0.002 mol) and benzyl alcohol (0.17 g, 0.0015 mol), rinsed in with 10 mL of THF. The reaction mixture was stirred for 24 hours, filtered to remove pentafluorophenol byproduct, and the solvent was evaporated in vacuo. The reaction mixture was dissolved in methylene chloride. After about 30 minutes, more of the pentafluorophenol byproduct had precipitated and was filtered. The pentafluorophenol byproduct was quantitatively recovered. This byproduct showed the characteristic 3 peaks in the $^{19}$F NMR of pentafluorophenol and a single peak in the GCMS with a mass of 184 g/mol. The organic phase was then treated with saturated NaHCO$_3$ (200 mL), brine (200 mL), water (200 mL), dried over MgSO$_4$, and concentrated in vacu. The crude product was purified by column chromatography (silica, 1:1 ethyl acetate/hexanes) to give a solid, m.p. 67° C. to 69° C. Yield: 68%. GCMS showed a single peak with mass of 250 g/mol, calculated molecular weight for C$_{13}$H$_{14}$O$_5$ (250 g/mol) consistent with the assigned structure (FIG. 10). $^1$H-NMR (400 MHz in CDCl$_3$): δ 7.45 (m, 5H, ArH), 5.3 (s, 2H, ArCH$_2$), 4.70 (d, J=10.8 Hz, 2H, CH$_a$H$_b$), 4.25 (d, J=10.8 Hz, 2H, CH$_a$H$_b$), 1.35 (s, 3H, CCH$_3$).

Example 11

Preparation of MTC-OCH$_2$CH$_2$OCH$_2$CH$_2$OMe, (18)

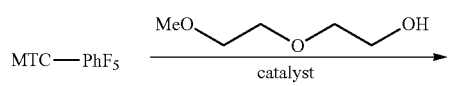

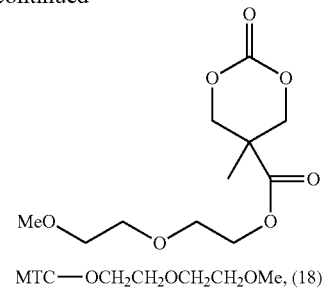

MTC—OCH$_2$CH$_2$OCH$_2$CH$_2$OMe, (18)

Figure 11:
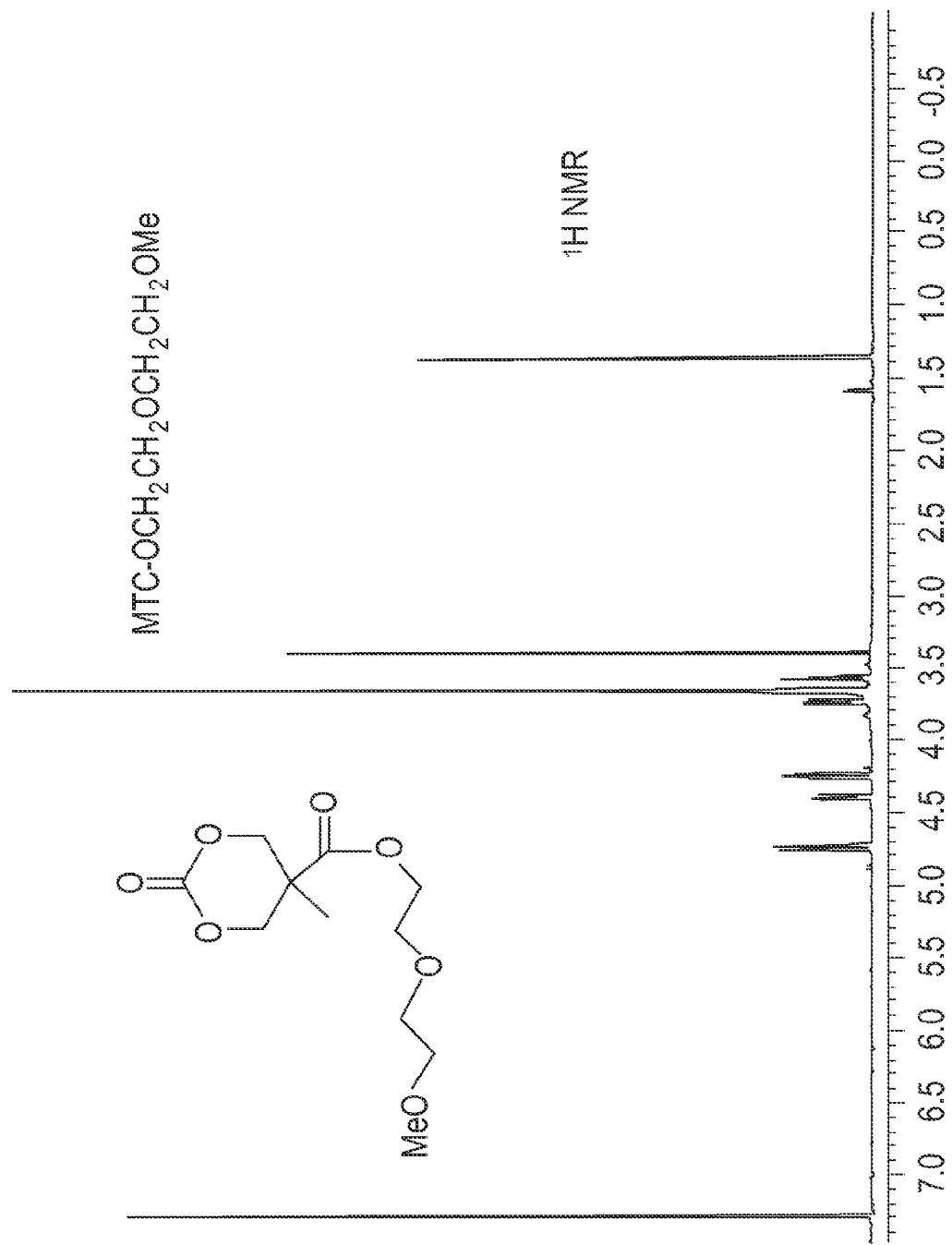

A round bottom flask was charged with MTC-PhF$_5$ (0.86, 0.00265 mol), CsF (0.14 g, 0.92 mmol) and diethylene glycol monomethyl ether (0.43 g, 0.0027 mol), rinsed in with 10 mL of THF. The reaction mixture was stirred for 24 hours, filtered to remove pentafluorophenol byproduct, and the solvent was evaporated in vacuo. The residue was dissolved in methylene chloride, allowed to stand about 30 minutes, and the additional precipitated pentafluorophenol byproduct was filtered. The pentafluorophenol byproduct was quantitatively recovered. The filtrate was concentrated and then dissolved in diethyl ether. The product separated out of the diethyl ether and was removed in a separation funnel and used without further purification (FIG. 11). The product was isolated as a liquid. Yield: about 50%. $^1$H-NMR (400 MHz in CDCl$_3$): δ=4.73-4.70 (d, 2H, —CH$_2$OCOOCH$_2$CCH$_3$—), 4.38-4.36 (t, 2H, PEG-CH$_2$CH$_2$—OCO), 4.22-4.20 (d, 4H, —CH$_2$OCOOCH$_2$CCH$_3$—), 3.65 (m, 4H, OCH2CH2 PEG), 3.38 (s, 3H, OCH2CH2OCH$_3$ PEG), 1.38 (s, 3H, CCH$_3$CH$_2$CCOOCH$_2$).

Example 12

Preparation of MTC-dinitroPHS, (19)

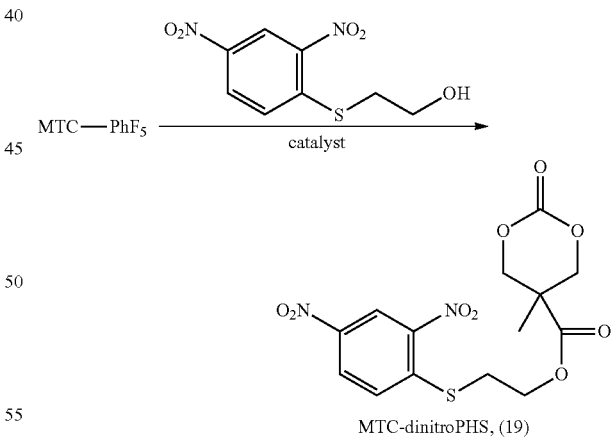

MTC-dinitroPHS, (19)

Figure 12:
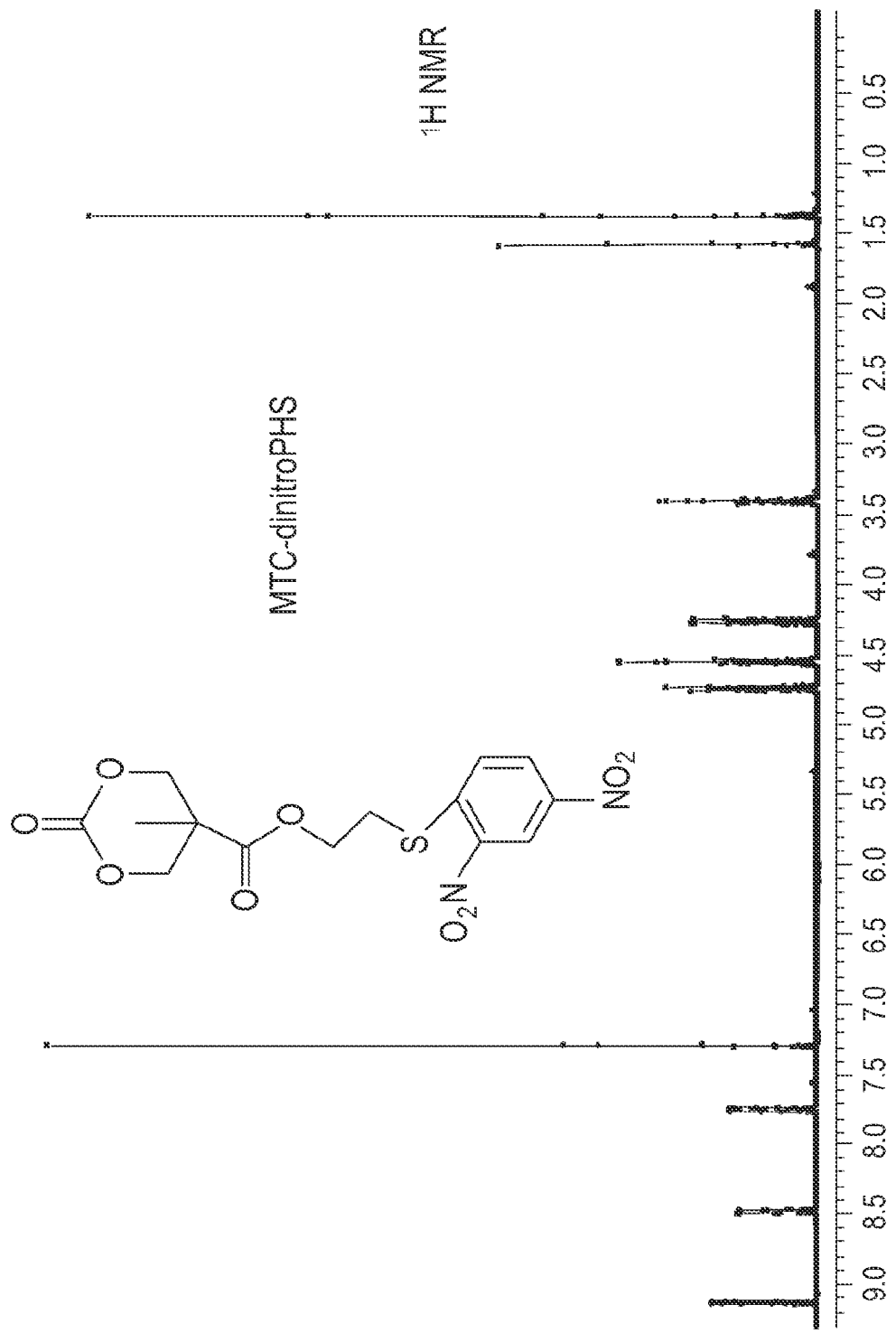

A round bottom flask was charged with MTC-PhF$_5$ (2.40 g, 7.43 mmol), CsF (0.31 g, 2.04 mmol) and 2-(2,4-dinitrophenylthio)ethanol (2.00 g, 8.19 mmol), rinsed in with 35 mL of THF. The mixture was stirred for 24 hours, filtered to remove pentafluorophenol byproduct, and the solvent was evaporated in vacuo. The residue was dissolved in methylene chloride, allowed to stand about 30 minutes, and filtered to remove additional precipitated pentafluorophenol byproduct. The pentafluorophenol byproduct was quantitatively recovered. The organic phase was then treated with saturated NaHCO$_3$ (200 mL), brine (200 mL), water (200 mL), dried over $MgSO_4$, and concentrated in vacuo. The crude product was purified by column chromatography (silica, 1:1 ethyl acetate/hexanes) to provide the desired product as an oil that slowly solidified to a yellow solid. Yield: (90%). The $^1$H NMR was consistent with the desired product (FIG. 12). $^1$H-NMR (400 MHz in $CDCl_3$): δ 9.25 (s, 1H, ArH), 8.45 (d, 1H, ArH), 7.70 (d, 1H, ArH), 4.70 (d, J=10.8 Hz, 2H, $CH_aH_b$), 4.55 (t, 2H, $COOCH_2$), 4.25 (d, J=10.8 Hz, 2H, $CH_aH_b$), 3.40 (t, 2H, $SCH_2$), 1.35 (s, 3H, $CCH_3$).

Example 13

Preparation of 5-methyl-5-(N-isopropylamino)carboxyl-1,3-dioxane-2-one (MTC-NiP), (20)

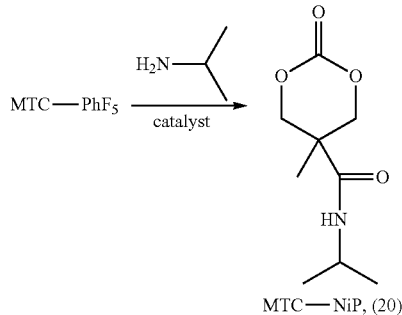

MTC-NiP, (20)

MTC-PhF$_5$ (500 mg, 1.54 mmol) and CsF (117 mg, 0.77 mmol) were mixed in THF (2 mL) and cooled by ice-salt bath. A solution of isopropylamine (200 microliters, 2.31 mmol) in THF (2 mL) was gently added to the mixture and the reaction mixture was stirred for 30 minutes before the reaction mixture was allowed to warm to room temperature. After an additional 16 hours stirring, the solvent was removed under vacuum, methylene chloride was added to the residue, and the insoluble material was filtered. The dried filtrate was concentrated under vacuum, and the residue was recrystallized from a mixture of ethyl acetate and diethyl ether to provide the product MTC-NiP as a white solid (225 mg, 72%). $^1$H NMR (400 MHz, $CDCl_3$): δ 5.74 (b, 1H, NH), 4.67 (d, 2H, $CH_2O$), 4.21 (d, 2H, $CH_2O$), 4.15-4.05 (m, 1H, CH), 1.32 (s, 3H, $CH_3$), 1.17 (d, 6H, CHCH$_3$). $^{13}$C NMR (100 MHz, $CDCl_3$): δ 169.1, 147.8, 73.8, 42.1, 39.7, 22.2, 17.6.

Example 14

Preparation of 5-methyl-5-(N,N-dimethylamino)carboxyl-1,3-dioxane-2-one (MTC-NMe$_2$), (21)

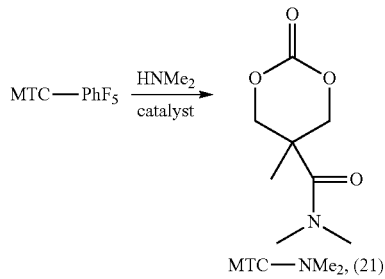

MTC-NMe$_2$, (21)

The synthesis was conducted by the same procedure and the same stoichiometry used for MTC-NiP in Example 13, using 2.0 M THF solution of dimethylamine as the amine in place of isopropylamine. The crude product MTC-NMe$_2$ was also purified by recrystallization (EtOAc/Et$_2$O) to yield a white solid (177 mg, 61.3%). $^1$H NMR (400 MHz, $CDCl_3$): δ 4.66 (d, 2H, $CH_2O$), 4.33 (d, 2H, $CH_2O$), 3.03 (s, 6H, $NCH_3$), 1.50 (s, 3H, $CH_3$). $^{13}$C NMR (100 MHz, $CDCl_3$): δ 169.7, 148.1, 73.6, 39.8, 37.5, 17.5.

Example 15

Synthesis of 5-methyl-5-trifluoroethoxylcarbonyl-1,3-dioxane-2-one (MTC-TFE), (22)

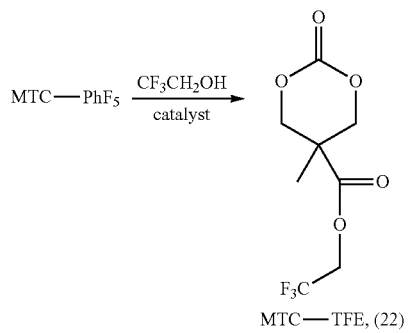

MTC-TFE, (22)

A THF solution (2 mL) of 2,2,2-trifluoroethanol (233 microliters, 3.20 mmol) was slowly added to a mixture of MTC-PhF$_5$ (1.0 g, 3.1 mmol) and CsF (193 mg, 1.27 mmol) in THF (4 mL) at room temperature and the reaction mixture was kept stirring for 17 hours before the solvent was dried under vacuum. The residue was then dissolved in methylene chloride, the insoluble material was filtered, the filtrate was dried and concentrated in vacuo to give the product MTC-TFE as a clear oil (616 mg, 81.7%). $^1$H NMR (400 MHz, $CDCl_3$): δ 4.74 (d, 2H, $CH_2O$), 4.61 (q, 2H, $CH_2CF_3$), 4.25 (d, 2H, $CH_2O$), 1.39 (s, 3H, $CH_3$). $^{13}$C NMR (100 MHz, $CDCl_3$): δ 169.8, 147.1, 122.4 (q), 72.5, 61.1 (q), 40.4, 17.0.

Part II. Detailed Description

The following description includes additional embodiments relating to the above-described Methods 2 (functionalization of the first cyclic carbonyl monomer bearing a pentafluorophenyl ester group) and Method 3 (ring opening polymerization of the first and second cyclic carbonyl monomers) of the parent disclosure. Method 4 (functionalization of a ROP polymer comprising a pentafluorophenyl ester group) is disclosed below.

The term "biodegradable" is defined by the American Society for Testing and Materials as a degradation caused by biological activity, especially by enzymatic action, leading to a significant change in the chemical structure of the material. For purposes herein, a material is biodegradable if it undergoes 60% biodegradation within 180 days in accordance with ASTM D6400.

Part II, Method 1. First Cyclic Monomers.

The precursor compounds for the first cyclic carbonyl monomers can have the general formula (23):

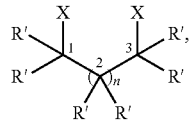

(23)

wherein together the X groups are cyclic carbonyl forming nucleophilic groups, each X independently represents a monovalent radical selected from the group consisting of —OH, —SH, —NH$_2$, and —NHR", wherein each R" group independently represents a monovalent radical selected from the group consisting of alkyl groups comprising 1 to 30 carbons, aryl groups comprising 6 to 30 carbons, and the foregoing R" groups substituted with a pentafluorophenyl ester forming carboxylic acid group, n' is 0 or an integer from 1 to 10, wherein when n' is 0 carbons labeled 1 and 3 attached to each X group are linked together by a single bond, each R' group independently represents a monovalent radical selected from the group consisting of hydrogen, pentafluorophenyl ester forming carboxylic acid groups, halides, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing R' groups substituted with a pentafluorophenyl ester forming carboxylic acid group, and at least one of the foregoing R' and/or R" groups comprises a pentafluorophenyl ester forming carboxylic acid group.

The R' and R" groups can further independently comprise a cycloaliphatic ring, an aromatic ring, and/or a heteroatom such as oxygen, sulfur or nitrogen. In an embodiment, the X groups of the precursor compound are hydroxy groups capable of forming a cyclic carbonate in a reaction with PFC.

Non-limiting examples of cyclic carbonyl forming moieties include 1,2-ethanediol groups, 1,3-propanediol groups, 1,4-butanediol groups, 1,2-ethanediamine groups, 1,3-propanediamine groups, 1,4-butanediamine groups, 2-aminoethanol groups, 3-amino-1-propanol groups, 4-amino-1-butanol groups, 2-mercaptoethanol groups, 3-mercapto-1-propanol groups, 1-mercapto-2-propanol groups, 4-mercapto-1-butanol groups, cysteamine groups, 1,2-ethanedithiol groups, and 1,3-propanedithiol groups. Cyclic carbonyl groups formed by the foregoing moieties in a reaction with PFC include cyclic carbonates from any of the above diols, cyclic ureas from any of the above diamines, cyclic carbamates from any of the above amino-alcohols, cyclic thiocarbonates from any of the above mercapto-alcohols, cyclic thiocarbamates from any of the above amino-thiols, and cyclic dithiocarbonates from any of the above dithiols. These functional groups are listed in Table 1.

TABLE 1

| Cyclic Carbonate | 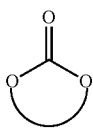 |
|---|---|
| Cyclic Urea | 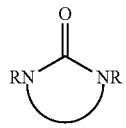 |
| Cyclic Carbamate | 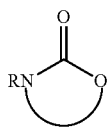 |

TABLE 1-continued

| Cyclic Thiocarbamate | 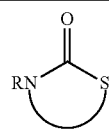 |
|---|---|
| Cyclic Thiocarbonate | 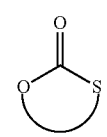 |
| Cyclic Dithiocarbonate | 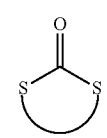 |

The first cyclic carbonyl compound comprises a cyclic carbonyl moiety selected from the group consisting of cyclic carbonates, cyclic carbamates, cyclic ureas, cyclic thiocarbonates, cyclic thiocarbamates, cyclic dithiocarbonates, and combinations thereof, formed by reaction of the two X groups with PFC. The first cyclic carbonyl compound further comprises a pendant pentafluorophenyl ester group (i.e., the moiety —$CO_2C_6F_5$) derived from a pentafluorophenyl ester forming carboxylic acid group of an R' and/or R" group.

The first cyclic carbonyl compounds can be represented by the general formula (24):

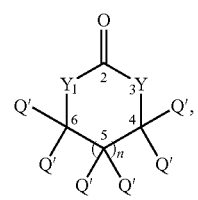

(24)

wherein each Y is a divalent radical independently selected from the group consisting of —O—, —S—, —N(H)—, or —N(Q")—, wherein each Q" group is a monovalent radical independently selected from the group consisting of alkyl groups comprising 1 to 30 carbons, aryl groups comprising 6 to 30 carbons, and the foregoing Q" groups substituted with a pentafluorophenyl ester group (i.e., —$CO_2C_6F_5$), n' is 0 or an integer from 1 to 10, wherein when n' is 0, carbons labeled 4 and 6 are linked together by a single bond, each Q' group is a monovalent radical independently selected from the group consisting of hydrogen, halides, pentafluorophenyl ester group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing Q' groups substituted with a pentafluorophenyl ester group, and wherein one or more of the Q' and/or Q" groups comprises a pentafluorophenyl ester group.

The Y groups in formula (24) are derived from the X groups of formula (1). In an embodiment, each Y in formula (24) is —O— and the first cyclic carbonyl compound comprises a cyclic carbonate group. In another embodiment, the first cyclic carbonyl compound comprises a single pendant pentafluorophenyl ester group.

The cyclic carbonyl group and the pendant pentafluorophenyl ester moiety are formed in one step from the precursor compound using PFC and a suitable catalyst. PFC is less toxic than other reagents (e.g., phosgene) in preparing cyclic carbonate compounds. PFC is a crystalline solid at room temperature that, being less sensitive to water than phosgene, can be easily stored, shipped, and handled. PFC does not require elaborate reaction and workup conditions. Moreover, the pentafluorophenol byproduct of the cyclization reaction is less volatile, less acidic, and less corrosive than hydrochloric acid. These advantages reduce the cost and complexity of the reactions, and potentially widen the scope of the starting materials to include compounds containing acid-sensitive groups. In addition, the pentafluorophenol byproduct of the cyclization reaction can be readily recycled back into PFC.

Isomerically pure precursor compounds having a hydrogen attached to an asymmetric carbon can be converted to a cyclic carbonyl compound comprising a pentafluorophenyl ester group without undergoing significant racemization. The esterification conditions are effective in achieving an enantiomeric excess of 80% or more, more specifically of 90% or more. In an embodiment, the cyclic carbonyl compound comprises an asymmetric carbon as an (R) isomer, in an enantiomeric excess of greater than 80%, more specifically greater than 90%. In another embodiment, the cyclic carbonyl compound comprises an asymmetric carbon as an (S) isomer, in an enantiomeric excess greater than 80%, more specifically greater than 90%.

Other precursor compounds are represented by the general formula (25):

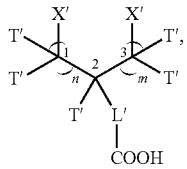

(25)

wherein the X' groups together are cyclic carbonyl forming nucleophilic groups, m and n are each independently 0 or an integer from 1 to 11, wherein m and n cannot together be 0, and m+n is an integer less than or equal to 11, each X' is a monovalent radical independently selected from the group consisting of —OH, —SH, —NH$_2$, and —NHT", wherein each T" is a monovalent radical independently selected from the group consisting of alkyl groups comprising 1 to 30 carbons, aryl groups comprising 6 to 30 carbons, and the foregoing T" groups substituted with a pentafluorophenyl ester forming carboxylic acid group, and each T' is a monovalent radical independently selected from the group consisting of hydrogen, halides, pentafluorophenyl ester forming carboxylic acid groups, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing T' groups substituted with a pentafluorophenyl ester forming carboxylic acid group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

The T' and T" groups can further independently comprise a cycloaliphatic ring, an aromatic ring, and/or a heteroatom such as oxygen, sulfur or nitrogen. In an embodiment, none of the T' or T" groups comprises a pentafluorophenyl ester forming carboxylic acid group, and L' is a single bond joining carbon labeled 2 of formula (25) with the carboxylic acid group. In another embodiment, the T' group attached to carbon labeled 2 in formula (25) is ethyl or methyl, and all other T' groups are hydrogen. In another embodiment, the T' group attached to carbon labeled 2 in formula (25) is ethyl or methyl, carbon labeled 2 in formula (25) is an asymmetric center, and the precursor compound comprises the (R) or (S) isomer in greater than 80% enantiomeric excess.

The corresponding first cyclic carbonyl compounds formed by the precursor compounds of formula (25) have the general formula (26):

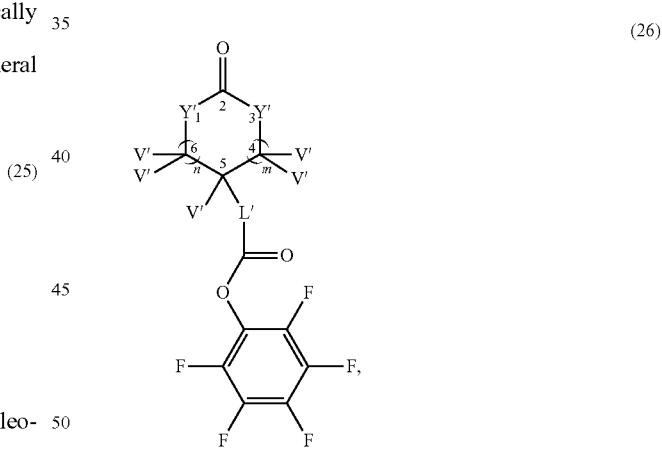

(26)

wherein m and n are each independently 0 or an integer from 1 to 11, wherein m and n cannot together be 0, and m+n is an integer less than or equal to 11, each Y' is a divalent radical independently selected from the group consisting of —O—, —S—, —N(H)— and —N(V")—, wherein each V" group is a monovalent radical independently selected from the group consisting of alkyl groups comprising 1 to 30 carbons, aryl groups comprising 1 to 30 carbons, and the foregoing V" groups substituted with a pentafluorophenyl ester group (—CO$_2$C$_6$F$_5$), each V' group is a monovalent radical independently selected from the group consisting of hydrogen, halides, pentafluorophenyl ester group, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing V' groups substituted with a pentafluorophenyl ester group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

In an embodiment, no V' group and no V''' group comprises a pentafluorophenyl ester group, and L' is a single bond joining carbon labeled 5 of formula (26) to the pentafluorophenyl ester group. In another embodiment, the V' group attached to the carbon labeled 5 in formula (26) is ethyl or methyl, and all other V' groups are hydrogen. In an embodiment, the V' group attached to carbon labeled 5 in formula (26) is ethyl or methyl, carbon labeled 5 in formula (26) is an asymmetric center, and the cyclic carbonyl compound comprises the (R) or (S) isomer in greater than 80% enantiomeric excess. In another embodiment, each Y' is —O—, and V' at position labeled 5 in formula (26) is a monovalent radical selected from the group consisting of hydrogen, halides, and alkyl groups comprising 1 to 30 carbons.

Even more specific first cyclic carbonyl compounds are cyclic carbonates having the general formula (27):

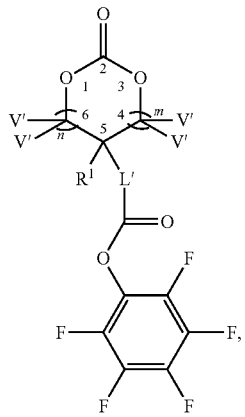

(27)

wherein
m and n are each independently 0 or an integer from 1 to 11, wherein m and n cannot together be 0, and m+n is less than or equal to 11, $R^1$ is a monovalent radical selected from the group consisting of hydrogen, halides, and alkyl groups comprising 1 to 30 carbons, each V' group is monovalent radical independently selected from the group consisting of hydrogen, halides, pentafluorophenyl ester group (—$CO_2C_6F_5$), alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing V' groups substituted with a pentafluorophenyl ester group, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

$R^1$ and L' can together form a first ring comprising 3 to 10 carbons. Each V' can independently form a second ring with a different V' group, with $R^1$, with L', or combinations thereof, wherein the second ring comprises 3 to 10 carbons.

In an embodiment, the cyclic carbonate compound of formula (27) comprises a single pentafluorophenyl ester group, and L' is a single bond joining carbon labeled 5 of formula (27) to the pentafluorophenyl ester group. In another embodiment, each V' is hydrogen. In another embodiment, m and n are equal to 1, and $R^1$ is a monovalent hydrocarbon group comprising 1 to 10 carbons. In another embodiment, $R^1$ is selected from the group consisting of methyl, ethyl, propyl, 2-propyl, n-butyl, 2-butyl, sec-butyl (2-methylpropyl), t-butyl (1,1-dimethylethyl), n-pentyl, 2-pentyl, 3-pentyl, iso-pentyl, and neo-pentyl.

Even more specific first cyclic carbonate monomers are represented by the general formula (28):

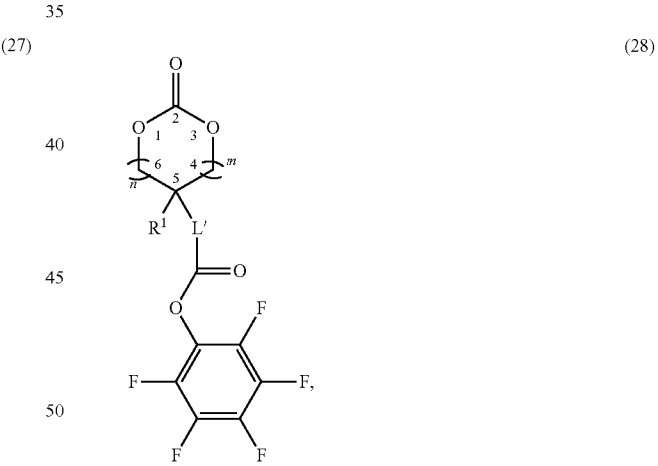

(28)

wherein
m and n are each independently 0 or an integer from 1 to 11, wherein m and n cannot together be 0, and m+n is less than or equal to 11, $R^1$ is a monovalent radical selected from the group consisting of hydrogen, halides, and alkyl groups comprising 1 to 30 carbons, and L' is a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons.

$R^1$ and L' can together form a first ring comprising 3 to 10 carbons. Each V' can independently form a second ring with a different V' group, with $R^1$, with L', or combinations thereof, wherein the second ring comprises 3 to 10 carbons.

In an embodiment, m and n are each independently 0 or an integer from 1 to 3, wherein m and n together cannot be 0, and L' is a single bond joining carbon labeled 5 of formula (28) to the pentafluorophenyl ester group. In another embodiment, m and n are each equal to 1, and $R^1$ is a monovalent hydrocarbon group comprising 1 to 10 carbons. Exemplary $R^1$ groups include, for example, methyl, ethyl, propyl, 2-propyl, n-butyl, 2-butyl, sec-butyl (2-methylpropyl), t-butyl (1,1-dimethylethyl), n-pentyl, 2-pentyl, 3-pentyl, iso-pentyl, and neo-pentyl.

Exemplary precursor compounds for preparing cyclic carbonate compounds bearing a pendant pentafluorophenyl ester group include but are not limited to bis(hydroxy)alkanoic acids, including bis(hydroxymethyl)alkanoic acids, such as 2,2-bis(hydroxymethyl)propionic acid, 2,2-bis(hydroxymethyl)butanoic acid, 2,2-bis(hydroxymethyl)pentanoic acid, 2,2-bis(hydroxymethyl)hexanoic acid, and 4,4-bis(hydroxymethyl)pentanoic acid. Other exemplary precursor compounds include 2,2,5,5-tetrakis(hydroxymethyl)adipic acid, and 2-[2,2-bis(hydroxymethyl)butoxycarbonyl]cyclopropane-1-carboxylic acid.

In an embodiment, the first cyclic carbonate compound is selected from the group consisting of

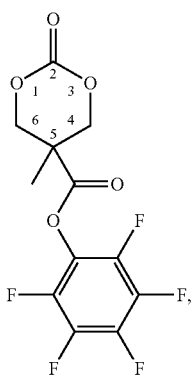

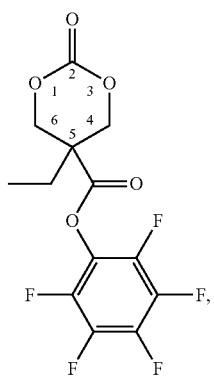

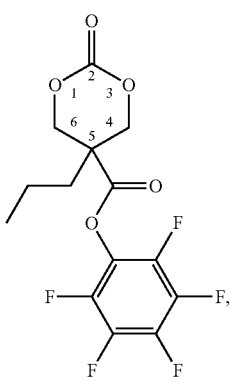

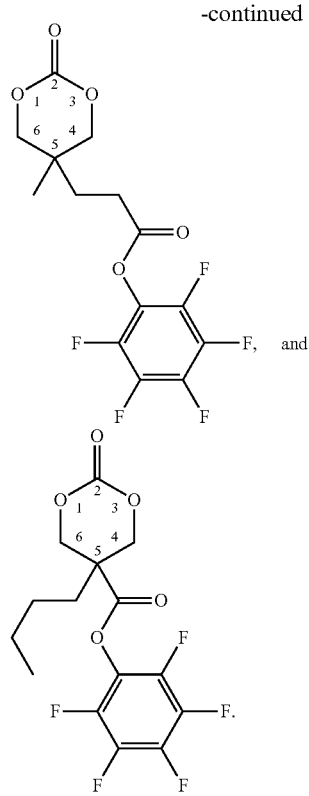

Method 1. Preparation of the First Cyclic Carbonyl Compound

A method (Method 1) of preparing a first cyclic carbonyl compound bearing a pendant pentafluorophenyl ester group comprises forming a first mixture comprising bis(pentafluorophenyl) carbonate, a catalyst, an optional solvent, and a precursor compound, the precursor compound comprising i) three or more carbons, ii) a carboxylic acid group capable of forming a pentafluorophenyl ester group in a reaction with bis(pentafluorophenyl) carbonate, and iii) at least two nucleophilic groups (e.g., the X groups in formula (23)) independently selected from the group consisting of hydroxy group, primary amines, secondary amines, and thiol group, the two nucleophilic groups capable of forming a cyclic carbonyl group in a reaction with bis(pentafluorophenyl) carbonate. The first mixture is agitated at a temperature effective in forming a first cyclic carbonyl compound. The first cyclic carbonyl compound comprises i) a pendant pentafluorophenyl ester group and ii) a cyclic carbonyl moiety selected from the group consisting of cyclic carbonates, cyclic ureas, cyclic carbamates, cyclic thiocarbamates, cyclic thiocarbonates, and cyclic dithiocarbonates.

The formation of the cyclic carbonyl moiety and the pendant pentafluorophenyl ester group can occur in a single process step under mild conditions.

The precursor compound can comprise more than one pentafluorophenyl ester forming carboxylic acid group and more than two nucleophilic groups capable of forming a cyclic carbonyl group in a reaction with bis(pentafluorophenyl) carbonate. Consequently, the first cyclic carbonyl monomer can comprise more than one cyclic carbonyl moiety and more than one pendant pentafluorophenyl ester group. In an embodiment, the first cyclic carbonyl compound comprises one pentafluorophenyl ester group. In another embodiment, the first cyclic carbonyl compound comprises one cyclic carbonyl moiety.

A method of preparing a first cyclic carbonyl monomer comprises forming a first mixture comprising i) a precursor compound, ii) bis(pentafluorophenyl) carbonate, iii) a catalyst, and iv) an optional solvent, wherein the precursor compound comprises a) three or more carbons, b) two nucleophilic groups capable together of forming a cyclic carbonate group, the nucleophilic groups independently selected from the group consisting of hydroxy group, primary amines, secondary amines, and thiol group, and c) a carboxylic acid group; and agitating the first mixture, thereby forming a first cyclic carbonyl compound comprising a pendant pentafluorophenyl ester group, the cyclic carbonyl compound comprising a cyclic carbonyl moiety selected from the group consisting of cyclic carbonates, cyclic ureas, cyclic carbamates, cyclic thiocarbamates, cyclic thiocarbonates, and cyclic dithiocarbonates.

A specific method of preparing a first cyclic carbonate compound comprises forming a first mixture comprising i) a precursor compound, ii) bis(pentafluorophenyl) carbonate, and iii) a catalyst, wherein the precursor compound comprises a) three or more carbons, b) two hydroxy groups capable together of forming a cyclic carbonate group, and c) a carboxylic acid group; and agitating the first mixture, thereby forming a first cyclic carbonate compound comprising a pendant pentafluorophenyl ester group.

An even more specific method of forming a first cyclic carbonyl monomer comprises agitating a first mixture comprising i) a precursor compound comprising two or more carbons, two or more hydroxy groups, and one or more carboxy groups, ii) bis(pentafluorophenyl) carbonate, and iii) a catalyst, thereby forming a first cyclic carbonate compound comprising a pendant pentafluorophenyl ester group.

Part II, Method 2. Functionalization of the First Cyclic Monomer.

Also disclosed is a mild method (Method 2) of preparing a second cyclic carbonyl compound from the first cyclic carbonyl compound by selectively reacting the first cyclic carbonyl compound with a nucleophile such as an alcohol, amine, or thiol, without altering the cyclic carbonyl moiety of the first cyclic carbonyl compound, thereby forming a second cyclic carbonyl compound and pentafluorophenol byproduct. In this reaction, the pendant pentafluorophenyl ester group is converted to a second functional group selected from the group consisting of alcohol based esters other than pentafluorophenyl ester, carbamates, and thiocarbonates. The second functional group can comprise from 1 to 10000 carbons. An optional catalyst can be used with weaker nucleophiles such as alcohols when forming the second cyclic carbonyl compound. Generally, a catalyst is not required for the reaction of a pendant pentafluorophenyl ester group with stronger nucleophiles (e.g., primary amines). In an embodiment, the second cyclic carbonyl compound comprises no pentafluorophenyl ester groups.

The second cyclic carbonyl compounds can have the general formula (29):

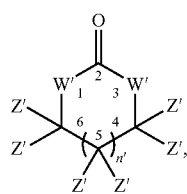

(29)

wherein n' is 0 or an integer from 1 to 10, wherein when n' is 0 carbons labeled 4 and 6 are linked together by a single bond, each W' is a divalent radical independently selected from the group consisting of —O—, —S—, —N(H)— or —N(W"), wherein each W" group independently represents a monovalent radical selected from the group consisting of alkyl groups comprising 1 to 30 carbons, aryl groups comprising 1 to 30 carbons, and the foregoing W" groups substituted with a second functional group selected from the group consisting of alcohol based esters other than pentafluorophenyl ester, amides, and thioesters, each Z' group independently represents a monovalent radical selected from the group consisting of hydrogen, the second functional group, halides, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, aryl groups comprising 6 to 30 carbons, thioester groups comprising 1 to 30 carbons, urea groups comprising 1 to 30 carbons, carbamate groups comprising 1 to 30 carbons, ether groups comprising 1 to 30 carbons, alkoxy groups comprising 1 to 30 carbons, and the foregoing Z' groups substituted with a second functional group selected from the group consisting of alcohol based esters other than pentafluorophenyl ester, amides, and thioesters, and the second cyclic carbonyl compound comprises no pentafluorophenyl ester group (—CO₂PFP) and no pentafluorophenyl carbonate group (—OCO₂PFP).

A more specific second cyclic carbonyl compound has the general formula (30):

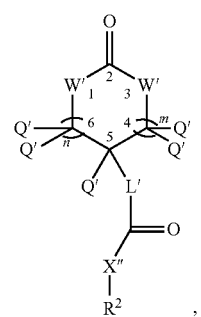

(30)

wherein m and n are each independently 0 or an integer from 1 to 11, wherein m and n cannot together be 0, and m+n equals an integer from 1 to 11, each W' independently represents divalent radical selected from the group consisting of O, S, NH or NW", wherein each W" group independently represents a monovalent radical selected from the group consisting of alkyl groups comprising 1 to 30 carbons, and aryl groups comprising 1 to 30 carbons, and the foregoing W" groups substituted with a second functional group selected from the group consisting of alcohol based esters other than pentafluorophenyl ester, amides, and thioesters, L' represents a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons, each Q' group independently represents a monovalent radical selected from the group consisting of hydrogen, the second functional group, halides, alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, ether groups comprising 1 to 30 carbons, and alkoxy groups comprising 1 to 30 carbons, and any of the foregoing Q' groups substituted with a second functional group selected from the group consisting of alcohol based esters other than pentafluorophenyl ester, amides, and thioesters, each X" is a divalent radical independently selected from the group consisting of —O—, —S—, —N(H)—, and —N(R$^3$)—, each R$^2$ and R$^3$ is independently a monovalent radical comprising 1 to 10,000 carbons, and the second cyclic carbonyl compound contains no pentafluorophenyl ester group and no pentafluorophenyl carbonate group.

In an embodiment, each W' is —O— (i.e., the second cyclic carbonyl compound is a cyclic carbonate). In another embodiment, the Q' group attached to the carbon 5 in formula (30) is ethyl or methyl, and all other Q' groups are hydrogen. In another embodiment, carbon 5 in formula (30) is an asymmetric center, and the cyclic carbonyl compound comprises the (R) or (S) isomer in greater than 80% enantiomeric excess.

Even more specific second cyclic carbonyl compounds derived from the first cyclic carbonyl monomer are cyclic carbonates of the general formula (31):

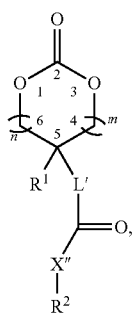

(31)

wherein m and n are each independently 0 or an integer from 1 to 11, wherein m and n cannot together be 0; and m+n equals an integer from 1 to 11, L' represents a single bond or a divalent linking group selected from the group consisting of alkyl groups comprising 1 to 30 carbons, alkene groups comprising 1 to 30 carbons, alkyne groups comprising 1 to 30 carbons, aryl groups comprising 6 to 30 carbons, ester groups comprising 1 to 30 carbons, amide groups comprising 1 to 30 carbons, thioester groups comprising 1 to 30 carbons, urea groups comprising 1 to 30 carbons, carbamate groups comprising 1 to 30 carbons, and ether groups comprising 1 to 30 carbons;

R$^1$ is a monovalent radical selected from the group consisting of hydrogen, halides, and alkyl groups comprising 1 to 30 carbons;

each X" is a divalent radical independently selected from the group consisting of —O—, —S—, —N(H)—, and —N(R$^3$)—; and each R$^2$ and R$^3$ is independently a monovalent radical comprising 1 to 10,000 carbons; and the second cyclic carbonyl compound contains no pentafluorophenyl ester group and no pentafluorophenyl carbonate group.

The reaction to form the second functional group occurs without disrupting the cyclic carbonyl moiety, in particular the cyclic carbonate moiety, of the first cyclic carbonyl compound. The byproduct of the displacement reaction, pentafluorophenol, can be recovered and recycled, typically in high yield. The second cyclic carbonate compounds are potentially capable of forming ROP polycarbonates and other polymers by ROP methods. The ROP polymers can have unique pendant functionalities and properties due to the wide variety of available materials for the pendant —X"—R$^2$ group in formula (29), formula (30), and formula (31).

The method (Method 2) of preparing a second cyclic carbonyl compound comprises agitating a mixture comprising the first cyclic carbonyl compound comprising a pentafluorophenyl ester group; an optional solvent; an optional catalyst; and a nucleophile selected from the group consisting of alcohols, amines, and thiols, thereby forming a second cyclic carbonyl monomer and pentafluorophenol byproduct, wherein the second cyclic carbonyl monomer comprises a second functional group selected from the group consisting of alcohol based esters other than pentafluorophenyl ester, amides, and thioesters formed by a reaction of the pentafluorophenyl ester group with the nucleophile.

Additional alcohols to those listed in Part I that are capable of transesterifying a pentafluorophenyl ester of the first cyclic carbonyl monomer without altering the cyclic carbonyl group include:

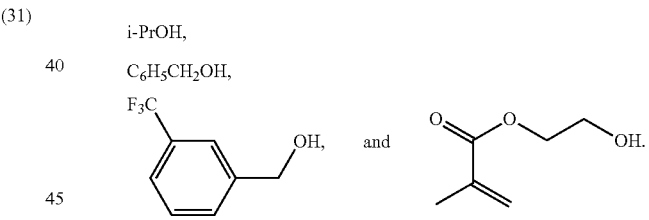

Additional non-limiting examples of amines capable of reacting with the pentafluorophenyl ester group to form a pendant amide, without altering the cyclic carbonate group, include:

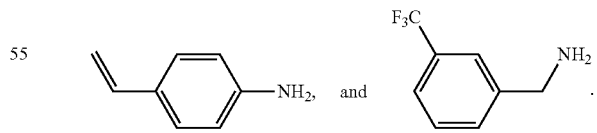

Non-limiting examples of thiols capable of reacting with the pendant PFP ester to form a pendant thioester without altering the cyclic carbonyl group include: methane thiol, ethane thiol, phenylthiol, benzyl thiol, and the like.

In general, the efficacy of the substitution reactions proceed in accordance with the nucleophilicity of the nucleophiles. For example, stronger nucleophiles such as primary amines are more effective than weaker nucleophiles such as primary alcohols. In another example, primary and secondary alcohols can be more effective nucleophiles than sterically hindered alcohols such as tert-butanol in a reaction with the pendant pentafluorophenyl ester group.

The nucleophile in Method 2 can be a polymeric alcohol. The polymeric alcohol can comprise from 4 to 10000 carbons. In one example, the nucleophile is a polyether alcohol, and the pentafluorophenyl ester group of the first cyclic carbonyl compound reacts with the polyether alcohol to form a second cyclic carbonyl containing material comprising a pendant hydrophilic polyether ester group, exemplified by monomer MTCOMPEG (Table 3 further below).

Non-limiting examples of polymeric alcohols include polyether alcohols, such as polyethylene glycol (PEG), and mono end capped polyethylene glycol, such as monomethyl endcapped polyethylene glycol (MPEG):

MPEG

Other polymeric alcohols include polypropylene glycol (PPG) and mono endcapped derivatives thereof, such as monomethyl end capped polypropylene glycol (MPPG):

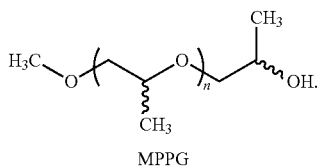

MPPG

Still other polymeric alcohols include poly(alkylene glycols) of formulas (32), (33), and (34) described further below.

Generally, the first mixture (Method 2) is agitated at a temperature of −78° C. to 100° C., more specifically −20° C. to 50° C., and even more specifically −10° C. to 30° C. to form the second cyclic carbonyl compound. In an embodiment, agitation to convert the pentafluorophenyl ester to a different alcohol based ester, amide, or thioester is conducted at ambient temperature (herein, 17° C. to 30° C.). The first mixture is agitated for a period of about 1 hour to about 48 hours, more particularly about 20 to 30 hours at the reaction temperature. In an embodiment, the first cyclic carbonyl compound and the second cyclic carbonyl compound are each a cyclic carbonate.

Generally, 1.2 to 1.5 equivalents of the nucleophile with respect to the pentafluorophenyl ester are used in the substitution reaction. When a large excess nucleophile is used (e.g., more than 4 equivalents), ring-opening of the cyclic carbonate can occur as a side reaction.

Typically, a solvent is used in Method 2, though a solvent is not required. Depending on the solvent, the pentafluorophenol byproduct can in some instances precipitate directly from the reaction mixture as it is formed. The second cyclic carbonyl compound can be isolated using any known method of purification, including distillation, chromatography, extraction, precipitation, and recrystallization. Generally, however, the second mixture is concentrated under vacuum and the resulting residue is then treated with a second solvent in which the pentafluorophenol byproduct is not soluble, such as methylene chloride. The pentafluorophenol byproduct can then be filtered and recovered for recycling back to PFC. In an embodiment, 90% to 100% of the theoretical pentafluorophenol byproduct is recovered for recycling back to PFC. In one variation, the derived second cyclic carbonate compound can be isolated by washing the organic filtrate with a base such as sodium bicarbonate solution, drying the filtrate with a drying agent such as magnesium sulfate or sodium sulfate, and evaporating the second solvent under vacuum. In a another variation, the second cyclic carbonyl compound is further purified by column chromatography or recrystallization. In this manner the second cyclic carbonyl compound can be obtained in a yield of about 50% to about 100%, more particularly about 70% to 100%, even more particularly about 80% to 100%.

The optional catalyst of Method 2 can be selected from typical catalysts for transesterifications, conversions of esters to amides, or conversion of esters to thioesters. These include organic catalysts and inorganic catalysts, in particular the above described catalysts, and most specifically cesium fluoride. When used in Method 2, the catalyst can be present in an amount of 0.02 to 1.00 moles per mole of the first cyclic carbonyl compound, more particularly 0.05 to 0.50 moles per mole of the first cyclic carbonyl compound, and even more particularly 0.15 to 0.25 moles per mole of the first cyclic carbonyl compound.

In an additional embodiment, Method 1 and Method 2 are performed step-wise in a single reaction vessel, without an intermediate step to isolate the first cyclic carbonyl compound.

The above-described methods provide a controlled process for introducing a wide range of functionality and connectivity into cyclic carbonyl compounds for ring-opening polymerizations. As stated above, the cyclic carbonyl compounds (first and/or second cyclic carbonyl compounds) can be formed in isomerically pure form, or as racemic mixtures.

Part II, Method 3. Ring Opening Polymerization of the First Cyclic Monomer

As described in Part I, ROP polymers can be obtained by nucleophilic ring opening polymerization of the above described first and second cyclic carbonyl compounds. The ROP polymer comprises a chain fragment derived from the nucleophilic initiator for the ROP polymerization, and a first polymer chain linked to the chain fragment. The chain fragment is also referred to herein as the initiator fragment. The initiator fragment comprises at least one oxygen, nitrogen, and/or sulfur backbone heteroatom, which is a residue of a respective alcohol, amine, or thiol nucleophilic initiator group of the ROP initiator. The backbone heteroatom is linked to the first end unit of the first polymer chain grown therefrom. A second end unit of the first polymer chain can be a living end unit capable of initiating additional ring opening polymerization, if desired. A living second end unit comprises a nucleophilic group selected from the group consisting of hydroxy group, primary amines, secondary amines, and thiol group. Alternatively, the second end unit can be endcapped to impart stability to the ROP polymer, as described further below.

It is understood that the initiator fragment has a different structure than the first end unit of each ROP polymer chain connected thereto.

The ROP initiator can comprise one or more independently chosen alcohol, amine, or thiol nucleophilic initiator groups. Each nucleophilic initiator group can potentially initiate a ring opening polymerization. Likewise, the initiator fragment comprises at least one backbone heteroatom derived from a nucleophilic initiator group. Each one of the backbone heteroatoms that is derived from a nucleophilic initiator group is linked to a ROP polymer chain grown therefrom. Thus, an initiator comprising n nucleophilic initiator groups can potentially initiate formation of n independent ROP polymer chains, where n is an integer equal to or greater than 1. As a non-limiting example, a dinucleophilic initiator comprising two hydroxy groups can initiate a ring opening polymerization at each hydroxy group. The product ROP polymer comprises an initiator fragment linked to two ROP polymer chains through the two backbone oxygens derived from the hydroxy initiator groups.

The ROP polymer comprises a first polymer chain. The first polymer chain can comprise a homopolymer, random copolymer, block copolymer, or combinations of the foregoing polymer types. The first polymer chain comprises a first repeat unit comprising a backbone functional group selected from the group consisting of carbonate, ureas, carbamates, thiocarbamates, thiocarbonate, and dithiocarbonate. The first repeat unit further comprises a tetrahedral backbone carbon. In an embodiment, the tetrahedral backbone carbon is linked to a first side chain comprising a pendant pentafluorophenyl ester group. In another embodiment, the tetrahedral backbone carbon is linked to a first side chain comprising a pendant pentafluorophenyl ester group, and to a second side chain selected from the group consisting of hydrogen, halides, and alkyl groups comprising 1 to 30 carbons (e.g., the $R^1$ group as described in formulas (27) and (28)).

In the following non-limiting examples, R'—XH is an mono-nucleophilic initiator for ring opening polymerization. R'—XH comprises a monovalent initiator group —XH, wherein X is a divalent group selected from the group consisting of —O—, —NH—, —N(R")—, and —S—. No restriction is placed on the structure of R' or R" with the proviso that the ring opening polymerization produces a useful ROP polymer.

As one example, the nucleophilic ring opening polymerization of a first cyclic carbonyl monomer of formula (24) initiated by R'—XH produces a ROP polymer of formula (24A), which comprises a first polymer chain linked to initiator fragment R'—X—.

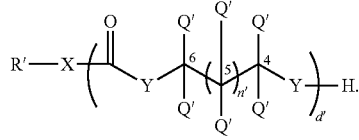

(24A)

Initiator fragment R'—X— is linked to the carbonyl of the first end unit of the ROP polymer chain by the oxygen, nitrogen or sulfur heteroatom of the X group. A second end unit of the ROP polymer chain remains a living end unit (i.e., the —Y—H group in formula (24A)), wherein —Y—H is a nucleophilic hydroxy group, primary amine group, secondary amine group, or thiol group. Y, Q', and n' are defined as above under formula (24); therefore, at least one of the Q' groups and/or Q" groups (of the Y groups) comprises a pendant pentafluorophenyl ester group (—$CO_2C_6F_5$). The subscript d' is an integer from 1 to 10000. The repeat unit

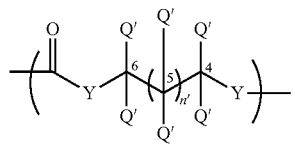

comprises a backbone functional group selected from the group consisting of carbonate, ureas, carbamates, thiocarbamates, thiocarbonate, and dithiocarbonate, determined by the independent selection of each Y group. The first repeat unit further comprises tetrahedral backbone carbons labeled 4, 5 and 6. Each of these backbone carbons can be linked to a first side chain Q' which can comprise a pentafluorophenyl ester group. Further, each of these tetrahedral backbone carbons can be linked to an optional second side chain Q' group, defined above under formula (24).

In another example, the nucleophilic ring opening polymerization of a first cyclic carbonyl monomer of formula (26), initiated by R'—XH, produces a ROP polymer of formula (26A), which comprises a first polymer chain linked to initiator fragment R'—X—:

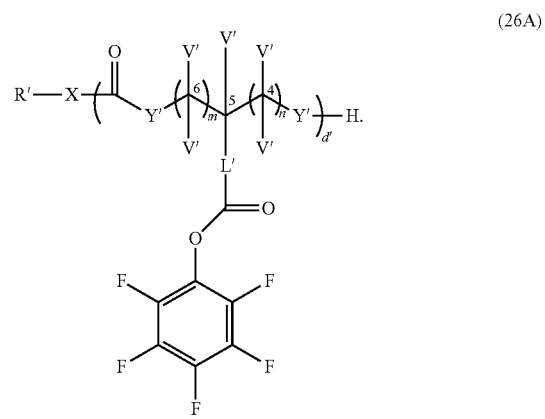

(26A)

The initiator fragment R'—X— is linked to the carbonyl of the first end unit of the ROP polymer chain by the oxygen, nitrogen or sulfur heteroatom of the X group. Y', L', V', n and m are defined as above under formula (26). The subscript d' is an integer from 1 to 10000. The repeat unit

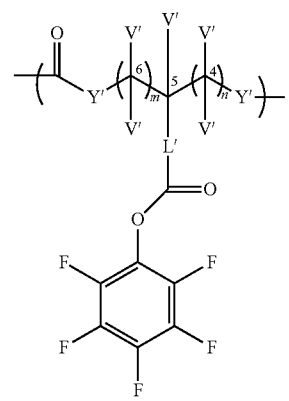

comprises a backbone functional group selected from the group consisting of carbonate, ureas, carbamates, thiocarbamates, thiocarbonate, and dithiocarbonate, determined by the independent selection of each Y' group. Tetrahedral backbone carbon 5 is linked to a first side chain comprising a pentafluorophenyl ester group. Tetrahedral backbone carbon 5 can optionally be linked to a second side chain V' group, as defined above under formula (26).

In another example, the nucleophilic ring opening polymerization of a first cyclic carbonyl monomer of formula (27), initiated by R'—XH, produces a ROP polymer of formula (27A), which comprises a first polymer chain linked to initiator fragment R'—X—:

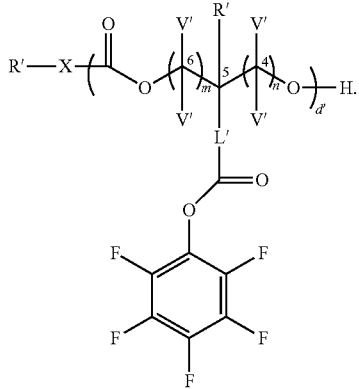

(27A)

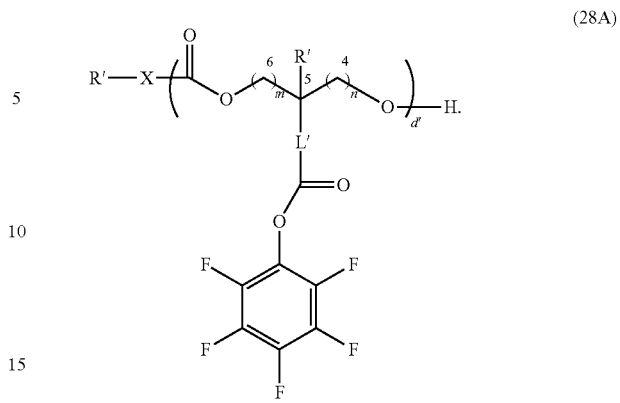

(28A)

As above, the initiator fragment R'—X— is linked to the carbonyl of the first end unit of the ROP polymer chain by the oxygen, nitrogen or sulfur heteroatom of the X group. Y', L, V', n and m are defined as above under formula (27). The subscript d' is an integer from 1 to 10000. The repeat unit

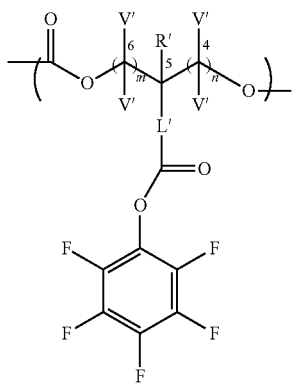

comprises a backbone functional group selected from the group consisting of carbonate, ureas, carbamates, thiocarbamates, thiocarbonate, and dithiocarbonate, determined by the independent selection of each Y' group. Tetrahedral backbone carbon labeled 5 is linked to a first side chain comprising a pentafluorophenyl ester group, and to a second side chain R' defined above under formula (27). Tetrahedral backbone carbons labeled 4 and 6 can independently be linked to independent first and second side chain V' groups, as described above under formula (27).

In another example, the nucleophilic ring opening polymerization of a first cyclic carbonyl monomer of formula (28), initiated by R'—XH, produces a polycarbonate of formula (28A), which comprises a first polycarbonate chain linked to initiator fragment R'—X—:

Initiator fragment R'—X— is linked by the oxygen, nitrogen or sulfur heteroatom of the X group to the carbonyl of the first end unit of the ROP polycarbonate chain. $R^1$, L', V', m and n are defined as above under formula (28). The subscript d' is an integer from 1 to 10000. The repeat unit

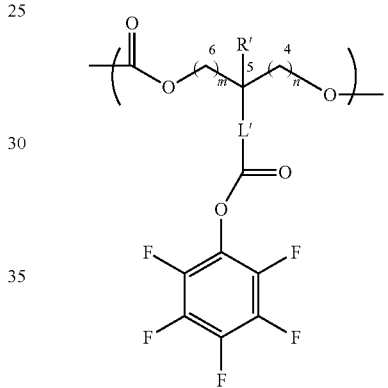

comprises a backbone carbonate group. Tetrahedral backbone carbon labeled 5 is linked to a first side chain comprising a pentafluorophenyl ester group, and to a second side chain $R^1$ group defined above under formula (28).

The ROP polymer can comprise two or more polymer chains. Additionally, each polymer chain can be a homopolymer of a respective first repeat unit, or a copolymer comprising a second repeat unit, the second repeat unit comprising a second backbone functional group selected from the group consisting of esters, carbonates, ureas, carbamates, thiocarbamates, thiocarbonates and dithiocarbonates, which is derived from a cyclic carbonyl comonomer. The first polymer chain can be a random copolymer or a block copolymer comprising the first and second repeat units.

Similar considerations apply to ROP polymers prepared from a second cyclic carbonyl compound, except that the ROP polymer chain does not comprise a pentafluorophenyl ester side chain group or a pentafluorophenyl carbonate group. Instead, the ROP polymer comprises a repeat unit comprising a side chain comprising a different alcohol based ester group, amide group, or thioester group derived from the pendant pentafluorophenyl ester group of the first cyclic carbonyl monomer.

The first and/or second cyclic carbonyl compounds can undergo ring-opening polymerization (ROP) to form biodegradable polymers having different tacticities. Atactic, syndiotactic and isotactic forms of the polymers can be produced that depend on the cyclic carbonyl monomer(s), its isomeric purity, and the polymerization conditions.

The ring opening polymerization (ROP) of the first cyclic carbonyl compound can occur with substantial retention of the pentafluorophenyl ester group in the product ROP polymer, which is also referred to as the first ROP polymer. The first ROP polymer comprises at least one repeat unit comprising a side chain comprising a pendant pentafluorophenyl ester group. The first ROP polymer further comprises a backbone segment derived from the ring opening of the first cyclic carbonyl compound, the backbone segment selected from the group consisting of polycarbonates, polyureas polycarbamates, polythiocarbamates, polythiocarbonates, and polydithiocarbonates. The first ROP polymer can further comprise a polyester backbone segment when a cyclic ester (lactone) comonomer is used in the ring opening polymerization. Each of these repeat structures is shown in Table 2. The R group in Table 2 is a backbone fragment formed by the carbons of the ring containing the cyclic carbonyl group.

TABLE 2

| | |
|---|---|
| Polyester | 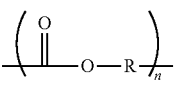 |
| Polycarbonate | 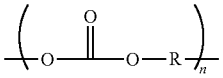 |
| Polyurea | 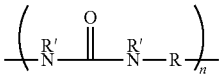 |
| Polycarbamate | 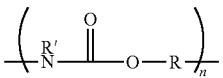 |
| Polythiocarbamate | 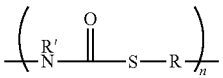 |
| Polythiocarbonate | 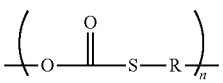 |
| Polydithiocarbonate | 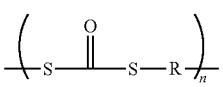 |

The method (Method 3) comprises forming a first mixture comprising a first cyclic carbonyl monomer comprising a pendant pentafluorophenyl ester group, a catalyst, an initiator, an accelerator, and an optional solvent. The first mixture is then agitated with optional heating to effect ring opening polymerization of the first cyclic carbonyl monomer, thereby forming a second mixture containing a biodegradable ROP polymer, while retaining the pendant pentafluorophenyl ester group. The ROP polymer comprises a first polymer chain, the first polymer chain comprising a first repeat unit, the first repeat unit comprising a side chain comprising a pendant pentafluorophenyl ester group. In a specific embodiment, the side chain has the structure:

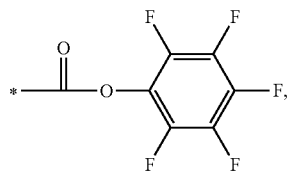

wherein the starred bond is linked to a backbone carbon of the biodegradable first ROP polymer. In another embodiment, the first repeat unit of the first ROP polymer comprises a tetrahedral backbone carbon, the tetrahedral backbone carbon linked to i) a first side chain comprising a pentafluorophenyl ester group, and ii) a second side chain group comprising a monovalent hydrocarbon radical. The monovalent hydrocarbon radical can comprise from 1 to 30 carbons. More specifically, the monovalent hydrocarbon radical is selected from the group consisting of methyl, ethyl, propyl, butyl and pentyl groups.

In an embodiment, the polymer retains at least 50%, and more specifically at least 75%, and even more specifically at least 90% of the pentafluorophenyl ester groups relative to the repeat units derived from the first cyclic carbonyl compounds.

As a non-limiting example, shown in Scheme C, MTC-PhF$_5$ undergoes ring opening polymerization in the presence of a suitable catalyst and nucleophilic initiator to form a ROP polymer, a polycarbonate.

Scheme C.

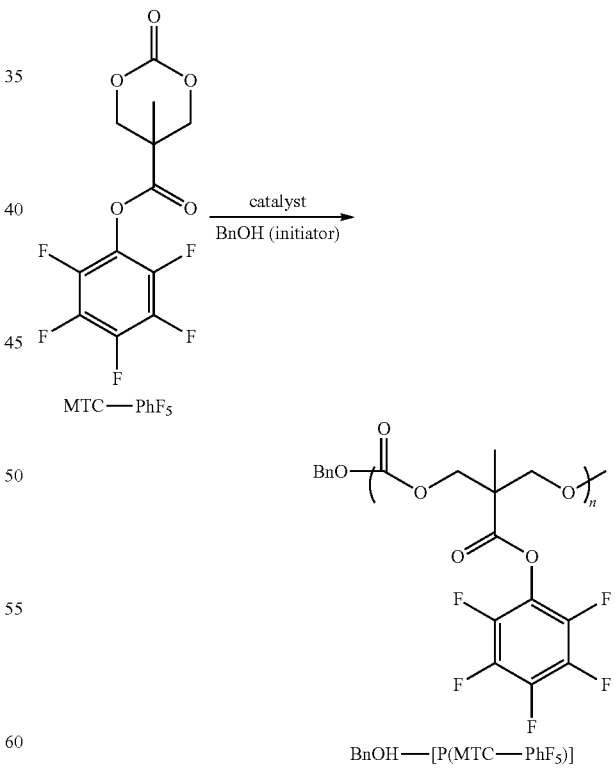

In the naming notation used herein, I-[P(Monomer 1, Monomer 2, etc.)]$_w$, "I" is the initiator, "[P( )]" indicates a polymer chain formed by ring opening polymerization of one or more cyclic carbonyl compounds listed in the parentheses, and w is the number of nucleophilic initiator groups of the initiator. In the above example, the initiator is benzyl alcohol, the initiator fragment is a benzyloxy group (BnO), and the name of the ROP homopolymer is BnOH—[P(MTC-PhF$_5$)]. The ROP polymer can be prepared under mild conditions, achieving high molecular weight and low polydispersity (e.g., Example 16 below). Additionaly, the ROP polymer can be prepared having substantially no metal contaminant when prepared with an organocatalyst. The wide utility and ease of manufacture of the first cyclic carbonyl monomers (and their corresponding ROP polymers) makes these monomers considerably more useful than similar compounds comprising an acyl chloride group or a succinimidyl ester group. The efficient method of forming ROP polymers having an active pentafluorophenyl ester side chain group represents a significant advancement in the state of the art in preparing functionalized ROP polymers.

The first mixture can comprise comonomers, including cyclic ethers, cyclic esters, and cyclic carbonates. Exemplary comonomers include: L-lactide, D-lactide, DL-lactide, beta-butyrolactone, delta-valerolactone, epsilon-caprolactone, trimethylene carbonate, methyl 5-methyl-2-oxo-1,3-dioxane-5-carboxylate, ethyl 5-methyl-2-oxo-1,3-dioxane-5-carboxylate, and other derivatives of MTC-OH. These and other examples of cyclic carbonyl comonomers are listed in Table 3.

TABLE 3

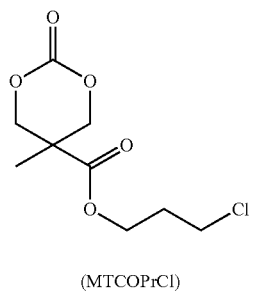

(MTCOPrCl)

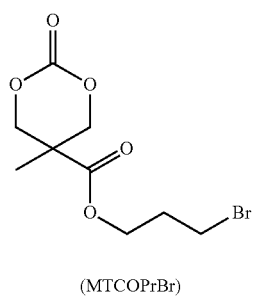

(MTCOPrBr)

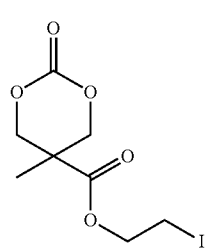

(MTCOEtI)

TABLE 3-continued

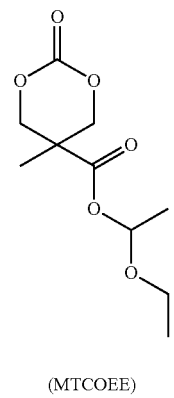

(MTCOEE)

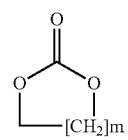

m = 1, Trimethylene carbonate (TMC)
m = 2, Tetramethylene carbonate (TEMC)
m = 3, Pentamethylene carbonate (PMC)

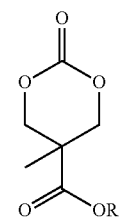

R = hydrogen (MTCOH)
R = methyl (MTCOMe)
R = t-butyl (MTCO$^t$Bu)
R = ethyl (MTCOEt)

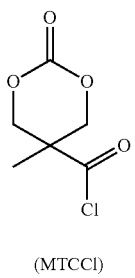

(MTCCl)

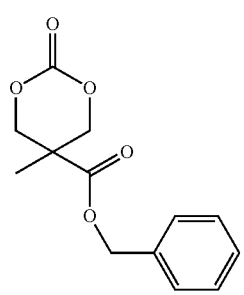 [SMILES: CC1(C(=O)OCc2ccccc2)COC(=O)OC1]

(MTCOBn)

TABLE 3-continued
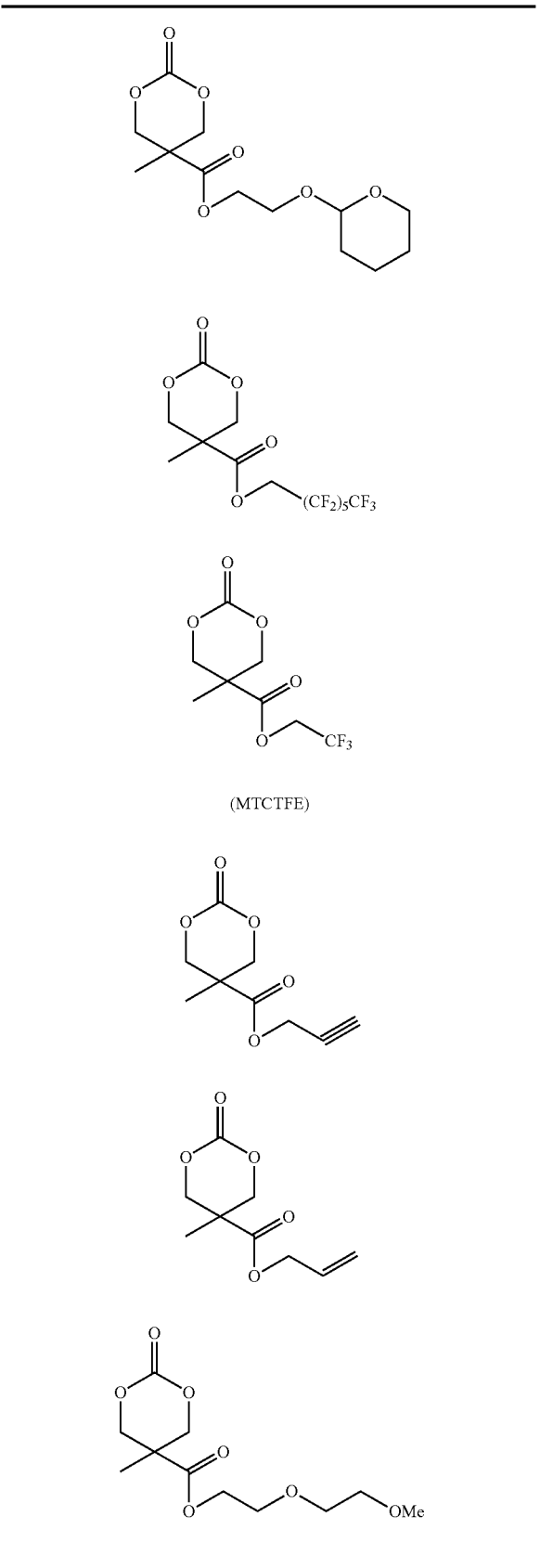
(MTCTFE)
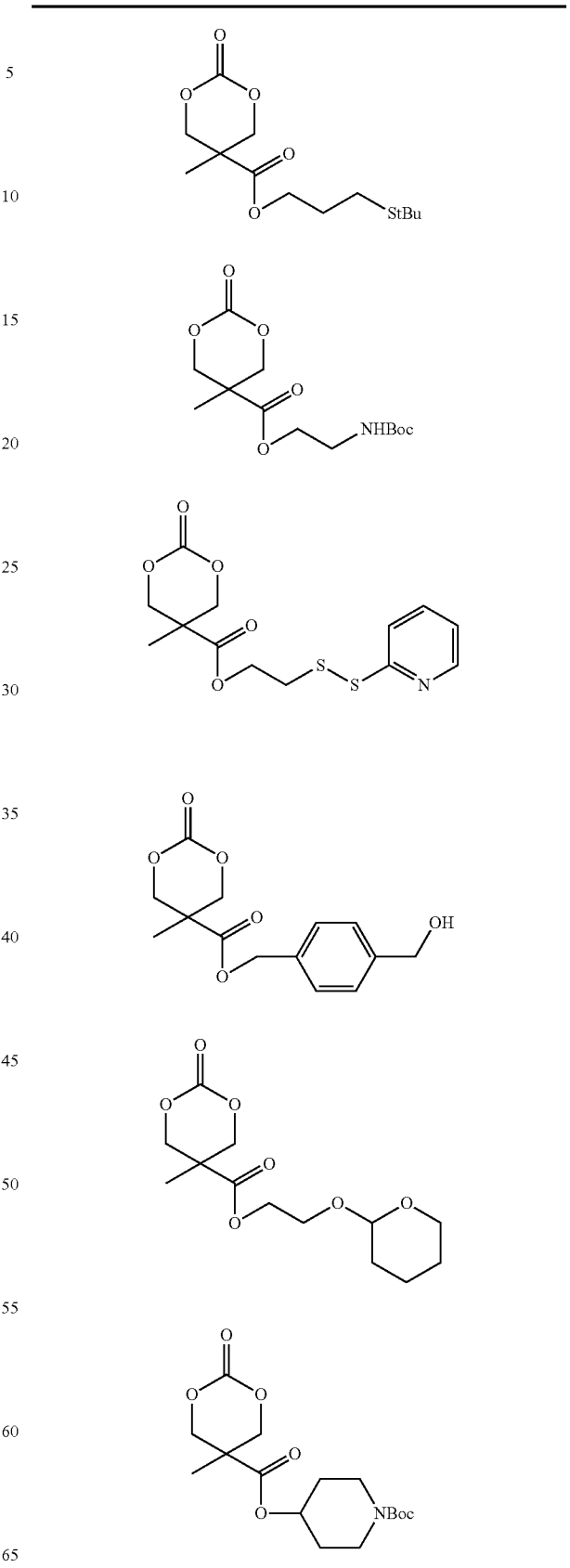

TABLE 3-continued

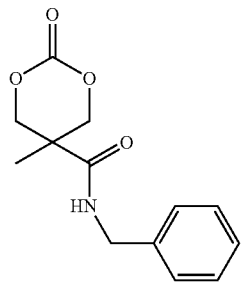 [SMILES: CC1(C(=O)NCc2ccccc2)COC(=O)OC1]

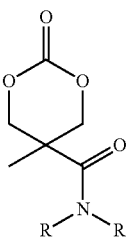

R = methyl
R = iso-propyl

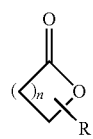

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH₃; n = 1: beta-Butyrolactone (b-BL)
R = CH₃; n = 2: gamma-Valerolactone (g-VL)

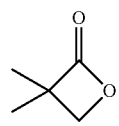

Pivalolactone
(PVL)

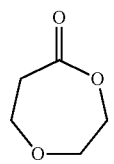

1,5-Dioxepan-2-one
(DXO)

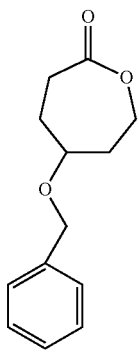 [SMILES: O=C1CCC(OCc2ccccc2)CCO1]

5-(Benzyloxy)oxepan-2-one
(BXO)

TABLE 3-continued

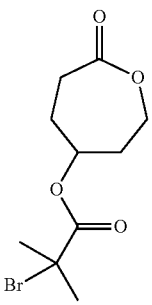

7-Oxooxepan-4-yl 2-bromo-2-methylpropanoate
(BMP-XO)

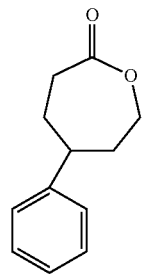 [SMILES: O=C1CCC(c2ccccc2)CCO1]

5-Phenyloxepan-2-one
(PXO)

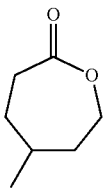

5-Methyloxepan-2-one
(MXO)

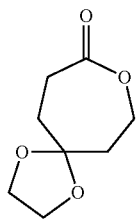 [SMILES: O=C1CCC2(CCO1)OCCO2]

1,4,8-Trioxa(4,6)spiro-9-undecane
(TOSUO)

5-(Benzyloxymethyl)oxepan-2-one
(BOMXO)

TABLE 3-continued

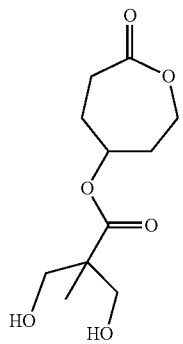

7-Oxooxepan-4-yl 3-hydroxy-2-
(hydroxymethyl)-2-methylpropanoate
(OX-BHMP)

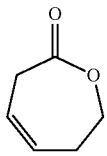

(Z)-6,7-Dihydrooxepin-2(3H)-one
(DHXO)

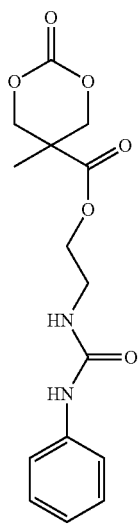 [SMILES: CC1(C(=O)OCCNC(=O)Nc2ccccc2)COC(=O)OC1]

(MTCU)

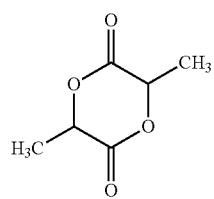

D-Lactide (DLA),
L-Lactide (LLA)
racemic Lactide, 1:1 D:L forms (DLLA)

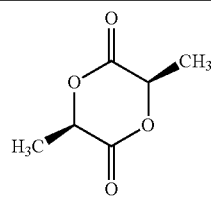

meso-Lactide, (MLA)
(two opposite centers of asymmetry,
R and S)

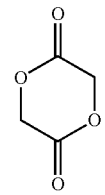

Glycolide
(GLY)

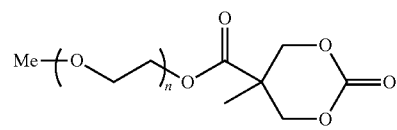

(MTCOMPEG)

Organocatalysts for the ROP Polymerization.

Traditional metal containing catalysts for ring opening polymerization are described above in Part I. Other ROP catalysts include metal-free organocatalysts, defined herein as a catalyst having none of the following metals in the chemical formula of the organocatalyst: beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. This exclusion includes ionic and non-ionic forms of the foregoing metals. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Organocatalysts can provide a platform to polymers having controlled, predictable molecular weights and narrow polydispersities, and minimal metal contamination. Examples of organocatalysts for the ROP of cyclic esters, carbonates and siloxanes are 4-dimethylaminopyridine, phosphines, N-heterocyclic carbenes (NHC), bifunctional aminothioureas, phosphazenes, amidines, guanidines, and fluoroalcohols (such as mono- and bis-hexafluoroisopropanol compounds).

More specific metal-free organocatalysts for the ROP polymerization of the first cyclic monomer include N-(3,5-trifluoromethyl)phenyl-N'-cyclohexyl-thiourea (TU):

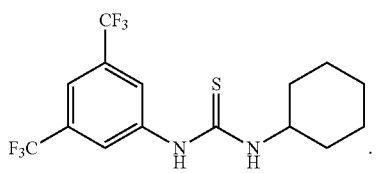

(TU)

Another metal-free ROP catalyst comprises at least one 1,1,1,3,3,3-hexafluoropropan-2-ol-2-yl (HFP) group. Singly-donating hydrogen bond catalysts have the formula (27):

$$R^2—C(CF_3)_2OH \quad (27),$$

wherein $R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalklyl group, aryl group, substituted aryl group, or a combination thereof. Exemplary singly-donating hydrogen bonding catalysts are listed in Table 4.

TABLE 4

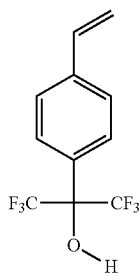 [SMILES: C=Cc1ccc(C(O)(C(F)(F)F)C(F)(F)F)cc1]

4-HFA-St

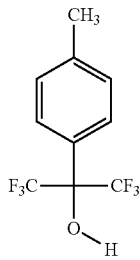 [SMILES: Cc1ccc(C(O)(C(F)(F)F)C(F)(F)F)cc1]

4-HFA-Tol

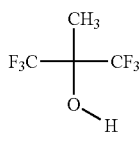

HFTB

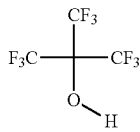

NFTB

TABLE 4-continued

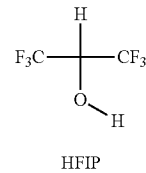

HFIP

Doubly-donating hydrogen bonding catalysts have two HFP groups, represented by the general formula (28):

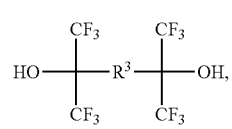

(28)

wherein $R^3$ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (28) include those listed in Table 5. In a specific embodiment, $R^2$ is an arylene or substituted arylene group, and the HFP groups occupy positions meta to each other on the aromatic ring.

TABLE 5

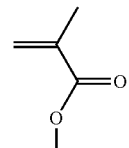

3,5-HFA-MA

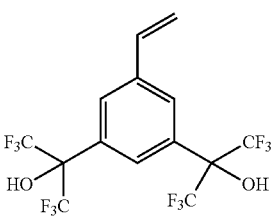 [SMILES: C=Cc1cc(C(O)(C(F)(F)F)C(F)(F)F)cc(C(O)(C(F)(F)F)C(F)(F)F)c1]

3,5-HFA-St

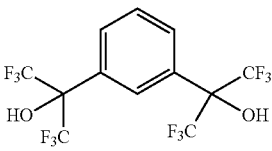

1,3-HFAB

TABLE 5-continued

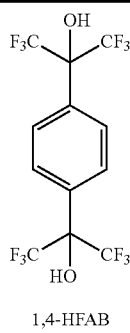

1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

In particular, catalysts bearing 1,3-bis-HFP aromatic groups (such as 1,3-HFAB) were found to be efficient in catalyzing the ROP of MTC-PhF$_5$ without concomitant reaction of the pentafluorophenyl ester side chain.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizeable HFP-containing monomers may be found in: Ito et al., *Polym. Adv. Technol.* 2006, 17(2), 104-115; Ito et al., *Adv. Polym. Sci.* 2005, 172, 37-245; Ito et al., US20060292485; Maeda et al. WO2005098541; Allen et al. US20070254235; and Miyazawa et al. WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003; M. Delgado and K. D. Janda "Polymeric Supports for Solid Phase Organic Synthesis," *Curr. Org. Chem.* 2002, 6(12), 1031-1043; A. R. Vaino and K. D. Janda "Solid Phase Organic Synthesis: A Critical Understanding of the Resin", *J. Comb. Chem.* 2000, 2(6), 579-596; D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377; and T. J. Dickerson et al. "Soluble Polymers as Scaffold for Recoverable Catalysts and Reagents," *Chem. Rev.* 2002, 102(10), 3325-3343. Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

The ROP reaction mixture comprises at least one catalyst and, when appropriate, several catalysts together. The ROP catalyst is added in a proportion of 1/20 to 1/40,000 moles relative to the cyclic compounds, and preferably of 1/1,000 to 1/20,000 moles.

Accelerators for the ROP Polymerization

A nitrogen base can serve as catalyst or as an optional accelerator for a catalyst in a ring opening polymerization. Exemplary nitrogen base are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl)imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 6.

TABLE 6

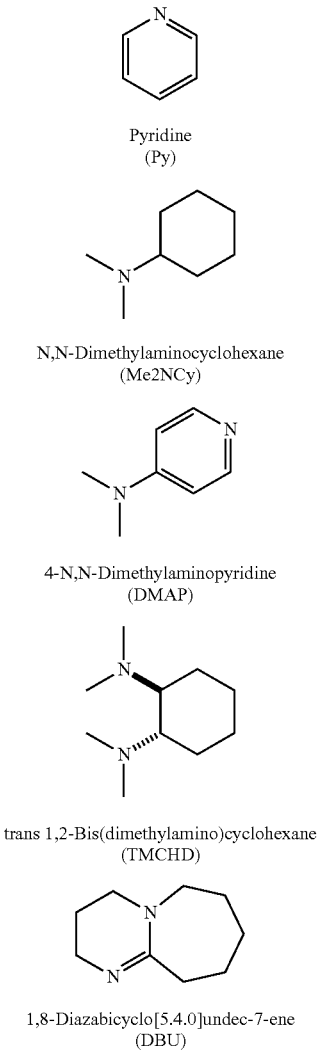

Pyridine
(Py)

N,N-Dimethylaminocyclohexane
(Me2NCy)

4-N,N-Dimethylaminopyridine
(DMAP)

trans 1,2-Bis(dimethylamino)cyclohexane
(TMCHD)

1,8-Diazabicyclo[5.4.0]undec-7-ene
(DBU)

TABLE 6-continued

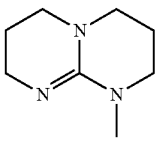

7-Methyl-1,5,7-triazabicyclo[4.4.0]dec-5-ene
(MTBD)

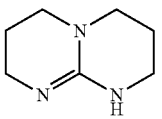

1,5,7-Triazabicyclo[4.4.0]dec-5-ene
(TBD)

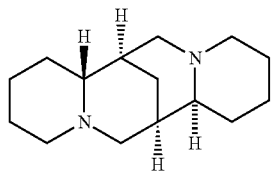 [SMILES: C1CCN2C[C@H]3C[C@H](CN4CCCC[C@@H]34)[C@H]2C1]

(−)-Sparteine
(Sp)

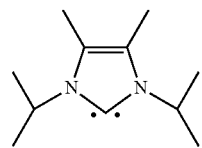

1,3-Bis(2-propyl)-4,5-
dimethylimidazol-2-ylidene
(Im-1)

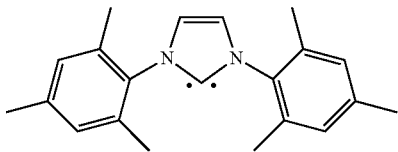

1,3-Bis(2,4,6-trimethylphenyl)imidazol-2-
ylidene
(Im-2)

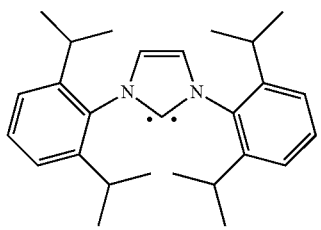 [SMILES: CC(C)c1cccc(C(C)C)c1N1C=CN(c2c(C(C)C)cccc2C(C)C)C1]

1,3-Bis(2,6-di-i-propylphenyl(imidazol-
2-ylidene)
(Im-3)

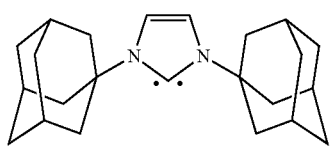 [SMILES: C1=CN(C23CC4CC(CC(C4)C2)C3)CN1C12CC3CC(CC(C3)C1)C2]

1,3-Bis(1-adamantyl)imidazol-2-yliden)
(Im-4)

TABLE 6-continued

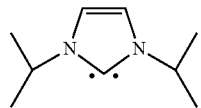

1,3-Di-i-propylimidazol-2-ylidene
(Im-5)

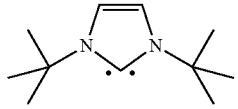

1,3-Di-t-butylimidazol-2-ylidene
(Im-6)

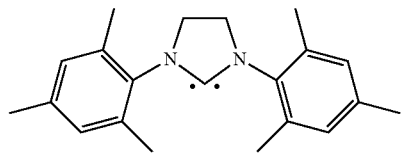

1,3-Bis(2,4,6-trimethylphenyl)-4,5-
dihydroimidazol-2-ylidene
(Im-7)

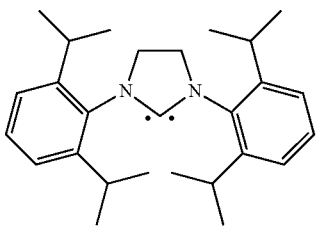 [SMILES: CC(C)c1cccc(C(C)C)c1N1CCN(c2c(C(C)C)cccc2C(C)C)C1]

1,3-Bis(2,6-di-i-propylphenyl)-4,5-
dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate. In some instances, the nitrogen base is the sole catalyst for the ring opening polymerization, such as 1,8-diazabicyclo[5.4.0]undec-7-ene (DBU).

Initiators for the ROP Polymerization

Initiators for the ring opening polymerization have been described above under Part I. These generally include materials having one or more nucleophilic groups selected from the group consisting of alcohols, amines, and thiols. More particularly, the initiator for the ring opening polymerization of the first cyclic monomer bearing a pendant pentafluorophenyl ester is an alcohol. The alcohol initiator can be any suitable alcohol, including mono-alcohol, diol, triol, or other polyol, with the proviso that the choice of alcohol does not adversely affect the polymerization yield, polymer molecular weight, and/or the desirable mechanical and physical properties of the resulting ROP polymer. The alcohol can be multifunctional comprising, in addition to one or more hydroxyl groups, a halide, an ether group, an ester group, an amide group, or other functional group. Additional exemplary alcohols include methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol, other aliphatic saturated alcohols, cyclopentanol, cyclohexanol, cycloheptanol, cyclooctanol, other aliphatic cyclic alcohols, phenol, substituted phenols, benzyl alcohol, substituted benzyl alcohol, benzenedimethanol, trimethylolpropane, a saccharide, poly (ethylene glycol), propylene glycol, alcohol functionalized block copolymers derived from oligomeric alcohols, alcohol functionalized branched polymers derived from branched alcohols, or a combination thereof. Monomeric diol initiators include ethylene glycols, propylene glycols, hydroquinones, and resorcinols. An example of a diol initiator is BnMPA, derived from 2,2-dimethylol propionic acid, a precursor used in the preparation of cyclic carbonate monomers.

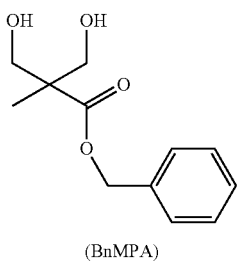 [SMILES: CC(CO)(CO)C(=O)OCc1ccccc1]

(BnMPA)

As indicated above, the ROP initiator can be a polymeric alcohol. More particularly, the ROP initiator can be a polyether alcohol, such as a poly(alkylene glycol) or a mono end capped poly(alkylene glycol) which includes but is not limited to poly(alkylene glycol)s and mono end capped poly (alkylene glycol)s. Such initiators serve to introduce a main chain hydrophilic first block into the resulting first ROP polymer. A second block of the ROP polymer comprises a living chain segment comprising a side chain pentafluorophenyl ester group, the living chain segment formed by ring opening polymerization of a first cyclic carbonyl monomer.

The polyether alcohol can be a poly(alkylene glycol) of the general formula (32):

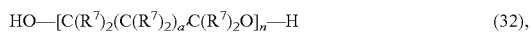

wherein a' is 0 to 8, n is an integer from 2 to 10000, and each $R^7$ is independently a monovalent radical consisting of hydrogen and an alkyl group of 1 to 30 carbons. Thus, the ether repeat unit comprises 2 to 10 backbone carbons between each backbone oxygen. More particularly, the poly(alkylene glycol) can be a mono end capped poly(alkylene glycol), represented by the formula (33):

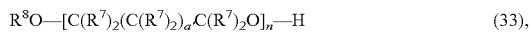

wherein $R^8$ is a monovalent hydrocarbon radical comprising 1 to 20 carbons.

As non-limiting examples, the polyether alcohol can be a poly(ethylene glycol) (PEG), having the structure HO—[$CH_2CH_2O$]$_n$—H, wherein the ether repeat unit $CH_2CH_2O$ (shown in the brackets) comprises two backbone carbons linked to a backbone oxygen. The polyether alcohol can also be a polypropylene glycol) (PPG) having the structure HO—[$CH_2CH(CH_3)O$]$_n$—H, where the ether repeat unit $CH_2CH(CH_3)O$ comprises two backbone carbons linked to a backbone oxygen with a methyl side-chain. An example of mono end capped PEG is the commercially available mono methyl end capped PEG (MPEG), wherein $R^8$ is a methyl group. Other examples include poly(oxetane), having the structure HO—[$CH_2CH_2CH_2O$]$_n$—H, and poly(tetrahydrofuran), having the structure HO—[$CH_2(CH_2)_2CH_2O$]$_n$—H.

The mono end capped poly(alkylene glycol) can comprise more elaborate chemical end groups, represented by the general formula (34):

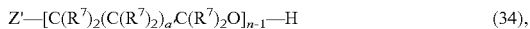

wherein Z' is a monovalent radical including the backbone carbons and oxygen of the end repeat unit, and can have 2 to 100 carbons. The following non-limiting examples illustrate mono end-derivatization of poly(ethylene glycol) (PEG). As described above, one end repeat unit of PEG can be capped with a monovalent hydrocarbon group having 1 to 20 carbons, such as the mono methyl PEG (MPEG), wherein Z' is $MeOCH_2CH_2O$—. The dash on the end of the $MeOCH_2CH_2O$— indicates the point of attachment to the polyether chain. In another example, Z' includes a thiol group, such as $HSCH_2CH_2O$—, or a thioether group, such as $MeSCH_2CH_2O$—. In another example, one end unit of PEG is an aldyhyde, wherein Z' can be $OCHCH_2CH_2O$—. Treating the aldehyde with a primary amine produces an imine, wherein Z' is $R^9N=CHCH_2CH_2O$—. $R^9$ is a monovalent radical selected from hydrogen, an alkyl group of 1 to 30 carbons, or an aryl group comprising 6 to 100 carbons. Continuing, the imine can be reduced to an amine, wherein Z' is $R^9NHCH_2CH_2CH_2O$—. In another example, one end repeat unit of PEG can be oxidized to a carboxylic acid, wherein Z' is $HOOCCH_2O$—. Using known methods the carboxylic acid can be converted to an ester, wherein Z' becomes $R^9OOCCH_2O$—. Alternatively, the carboxylic acid can be converted to an amide, wherein Z' becomes $R^9NHOCCH_2O$—. Many other derivatives are possible. In a particular embodiment, Z' is a group comprising a biologically active moiety that interacts with a specific cell type. For example, the Z' group can comprise a galactose moiety which specifically recognizes liver cells. In this instance, Z' has the structure:

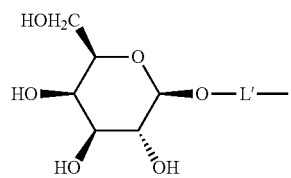

where L' is a divalent linking group comprising 2 to 50 carbons. The hyphen on the right side of L' indicates the attachment point to the polyether chain. Z' can comprise other biologically active moieties such as a mannose moiety.

The ring-opening polymerization can be performed with or without the use of a solvent, more particularly with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl monomer concentration is about 0.1 to 5 moles per liter, and more particularly about 0.2 to 4 moles per liter. In a specific embodiment, the reaction mixture for the ring-opening polymerization contains no solvent.

The ring-opening polymerization of the first cyclic monomer can be performed at a temperature that is about ambient temperature or higher, more specifically a temperature from 15° C. to 200° C., and more particularly 20° C. to 60° C. Reaction times vary with solvent, temperature, agitation rate, pressure, and equipment, but in general the polymerizations are complete within 1 to 100 hours.

Whether performed in solution or in bulk, the polymerizations are conducted in an inert (e.g., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The optional nitrogen base accelerator, when present, is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator is calculated based on the equivalent molecular weight per nucleophilic initiating group in the initiator (e.g., hydroxy groups). The initiating groups are present in an amount of 0.001 to 10.0 mol %, 0.1 to 2.5 mol %, 0.1 to 1.0 mol %, and 0.2 to 0.5 mol %, based on total moles of cyclic carbonyl compound. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the ring opening catalyst is present in an amount of about 0.2 to 20 mol %, the optional accelerator is present in an amount of 0.1 to 5.0 mol %, and the hydroxy groups of the initiator are present in an amount of 0.1 to 5.0 mol % based on the equivalent molecular weight per nucleophilic initiator group in the initiator.

The ring opening polymerization forms a ROP polymer comprising a living polymer chain. The living polymer chain can comprise a terminal hydroxyl group, terminal thiol group, or terminal amine group, each of which can initiate further ROP chain growth, if desired. At least one repeat unit of the ROP polymer comprises a side chain pentafluorophenyl ester group.

In an embodiment, the ROP polymer has a backbone comprising a polycarbonate homopolymer, a random polycarbonate copolymer, or a random polyestercarbonate copolymer. The ROP polymer can comprise a linear polymer, a cyclic polymer, a graft copolymer, and other polymer topologies. The ROP polymer can be a random copolymer, an alternating copolymer, a gradient copolymer, or a block copolymer. Block copolymerization may be achieved by sequentially polymerizing different cyclic carbonyl monomers or by simultaneously copolymerizing monomers with the appropriate reactivity ratios. The ROP polymer can comprise hydrophilic repeat units, hydrophobic repeat units, and combinations thereof, thereby imparting amphiphilic properties to first ROP polymer.

In a preferred embodiment, the catalyst, accelerator, and reaction conditions are selected such that the growing chain end (a nucleophilic alcohol) will not react intramolecularly with a pendant pentafluorophenyl ester group of the same polymer chain to form a cyclic structure or intermolecularly with a pendant pentafluorophenyl ester group of another polymer chain. In this way, linear polymers with controlled polydispersities can be synthesized. At high conversions when the relative concentration of monomer is low, reaction with pendant pentafluorophenyl ester groups can occur with subsequent broadening of the polydispersity.

If the reaction conditions permit (e.g., when a strongly activating catalyst is used), the growing chain end (e.g., a nucleophilic alcohol) may also react with the pendant pentafluorophenyl ester side chain groups of unreacted first cyclic carbonate monomers or the pendant pentafluorophenyl ester side chain groups of the same (i.e., an intramolecular reaction) or another polymer chain (i.e., an intermolecular reaction). Reaction with the pendant pentafluorophenyl ester side chain groups of unreacted first cyclic carbonate monomers will result in the formation of a macromer which may be subsequently be polymerized to make a comb or graft polymer. Intramolecular reaction may produce cyclic structures, while intermolecular reaction may afford a branched polymer. If strongly forcing reaction conditions are used, the growing chain end may also react with the carbonyl structures (e.g., ester, carbonate, etc.) in the polymer main chains and lead to macrocyclization or segmental exchange (by transesterification for example). Such conditions should be avoided if one wants to produce polymers with controlled molecular weights and polydispersities.

Alternatively, if a comonomer comprising additional nucleophilic groups (e.g., OX-BHMP) is used in the preparation of the first ROP polymer comprising a pentafluorophenyl ester side chain group, then these additional nucleophilic groups may serve as initiator groups (which initiate polymer chains) as well as nucleophilic groups which can react with the pendant pentafluorophenyl ester side chain groups. If the additional nucleophilic groups only serve as initiator groups, the result of the synthesis may be a first ROP polymer comprising a pentafluorophenyl ester side chain group with a branched, hyperbranched, comb, bottlebrush, or other such structure. If the reaction conditions permit, the additional nucleophilic groups may also react with the pendant pentafluorophenyl ester side chain groups of unreacted first cyclic carbonate monomers or the pendant pentafluorophenyl ester side chain groups of the same (i.e., an intramolecular reaction) or another polymer chain (i.e., an intermolecular reaction). Intramolecular reaction may produce cyclic structures, while intermolecular reaction may afford a polymeric crosslinked network or gel (which may or may not have any residual pentafluorophenyl ester side chain groups remaining) Again, strongly forcing reaction conditions can allow these nucleophilic groups to also react with the carbonyl structures (e.g., ester, carbonate, etc.) in the polymer main chains, although this is generally undesirable.

The first ROP polymer can be a homopolymer, copolymer, or block copolymer. The polymer can have a number-average molecular weight of usually 1,000 to 200,000, more particularly 2,000 to 100,000, and still more particularly 5,000 to 80,000. In an embodiment, the ROP polymer chain has a number average molecular weight $M_n$ of 10000 to 20000 g/mole. In an embodiment, the ROP polymer chains also have a narrow polydispersity index (PDI), generally from 1.01 to 1.35, more particularly 1.1 to 1.30, and even more particularly 1.1 to 1.25.

Part II, Method 4. Functionalization of the First ROP Polymer.

Further disclosed is a method (Method 4) of converting the first ROP polymer comprising a pentafluorophenyl ester side chain group into a functionalized second polymer by reaction of the pentafluorophenyl ester side chain group with a suitable nucleophile, without disruption of the backbone carbonyl moiety of the first ROP polymer. As a non-limiting example, the functionalization of first ROP polymer BnOH—P(MTC-PhF$_5$) using nucleophile R'—XH is illustrated in Scheme D.

Scheme D.

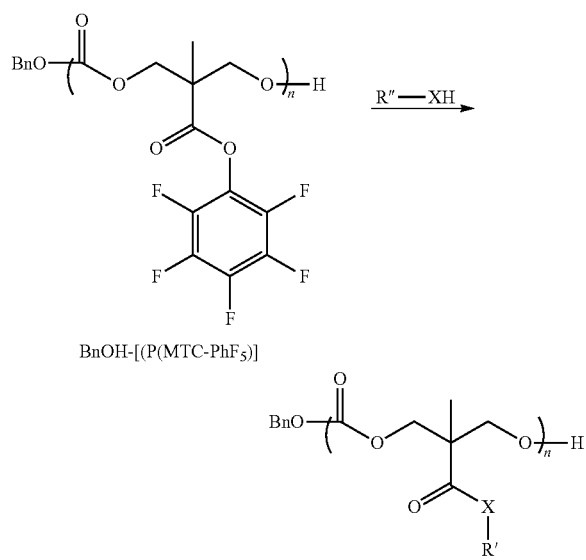

BnOH-[(P(MTC-PhF$_5$)]

R"—XH is a nucleophile selected from the group consisting of alcohols, amines, thiols, and combinations thereof, wherein R" is without restriction with the proviso that a useful polymer is obtained. In an embodiment, R" comprises 1 to 10000 carbons. The functionalized second polymer can be prepared having essentially no remaining pentafluorophenyl ester groups.

The method (Method 4) comprises forming a first mixture comprising the ROP polymer comprising a pentafluorophenyl ester side chain group, an optional second catalyst, a nucleophile selected from the group consisting of alcohols, amines, thiols, and combinations thereof, and an optional solvent. The first mixture is then agitated and optionally heated to effect reaction of the pentafluorophenyl ester with the nucleophile, thereby forming a second mixture containing the functionalized second polymer comprising a pendant functional group selected from the group consisting of alcohol based esters other than a pentafluorophenyl ester, amides, thioesters, and combinations thereof, and pentafluorophenol byproduct.

The first ROP polymer can be treated with a variety of nucleophiles to form a functionalized second polymer. Exemplary nucleophiles include but are not limited to polymeric and non-polymeric alcohols, thiols, and amines described further above under Method 2 and Method 3. When the nucleophile is a polyether alcohol, the functionalized second polymer comprises a side chain ester group comprising a hydrophilic polyether chain.

The nucleophile can further comprise isotopically enriched versions of carbon, nitrogen and hydrogen, including for example $^{13}C$, $^{14}C$, $^{15}N$, deuterium, or combinations thereof. The amine can also comprise a radioactive moiety including a heavy metal radioactive isotope. Method 2 described above can also include a nucleophile comprising isotopically enriched versions of carbon, nitrogen, and hydrogen, as well as a radioactive moiety.

The nucleophile can further comprise additional reactive functional groups including alcohol, amine, thiol, vinyl, allyl, propargyl, acetylene, azide, glycidyl, furan, furfuryl, acrylate, methacrylate, vinyl phenyl, vinyl ketone, vinyl ether, crotyl, fumarate, maleate, maleimide, butadiene, cyclopentadiene, cyclohexadiene, and derivatives thereof. These additional reactive groups may serve as sites for additional subsequent modification through Diels-Alder or Huisgen 1,3-dipolar cycloadditions, for example.

The nucleophile comprising an alcohol group, amine group, thiol group, or combination thereof can be attached to a larger structure including oligomers, polymers, biomacromolecules, particles, and functionalized surfaces. Non-limiting oligomeric and polymeric structures include linear, branched, hyperbranched, cyclic, dendrimeric, block, graft, star, and other known polymer structures. Non-limiting biomacromolecules include carbohydrates, proteins, DNA, RNA, lipids, phospholipids. Particles comprising the nucleophilic groups can have an average diameter ranging from less than 1 nanometer to hundreds of micrometers. Non-limiting functionalized surfaces include silica, alumina, and polymeric resins such as those commonly used for chromatography and functionalized polymeric beads such as those commonly used for solid-phase synthesis.

When multifunctional nucleophiles are used (e.g., diamines, triamines, diols, triols, or aminoalcohols), the functionalization reaction can result in the formation of a functionalized second polymer comprising a crosslinked network or gel. The multifunctional nucleophile can thereby serve as a crosslinking agent by reacting with pentafluorophenyl ester groups from different polymer chains.

Nanoparticulate nucleophiles comprising an alcohol, amine, thiol, or combination thereof, can have an average diameter of from 1 nm to 500 nm. The nanoparticles can comprise both organic and inorganic nanoparticles, including those functionalized with ligands or stabilizing polymers. Organic nanoparticles can include, but are not limited to, crosslinked polymeric nanoparticles, dendrimers, and star polymers. Inorganic nanoparticles include, but are not limited to, metallic nanoparticles (e.g., gold, silver, other transition metals, and Group 13 to Group 16 metals of the Periodic Table), oxide nanoparticles (e.g., alumina, silica, hafnia, zirconia, zinc oxide), nitride nanoparticles (e.g., titanium nitride, gallium nitride), sulfide nanoparticles (e.g., zinc sulfide) semiconducting nanoparticles (e.g., cadmium selenide). Functionalized surfaces include, but are not limited to, surfaces functionalized with self-assembled monolayers.

When multifunctional nucleophiles are used (e.g., diamines, triamines, diols, triols, aminoalcohols . . . etc.), the functionalization reaction can result in the formation of a functionalized second polymer comprising a crosslinked network or gel. The multifunctional nucleophile can thereby serve as a crosslinking agent by reacting with pentafluorophenyl ester groups from different polymer chains.

The reaction of the first ROP polymer with a nucleophile is generally conducted in a reactor under inert atmosphere such as nitrogen or argon. The reaction can be performed using an inactive solvent such as benzene, toluene, xylene, dioxane, chloroform and dichloroethane, methylene chloride, tetrahydrofuran, acetonitrile, N,N-dimethyl formamide, dimethylsulfoxide, dimethyl acetamide, or mixtures thereof. The functionalization reaction temperature can be from 20° C. to 250° C. Generally, the reaction mixture is agitated at room temperature and atmospheric pressure for 0.5 to 72 hours to effect complete conversion of the pentafluorophenyl ester groups. Subsequently, an additional nucleophile and catalyst can be added to the second mixture to effect further functionalization of any non-reacted pentafluorophenyl ester groups. Alternatively, an additional nucleophile and coupling reagent can be added to the second mixture to effect functionalization of any carboxylic acid groups that have formed by hydrolysis of the pendant pentafluorophenyl ester groups.

Typically, the first mixture comprises a solvent, although this is not required. Depending on the solvent, the pentafluorophenol byproduct can in some instances precipitate directly from the reaction mixture as it is formed. Generally, however, the functionalized second polymer can be isolated by precipitation using a suitable non-solvent such as isopropanol. In this manner the functionalized second polymer can be obtained in a yield of about 50% to about 100%, more particularly about 70% to 100%, even more particularly about 80% to 100%.

The optional catalyst of the first mixture (Method 4) can be selected from typical catalysts for transesterifications, conversions of esters to amides, or conversion of esters to thioesters. These include organic catalysts and inorganic catalysts, in particular the above described catalysts, and most specifically cesium fluoride. When used in the first mixture, the catalyst can be present in an amount of 0.02 to 1.00 moles per mole of cyclic carbonyl monomer used to prepare the first ROP polymer, more particularly 0.05 to 0.50 moles per mole of the cyclic carbonyl monomer used to prepare the first ROP polymer, and even more particularly 0.15 to 0.25 moles per mole of the cyclic carbonyl monomer used to prepare the ROP polymer.

In general, the efficacy of the substitution reactions proceed in accordance with the nucleophilicity of the nucleophiles. For example, stronger nucleophiles such as primary amines are more effective than weaker nucleophile such as primary alcohols. In addition, sterically unencumbered nucleophiles react more readily than sterically hindered nucleophiles. For example, substitution using aniline ($PhNH_2$) was more effective than with N-ethyl aniline (PhN(Et)H), a secondary aromatic amine.

In an additional embodiment, the polymerization to form the first ROP polymer (Method 3) comprising a pendant pentafluorophenyl ester group, and the subsequent reaction of the first ROP polymer with a nucleophile to form a functionalized second polymer (Method 4) by displacement of the pentafluorophenoxy group of the pentafluorophenyl ester, are conducted step-wise in a single reaction vessel, without an intermediate step to isolate the first ROP polymer bearing the side chain pentafluorophenyl ester groups.

The above-described methods provide a controlled process for introducing a wide range of functionality and connectivity into polymers formed by ring-opening polymerizations of cyclic carbonyl compounds comprising a pendant pentafluorophenyl ester group. The first ROP polymer and the functionalized second polymer are particularly advantageous because they can be obtained with minimal metal contaminant when produced by an organocatalyst whose chemical formula has none of the following metals: beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table.

In preferred embodiments, the first ROP polymer and/or the functionalized second polymer contains no more than 1000 ppm (parts per million), preferably no more than 100 ppm, more preferably no more than 10 ppm, and still more preferably no more than 1 ppm, of every individual metal of the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. For example, if the limit is no more than 100 ppm, then each of the foregoing metals has a concentration not exceeding 100 ppm in the first ROP polymer, the functionalized second polymer, or both. When an individual metal concentration is below detection capability or has a concentration of zero parts, the concentration is expressed as 0 ppm. In another embodiment, every individual metal of the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration of 0 ppm to 1000 ppm, 0 ppm to 500 ppm, 0 ppm to 100 ppm, 0 ppm to 10 ppm, or even more particularly 0 ppm to 1 ppm in the first ROP polymer, the functionalized second polymer, or both. For example, if the concentration can have a value in the range of 0 ppm to 100 ppm (inclusive), then each of the foregoing metals has a concentration of 0 ppm to 100 ppm in the first ROP polymer, the functionalized second polymer, or both. In another embodiment, the first ROP polymer, the functionalized second polymer, or both comprises less than 1 ppm of every individual metal of the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. To be clear, if the limit is less than 1 ppm, then each of the foregoing metals has a concentration of less than 1 ppm in the first ROP polymer, the functionalized second polymer, or both.

The polymer products of the ROP polymerizations described in Part II can also be applied to conventional molding methods such as compression molding, extrusion molding, injection molding, hollow molding and vacuum molding, and can be converted to molded articles such as various parts, receptacles, materials, tools, films, sheets and fibers. A molding composition can be prepared comprising the polymer and various additives, including for example nucleating agents, pigments, dyes, heat-resisting agents, antioxidants, weather-resisting agents, lubricants, antistatic agents, stabilizers, fillers, strengthened materials, fire retardants, plasticizers, and other polymers. Generally, the molding compositions comprise 30 wt. % to 100 wt. % or more of the polymer based on total weight of the molding composition. More particularly, the molding composition comprises 50 wt. % to 100 wt. % of the polymer.

The first ROP polymer and the functionalized second polymer described in Part II can also be formed into free-standing or supported films by known methods. Non-limiting methods to form supported films include dip coating, spin coating, spray coating, doctor blading. Generally, such coating compositions comprise 0.01 wt. % to 90 wt. % of the polymer based on total weight of the coating composition. More particularly, the molding composition comprises 1 wt. % to 50 wt. % of the polymer based on total weight of the coating composition. The coating compositions generally also include a suitable solvent necessary to dissolve the polymer product.

The coating compositions of Part II can also further include other additives selected so as to optimize desirable properties, such as optical, mechanical, and/or aging properties of the films. Non-limiting examples of additives include surfactants, ultraviolet light absorbing dyes, heat stabilizers, visible light absorbing dyes, quenchers, particulate fillers, and flame retardants. Combinations of additives can also be employed.

The second cyclic carbonyl compounds can also bear polymerizeable functional groups which can be polymerized by ROP, free-radical, CRP, or other polymerization techniques, such as or controlled radical polymerization techniques, including nitroxide-mediated radical polymerization, atom transfer radical polymerization (ATRP), and reversible addition-fragmentation polymerization (RAFT). These monomers can be polymerized through the cyclic carbonyl group, the polymerizeable functional group, or both. The cyclic carbonyl group and the polymerizeable functional group can be polymerized in any order (e.g., ROP of a cyclic carbonate and then polymerization of the functional group, vice versa, or simultaneously). Alternatively, the functional group can be polymerized (or copolymerized) to afford a polymer with pendant cyclic carbonyl groups. These cyclic carbonyl groups can then be reacted to append groups to the polymer. For example, ring-opening reactions of cyclic carbonates with primary or secondary amines are well known to produce hydroxy carbamates.

In the following Examples of Part II, Examples 16, 19-22 and 26 demonstrate Method 3 of ring opening polymerization of a first cyclic carbonyl monomer bearing a pendant pentafluorophenyl ester group. The resulting first ROP polymer comprises a repeat unit comprising a side chain pentafluorophenyl ester group. Examples 17, 18, and 23-24, demonstrate Method 4 of forming a functionalized second polymer by converting the pentafluorophenyl ester side chain group of the first ROP polymer into a different side chain ester or amide using various nucleophiles. Example 25 demonstrates the preparation of first cyclic carbonyl monomer ETC-PhF$_5$, the 5-ethyl analogue of MTC-PhF$_5$.

Part II. Examples 16-26.

Unless indicated otherwise, parts are parts by weight, temperature is in ° C. and pressure is at or near atmospheric. Bis(pentafluorophenyl)carbonate was obtained from Central Glass Co., Ltd. (Japan). All the other starting materials were obtained (in anhydrous grade if possible) from Aldrich Chemical Co. $^1$H, $^{13}$C and $^{19}$F nuclear magnetic resonance (NMR) spectra were obtained at room temperature on a Bruker Avance 400 spectrometer. Table 7 lists materials used in the examples.

TABLE 7

| Name | Description | Company |
|---|---|---|
| bis-MPA | bis(2,2-methylol) propionic acid | Aldrich |
| PFC | bis(pentafluorophenyl) carbonate | Central Glass Co., Ltd. |
| 1,3-HFAB | 1,3-bis(1,1,1,3,3,3-hexafluoro-2-hydroxy-prop-2-yl)benzene; catalyst | Central Glass Co., Ltd. |
| (−)-sparteine | Accelerator | Aldrich |
| CsF | Cesium fluoride; catalyst | Aldrich |

Example 16

Homopolymerization of pentafluorophenyl 5-methyl-2-oxo-1,3-dioxane-5-carboxylate (MTC-PhF$_5$)

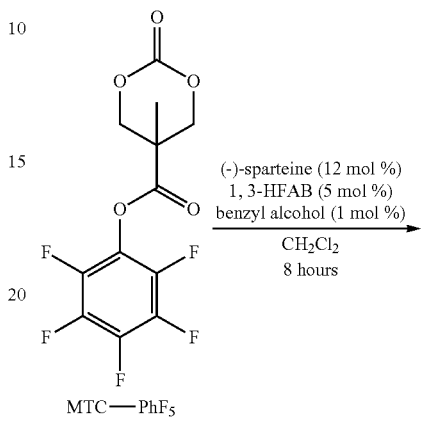

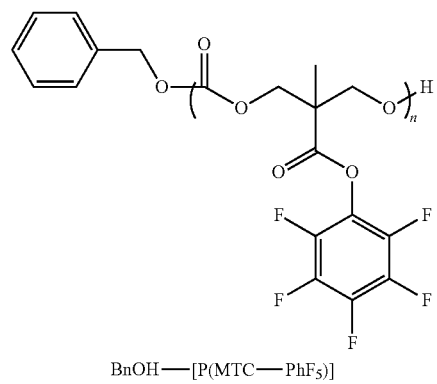

Figure 13:
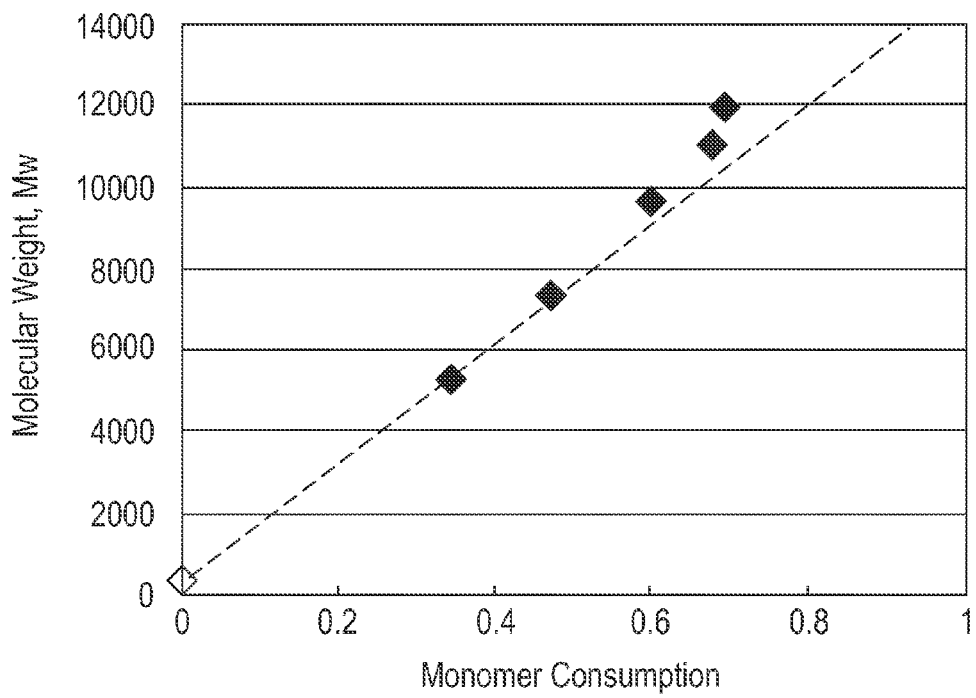
FIGS. 13-15

In a dry 5 mL vial, pentafluorophenyl 5-methyl-2-oxo-1,3-dioxane-5-carboxylate (MTC-PhF$_5$) (301 mg, 0.924 mmol) was combined with 1,3-bis(1,1,1,3,3,3-hexafluoro-2-hydroxy-prop-2-yl)benzene (1,3-HFAB) (19 mg, 0.0462 mmol, 0.05 eq.), (−)-sparteine (22 microliters, 0.12 eq.), and benzyl alcohol (1 microliters, 0.01 eq.) were dissolved in methylene chloride (1.5 mL) and stirred at room temperature. After eight hours, conversion had reached about 70%. The polymer weight average molecular weight ($M_w$) increases linearly versus conversion (as shown in the graph of FIG. 13) which is characteristic of a controlled living polymerization. Only at high conversion does the molecular weight deviate, presumably due to intermolecular coupling of the terminal hydroxyl group with pentafluorophenyl ester groups of other polymer chains. Despite this small amount of intramolecular interaction, the polydispersity index (PDI) remains reasonably narrow. At 70% conversion, the initial ROP polymer BnOH-[P(MTC-PhF$_5$)] had $M_n$=9500 g/mol, $M_w$=12000 g/mol, and PDI=1.26. Approximately 87% of the pentafluorophenyl ester groups were retained in the initial ROP polymer.

Example 17

Functionalization of BnOH—[P(MTC-PhF$_5$)] with 3-(trifluoromethyl)benzyl amine

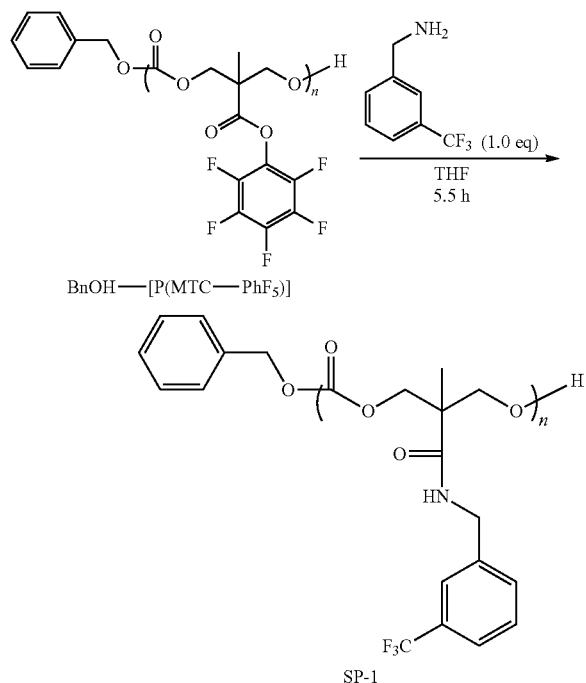

BnOH—[P(MTC—PhF$_5$)]

SP-1

Under a dry nitrogen atmosphere, BnO—[P(MTC-PhF$_5$)] (0.20 g, 0.84 mmol) and 3-(trifluoromethyl)benzyl amine (0.15 g, 0.86 mmol, 1.0 eq.) were dissolved in dry tetrahydrofuran (THF) (0.6 mL). The mixture was stirred for 5.5 hours at room temperature. The functionalized second polymer (SP-1) was isolated by a precipitation in hexane. Percent substitution: 95%. Residual pentafluorophenyl ester: 0%. $M_n$=19,200. $M_n$=65,500 g/mol. PDI=3.41.

Example 18

Functionalization of BnOH—[P(MTC-PhF$_5$)] with 3-(trifluoromethyl)benzyl alcohol

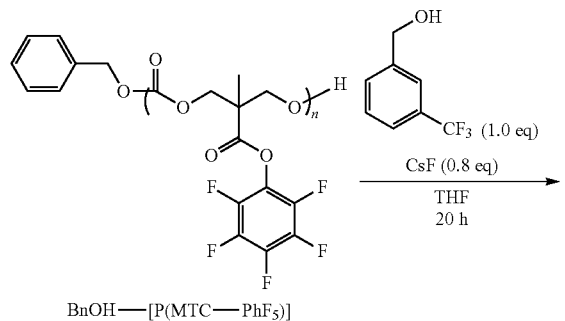

BnOH—[P(MTC—PhF$_5$)]

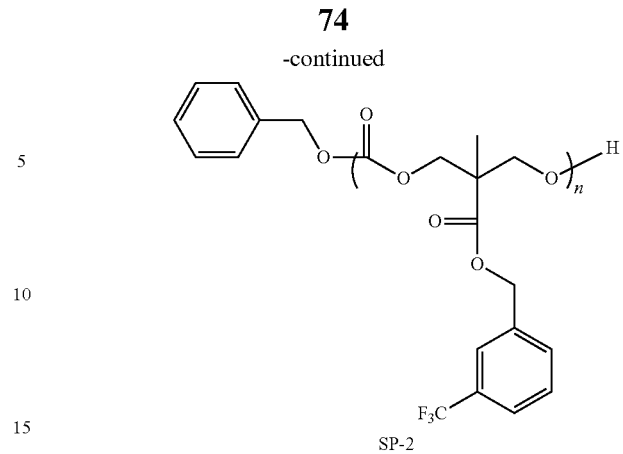

SP-2

Under a dry nitrogen atmosphere, BnOH—[P(MTC-PhF$_5$)] (0.20 g, 0.84 mmol), 3-(trifluoromethyl)benzyl alcohol (0.16 g, 0.92 mmol, 1.05 eq.), and cesium fluoride (0.1 g, 0.66 mmol, 0.8 eq.) were dissolved in dry tetrahydrofuran (THF) (0.6 mL). The mixture was stirred for 20 hours at room temperature. The functionalized second polymer (SP-2) was isolated by a precipitation in hexane. Percent substitution: 50%. Residual pentafluorophenyl ester: 0%. Approximately 50% of the pentafluorophenyl ester groups were lost, presumably due to hydrolysis to carboxylic acid groups during the reaction or polymer isolation. This may have occurred during the reaction due to residual water in the 3-(trifluoromethyl)benzyl alcohol or insufficient drying of the reaction solvent or reaction apparatus or during the precipitation and isolation process. $M_n$=12,000 g/mol. $M_w$=20,100 g/mol. PDI=1.68.

Example 19

Copolymerization of pentafluorophenyl 5-methyl-2-oxo-1,3-dioxane-5-carboxylate (MTC-PhF$_5$) and ethyl 5-methyl-2-oxo-1,3-dioxane-5-carboxylate (MTC-Et)

75
-continued

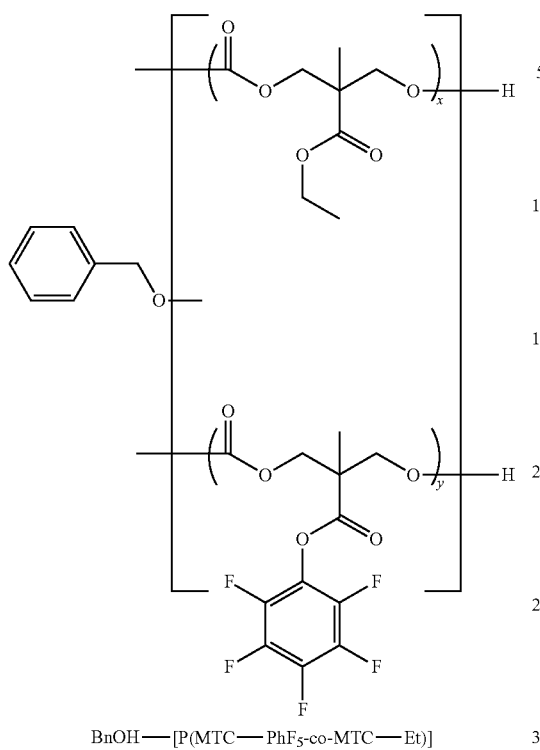

BnOH—[P(MTC—PhF₅-co-MTC—Et)]

Figure 14:
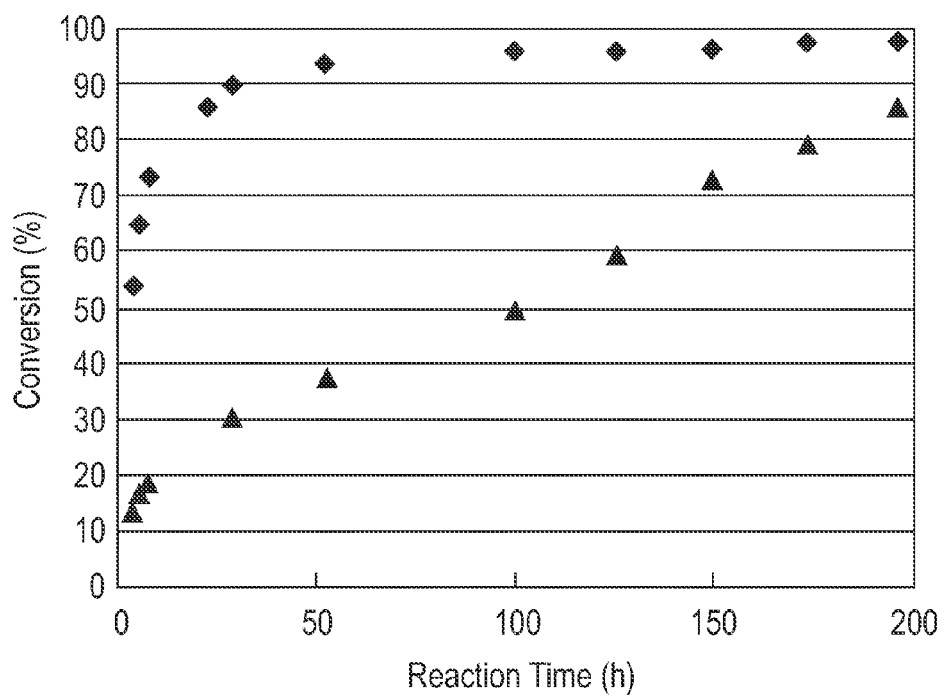

In a dry 2 mL vial, pentafluorophenyl 5-methyl-2-oxo-1,3-dioxane-5-carboxylate (MTC-PhF$_5$) (38.5 mg, 0.118 mmol, 0.1 eq.), ethyl 5-methyl-2-oxo-1,3-dioxane-5-carboxylate (MTC-Et) (200 mg, 1.06 mmol, 0.9 eq.), 1,3-bis(1,1,1,3,3,3-hexafluoro-2-hydroxy-prop-2-yl)benzene (1,3-HFAB) (24 mg, 0.05 eq.), (−)-sparteine (7 microliters, 0.025 eq.), and benzyl alcohol (1.2 microliters, 0.01 eq.) were dissolved in deuterochloroform (750 mg) and stirred at room temperature. The molar ratio of MTC-PhF$_5$ to MTC-Et was 10:90. A graph of the monomer conversion versus time in FIG. 14 reveals the unequal reactivities of these two monomers towards polymerization. From this graph, the pentafluorophenyl ester monomer MTC-PhF$_5$ (diamonds) is incorporated much more rapidly than the ethyl ester monomer (triangles). As a result of this asymmetric incorporation rate, the resulting first polymer BnOH—[P(MTC-PhF$_5$-co-MTC-Et)] is likely a gradient or block-like copolymer rather than the purely random copolymer indicated by the bracketed ladder formula above. After 200 hours, the product BnOH—[P(MTC-PhF$_5$-co-MTC-Et)] had a M$_n$ of 17600 g/mol, a M$_w$ of 26500 g/mol, and a PDI of 1.51.

76

Example 20

Copolymerization of pentafluorophenyl 5-methyl-2-oxo-1,3-dioxane-5-carboxylate (MTC-PhF$_5$) and L-lactide (LLA)

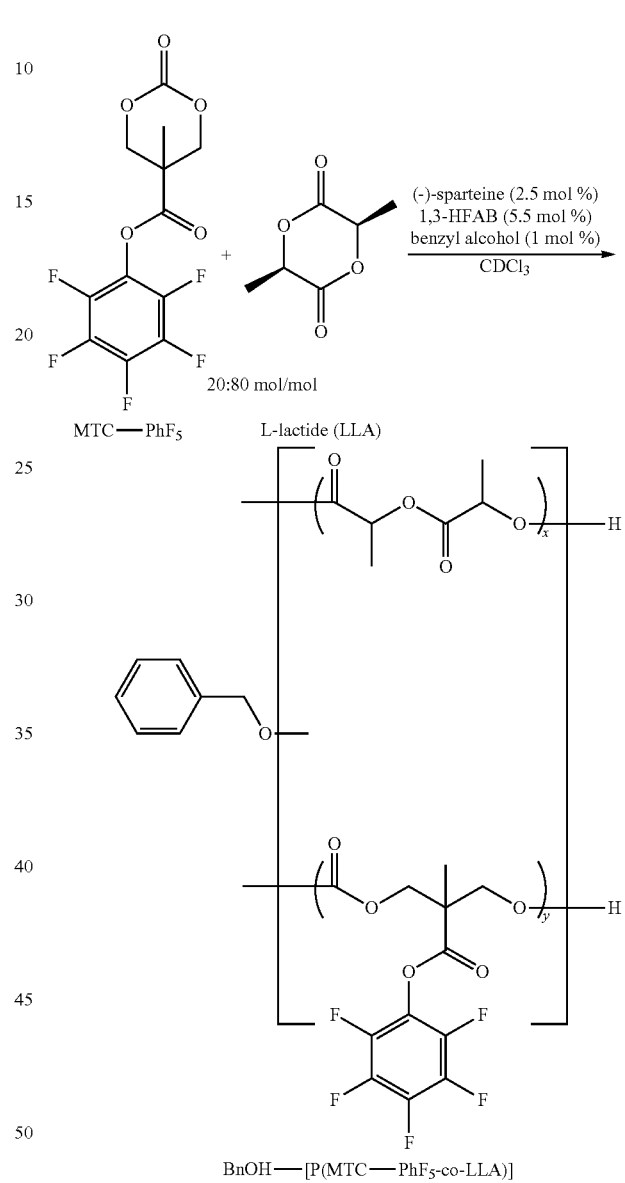

BnOH—[P(MTC—PhF₅-co-LLA)]

Figure 15:
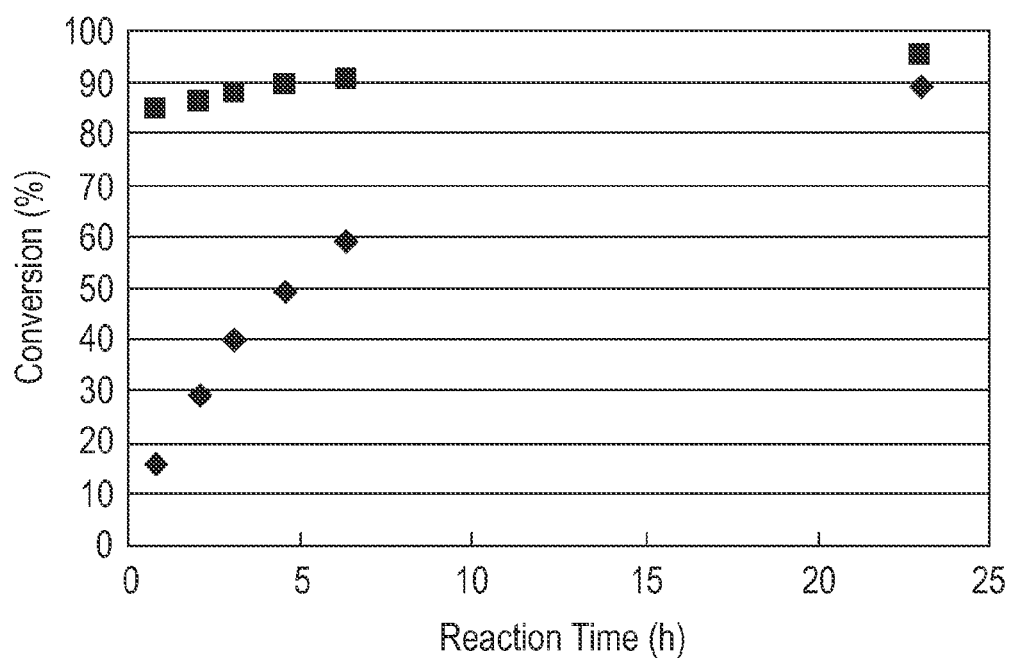

In a dry 5 mL vial, pentafluorophenyl 5-methyl-2-oxo-1,3-dioxane-5-carboxylate (MTC-PhF$_5$) (65.2 mg, 0.20 mmol, 0.2 eq.), L-lactide (115.2 mg, 0.8 mmol, 0.8 eq.), 1,3-bis(1,1,1,3,3,3-hexafluoro-2-hydroxy-prop-2-yl)benzene (1,3-HFAB) (22.5 mg, 0.055 eq.), (−)-sparteine (5.7 microliters, 0.025 eq.), and benzyl alcohol (1 microliter, 0.01 eq.) were dissolved in deuterochloroform (1 mL) and stirred at room temperature. The molar ratio of MTC-PhF$_5$ to L-lactide was 20:80. A graph of the monomer conversion versus time (FIG. 15) again reveals the unequal reactivities of these two monomers towards polymerization. In this instance, however, the pentafluorophenyl ester monomer MTC-PhF$_5$ (diamonds) is incorporated much more slowly than the L-lactide (squares). As a result of this asymmetric incorporation rate, the resulting initial polymer BnOH—[P(MTC-PhF$_5$-co-LLA)] is likely a gradient or block-like copolymer rather than a purely random copolymer, as indicated by the bracketed ladder formula. After 23 hours, the initial polymer BnOH—[P(MTC-PhF$_5$-co-LLA)] had a M$_n$ of 23600 g/mol, a M$_w$ of 27000 g/mol, and a PDI of 1.15.

Example 21

Block copolymerization of pentafluorophenyl 5-methyl-2-oxo-1,3-dioxane-5-carboxylate (MTC-PhF$_5$) and L-lactide (LLA)

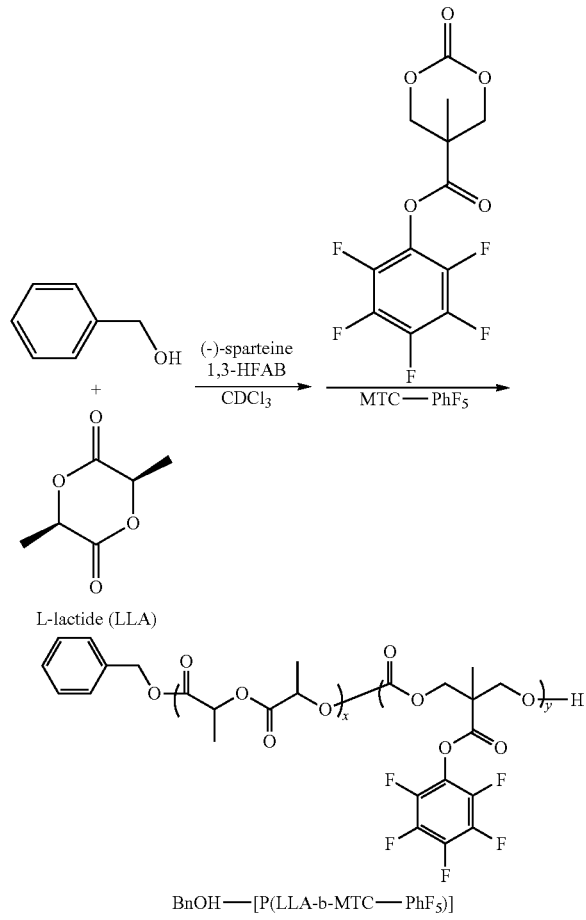

To a dry 100 mL flask, L-lactide (1.92 g, 13.4 mmol, 0.8 eq.), 1,3-bis(1,1,1,3,3,3-hexafluoro-2-hydroxy-prop-2-yl)benzene (1,3-HFAB) (342 mg, 0.055 eq.), (−)-sparteine (98 mg, 0.025 eq.), and benzyl alcohol (18 mg, 0.166 mmol, 0.0123 eq.) were combined in deuterochloroform (15 mL) and stirred at room temperature. After 5 hours, pentafluorophenyl 5-methyl-2-oxo-1,3-dioxane-5-carboxylate (MTC-PhF$_5$) (1.09 g, 3.34 mmol, 0.2 eq.) was added and the solution allowed to stir at room temperature for an additional 20 hours. The block copolymer BnOH—[P(LLA-b-MTC-PhF$_5$)] was isolated via precipitation from 2-propanol and had a M$_n$ of 22200 g/mol, a M$_w$ of 28800 g/mol and a PDI of 1.29. Ratio of x:y=4.1:1. Approximately, 70% of the pentafluorophenyl ester groups were retained after isolation.

Example 22

Block copolymerization of pentafluorophenyl 5-methyl-2-oxo-1,3-dioxane-5-carboxylate (MTC-PhF$_5$) and L-lactide (LLA)

This polymerization is a repeat of Example 21 using 16% by weight additional benzyl alcohol initiator. To a dry 100 mL flask, L-lactide (1.92 g, 13.4 mmol, 0.8 eq.), 1,3-bis(1,1,1,3,3,3-hexafluoro-2-hydroxy-prop-2-yl)benzene (1,3-HFAB) (342 mg, 0.055 eq.), (−)-sparteine (98 mg, 0.025 eq.), and benzyl alcohol (21 mg, 0.194 mmol, 0.0144 eq.) were combined in dichloromethane (15 mL) and stirred at room temperature. After 14 hours, pentafluorophenyl 5-methyl-2-oxo-1,3-dioxane-5-carboxylate (MTC-PhF$_5$) (1.09 g, 3.34 mmol, 0.2 eq.) was added and the solution was allowed to stir at room temperature for an additional 7 hours. The block copolymer BnOH—[P(LLA-b-MTC-PhF$_5$)] was isolated via precipitation from 2-propanol, and had a M$_n$ of 18800 g/mol, a M$_w$ of 21600 g/mol and a PDI of 1.15. Ratio of x:y=4.9:1. Approximately, 99% of the pentafluorophenyl ester groups were retained after isolation.

Example 23

Functionalization of poly(pentafluorophenyl 5-methyl-2-oxo-1,3-dioxane-5-carboxylate-b-l-lactide), referred to above as BnOH—[P(LLA-b-MTC-PhF$_5$)], with 3-(trifluoromethyl)benzyl amine

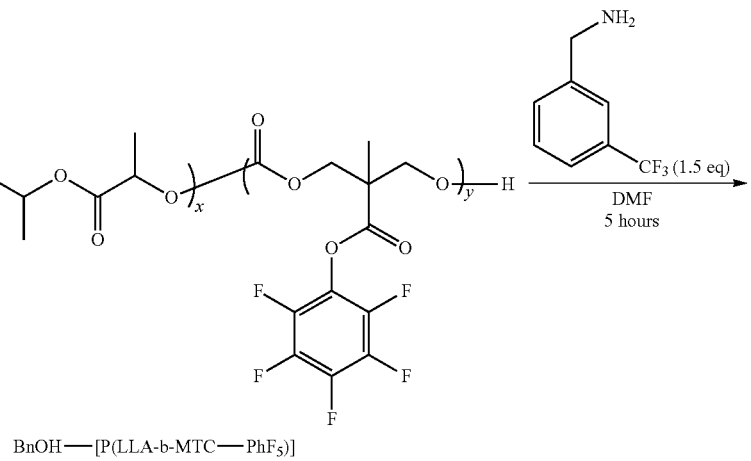

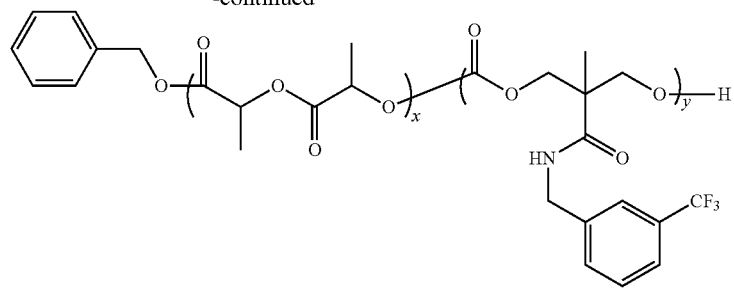

SP-3

Under a dry nitrogen atmosphere, initial polymer BnOH—[P(LLA-b-MTC-PhF$_5$)] (503 mg, 0.389 mmol (as-C$_6$F$_5$ ester)) and 3-(trifluoromethyl)benzyl amine (103 mg, 0.585 mmol, 1.5 eq.) were dissolved in dry N,N-dimethylformamide (DMF) (0.56 g). The mixture was stirred for 5 hours at room temperature. After the reaction, the functionalized second polymer SP-3 was precipitated from methanol. Properties of second polymer SP-3: Percent substitution: 95%.

Residual pentafluorophenyl ester: 0%. $M_n$=23,500 g/mol. $M_w$=32,000 g/mol. PDI=1.36. Ratio of x:y=4.1:1.

Example 24

Functionalization of poly(pentafluorophenyl 5-methyl-2-oxo-1,3-dioxane-5-carboxylate-b-l-lactide), referred to above as BnOH—[P(LLA-b-MTC-PhF$_5$)] with 3-(trifluoromethyl)benzyl alcohol

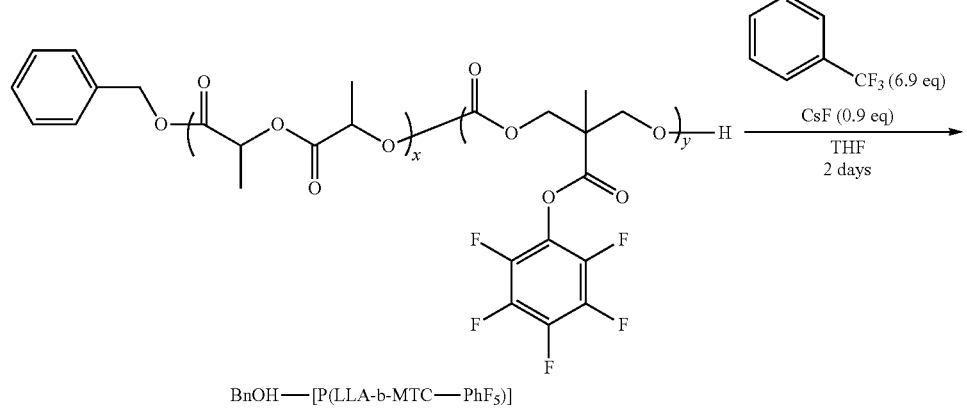

BnOH—[P(LLA-b-MTC—PhF$_5$)]

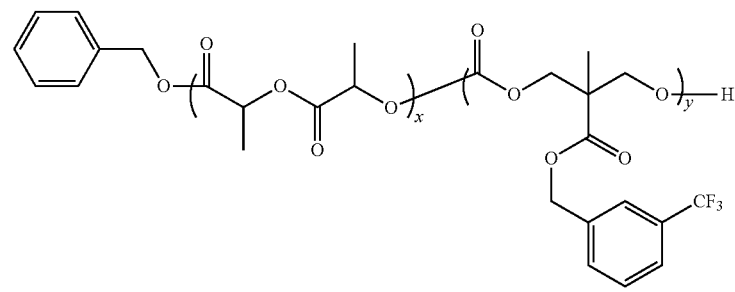

SP-4

Under a dry nitrogen atmosphere, initial polymer BnOH—[P(LLA-b-MTC-PhF$_5$)] (250 mg, 0.194 mmol (as-C$_6$F$_5$ ester)), 3-(trifluoromethyl)benzyl alcohol (235 mg, 1.33 mmol, 6.9 eq.), and cesium fluoride (27 mg, 0.714 mmol, 0.9 eq.) were dissolved in dry tetrahydrofuran (THF). The mixture was stirred for 2 days at room temperature. After the reaction, the functionalized second polymer SP-4 was precipitated from dichloromethane-hexane mixture. Properties of second polymer SP-4: Percent substitution: 59%. Residual pentafluorophenyl ester: 0%. Ratio of x:y=4.1:1. $M_n$=14,300 g/mol. $M_w$=19,600 g/mol. PDI=1.37.

Example 25

Preparation of ETC-PhF$_5$

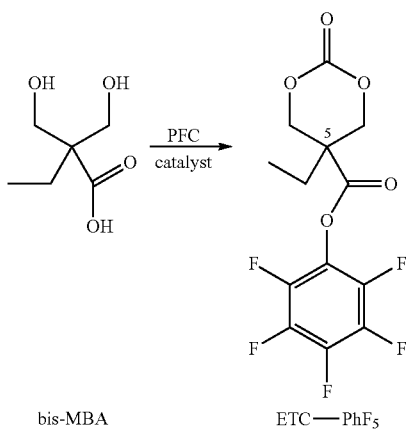

To a 100 mL round bottom flask, 1,1-bis(hydroxymethyl)butanoic acid (3.0 g, 20 mmol) was combined with bis(pentafluorophenyl carbonate) (18.4 g, 47 mmol, 2.3 eq) and cesium fluoride (0.92 g, 6.0 mmol) in tetrahydrofuran (29 mL) and stirred for 20 hours at room temperature. The reaction was concentrated (bath temperature: 30° C. pressure: ~100 mm Hg), and redissolved in methylene chloride. Upon sitting (~10 min) the pentafluorophenol byproduct fell out of solution and could be recovered. After removal of the byproduct by filtration, the mother liquid was washed with aqueous sodium bicarbonate (3×50 mL) (pH of aqueous layer ~8) and brine (1×50 mL). The organic layer was separated and dried over anhydrous sodium sulfate. After filtration, the solution was concentrated to give the crude product.

The crude was dissolved in ethyl acetate (6 mL) at 65° C. n-Hexane (24 mL) was added to the solution at the same temperature after which the solution was slowly cooled to room temperature. After stirring the solution over night, the crystal was separated by filtration (5.1 g, 75% yield).

Example 26

Comparison of the rate of homopolymerization of pentafluorophenyl 5-methyl-2-oxo-1,3-dioxane-5-carboxylate (MTC-PhF$_5$) and pentafluorophenyl 5-ethyl-2-oxo-1,3-dioxane-5-carboxylate (ETC-PhF$_5$)

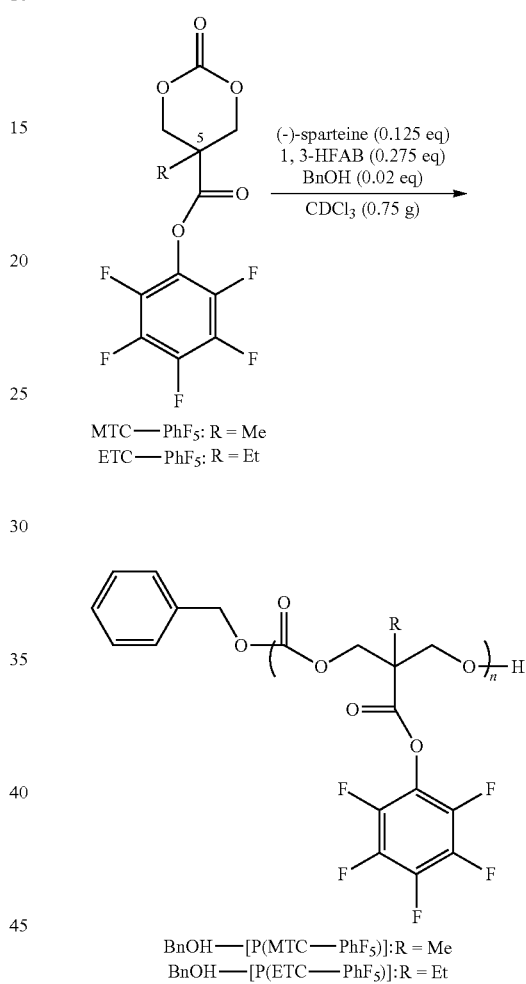

In a NMR tube, pentafluorophenyl 5-methyl-2-oxo-1,3-dioxane-5-carboxylate (MTC-PhF$_5$) or pentafluorophenyl 5-ethyl-2-oxo-1,3-dioxane-5-carboxylate (ETC-PhF$_5$) (0.07 g, 0.2 mmol) was combined with 1,3-bis(1,1,1,3,3,3-hexafluoro-2-hydroxy-prop-2-yl)benzene (1,3-HFAB) (22.5 mg, 0.27 eq.), (−)-sparteine (5.7 microliters, 0.125 eq.), and benzyl alcohol (0.2 microliters, 0.02 eq.) were dissolved in deuterochloroform (0.75 g). The reaction was observed by $^1$H and $^{19}$F NMR. The % conversion at various time intervals is listed in Table 8. From Table 8, the ethyl substituted version ETC-PhF$_5$ displays significantly slower reaction kinetics than the methyl substituted version MTC-PhF$_5$. The size of the substituent group in the 5 position can be used to tune the reactivity of the cyclic carbonate monomers. In such a manner, the relative reactivity of the pentafluorophenyl ester-functionalized cyclic carbonate can be balanced with that of a comonomer in order to attain random copolymers, for example.

TABLE 8

| Time [min] | % Conversion of MTC-PhF$_5$ | % Conversion of ETC-PhF$_5$ |
|---|---|---|
| 73 | 57 | 9 |
| 123 | 84 | |
| 418 | | 30 |
| 1321 | | 63 |
| 1691 | | 73 |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A cyclic carbonyl compound selected from the group consisting of MTC-NiP, MTC-NMe$_2$, MTC-BnAmine, MTC-OCH$_2$CH$_2$CH$_2$Br, MTC-dinitroPHS, MTC-TFE.

2. The compound of claim 1, wherein the compound is

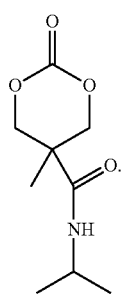

(MTC-NiP)

3. The compound of claim 1, wherein the compound is

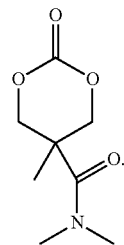

(MTC-NMe$_2$)

4. The compound of claim 1, wherein the compound is

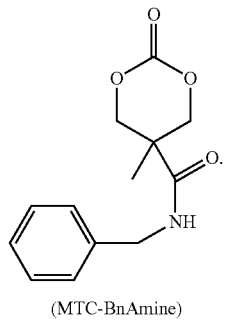 [SMILES: CC1(C(=O)NCc2ccccc2)COC(=O)OC1]

(MTC-BnAmine)

5. The compound of claim 1, wherein the compound is

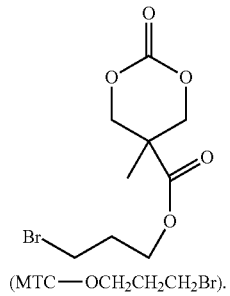

(MTC—OCH$_2$CH$_2$CH$_2$Br).

6. The compound of claim 1, wherein the compound is

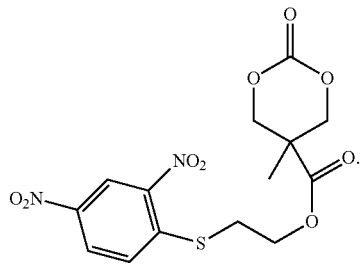

(MTC-dinitroPHS)

7. The compound of claim 1, wherein the compound is
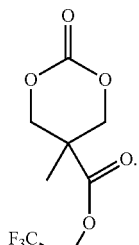
(MTC-TFE)
* * * * *